(12) United States Patent
Takahashi et al.

(10) Patent No.: US 10,968,267 B2
(45) Date of Patent: Apr. 6, 2021

(54) SERUM ALBUMIN-20K GROWTH HORMONE FUSION PROTEIN

(71) Applicant: JCR PHARMACEUTICALS CO., LTD., Ashiya (JP)

(72) Inventors: Kenichi Takahashi, Kobe (JP); Aya Yoshioka, Kobe (JP); Yuri Koshimura, Kobe (JP)

(73) Assignee: JCR PHARMACEUTICALS CO., LTD., Ashiya (JP)

(*) Notice: Subject to any disclaimer, the term of this patent is extended or adjusted under 35 U.S.C. 154(b) by 144 days.

(21) Appl. No.: 16/131,745

(22) Filed: Sep. 14, 2018

(65) Prior Publication Data

US 2019/0010205 A1    Jan. 10, 2019

Related U.S. Application Data

(63) Continuation of application No. PCT/JP2017/009498, filed on Mar. 9, 2017.

(30) Foreign Application Priority Data

Mar. 14, 2016  (JP) .............................. JP2016-049102

(51) Int. Cl.
| | | |
|---|---|---|
| C07K 14/61 | (2006.01) | |
| C07K 14/765 | (2006.01) | |
| A61K 38/27 | (2006.01) | |
| A61K 47/42 | (2017.01) | |
| C12N 15/09 | (2006.01) | |

(52) U.S. Cl.
CPC ............ *C07K 14/61* (2013.01); *C07K 14/765* (2013.01); *A61K 38/27* (2013.01); *A61K 47/42* (2013.01); *C07K 2319/00* (2013.01); *C12N 15/09* (2013.01)

(58) Field of Classification Search
None
See application file for complete search history.

(56) References Cited

U.S. PATENT DOCUMENTS

| | | | |
|---|---|---|---|
| 5,665,863 A | 9/1997 | Yeh | |
| 5,876,969 A | 3/1999 | Fleer et al. | |
| 6,165,470 A | 12/2000 | Becquart et al. | |
| 6,686,179 B2 | 2/2004 | Fleer et al. | |
| 6,972,322 B2 | 12/2005 | Fleer et al. | |
| 6,987,006 B2 | 1/2006 | Fleer et al. | |
| 7,041,478 B2 | 5/2006 | Fleer et al. | |
| 7,056,701 B2 | 6/2006 | Fleer et al. | |
| 7,081,354 B2 | 7/2006 | Fleer et al. | |
| 7,094,577 B2 | 8/2006 | Fleer et al. | |
| 7,410,779 B2 | 8/2008 | Fleer et al. | |
| 7,435,410 B2 | 10/2008 | Fleer et al. | |
| 7,569,384 B2 * | 8/2009 | Rosen .................. | C07K 14/765 435/320.1 |
| 7,833,521 B2 | 11/2010 | Fleer et al. | |
| 2008/0167238 A1 * | 7/2008 | Rosen .................... | A61P 43/00 514/3.8 |
| 2009/0099071 A1 * | 4/2009 | Nakajou .............. | C07K 14/765 514/6.9 |
| 2016/0015789 A1 | 1/2016 | Bock et al. | |
| 2018/0244754 A1 | 8/2018 | Takahashi et al. | |

FOREIGN PATENT DOCUMENTS

| | | | | |
|---|---|---|---|---|
| JP | 3-178998 A | 8/1991 | | |
| JP | 7-503368 A | 4/1995 | | |
| JP | 7-503844 A | 4/1995 | | |
| JP | 2000-502901 A | 3/2000 | | |
| JP | 2003-530838 A | 10/2003 | | |
| JP | 2005-514060 A | 5/2005 | | |
| JP | 2008-43285 A | 2/2008 | | |
| JP | 2008-518615 A | 6/2008 | | |
| JP | 2010-500031 A | 1/2010 | | |
| JP | 2013-501036 A | 1/2013 | | |
| JP | 2013-518038 A | 5/2013 | | |
| WO | WO 97/24445 A1 | 7/1997 | | |
| WO | WO-9724445 A1 * | 7/1997 | ............. | C07K 14/61 |
| WO | WO 01/79258 A1 | 10/2001 | | |
| WO | WO 03/060071 A2 | 7/2003 | | |
| WO | WO 2006/048777 A2 | 5/2006 | | |
| WO | WO 2008/019368 A2 | 2/2008 | | |
| WO | WO 2011/015649 A1 | 2/2011 | | |
| WO | WO 2011/089255 A1 | 7/2011 | | |
| WO | WO 2017/043569 A1 | 3/2017 | | |

OTHER PUBLICATIONS

Tsunekawa et al. (Endocrinol. 140: 3909-3918, 1999).*
International Search Report dated May 30, 2017 in PCT/JP2017/009498, 2 pages.
Poznansky, M.J., et al., "Growth hormone-albumin conjugates Reduced renal toxicity and altered plasma clearance", Federation of European Biochemical Societies, vol. 239, No. 1, Oct. 1988, pp. 18-21.
Hayakawa, M. et al., "Metabolic Effects of 20-Kilodalton Human Growth Hormone (20K-hGH) for Adults with Growth Hormone Deficiency: Results of an Exploratory Uncontrolled Multicenter Clinical Trial of 20K-hGH", Journal of Clinical Endocrinology & Metabolism, 2004, vol. 89, Issue 4, pp. 1562-1571.

(Continued)

*Primary Examiner* — Christine J Saoud
(74) *Attorney, Agent, or Firm* — Oblon, McClelland, Maier & Neustadt, L.L.P.

(57) ABSTRACT

Disclosed is a medicine containing a long-lasting human growth hormone preparation as an active ingredient, which has low prolactin-like activity and shows long half-life in blood as compared with 22K human growth hormone. The long-lasting human growth hormone includes a fusion protein exhibiting growth-promoting activity and having a human serum albumin part and a 20K human growth hormone part, particularly a fusion protein in which the 20K human growth hormone part is linked to C-terminus of the human serum albumin part via a linker sequence.

12 Claims, 20 Drawing Sheets

Specification includes a Sequence Listing.

(56) References Cited

OTHER PUBLICATIONS

Tsushima, T., "20K hGH no Kaihatsu to Rinsho Oyo", Advance in Research of Nervous System, 2003, vol. 47, No. 3, pp. 364 to 370 (with English translation).
Baumann, G.P., et al., "Growth hormone isoforms", Growth Hormone & IGF Research, 2009, vol. 19, Issue 4, pp. 333-340.
Yoshizato, H., et al., "20 kDa Human Growth Hormone (20K hGH) Stimulates Insulin-Like Growth Factor-I (IGF-I) Gene Expression at Lower Concentrations than 22K hGH in hGH Receptor-Expressing Ba/F3 Cells", Endocrine Journal, 2000, vol. 47, Suppl., p. S37-S40.
Strohl, W. R., "Fusion Proteins for Half-Life Extension of Biologics as a Strategy to Make Biobetters", BioDrugs, Jul. 16, 2015, pp. 215-239 (with cover page).
Chen, X., et al., "Fusion Protein Linkers: Property, Design and Functionality", NIH Public Access Author Manuscript, Adv. Drug Deliv. Rev., Oct. 15, 2013, vol. 65, No. 10, pp. 1357-1369.
Tsunekawa B. et al, "The 20-Kilodalton (kDa) Human Growth Hormone (hGH) Differs from the 22-kDa hGH in the Effect on the Human Prolactin Receptor", Endocrinology, XP55675754, vol. 140, No. 9, 1999, pp. 3909-3918.

\* cited by examiner

SEQUENCE LISTING

```
<160> NUMBER OF SEQ ID NOS: 46

<210> SEQ ID NO 1
<211> LENGTH: 176
<212> TYPE: PRT
<213> ORGANISM: Homo sapiens

<400> SEQUENCE: 1

Phe Pro Thr Ile Pro Leu Ser Arg Leu Phe Asp Asn Ala Met Leu Arg
1               5                   10                  15
```

```
Ala His Arg Leu His Gln Leu Ala Phe Asp Thr Tyr Gln Glu Phe Asn
             20                  25                  30

Pro Gln Thr Ser Leu Cys Phe Ser Glu Ser Ile Pro Thr Pro Ser Asn
         35                  40                  45

Arg Glu Glu Thr Gln Gln Lys Ser Asn Leu Glu Leu Leu Arg Ile Ser
     50                  55                  60

Leu Leu Leu Ile Gln Ser Trp Leu Glu Pro Val Gln Phe Leu Arg Ser
65                  70                  75                  80

Val Phe Ala Asn Ser Leu Val Tyr Gly Ala Ser Asp Ser Asn Val Tyr
                 85                  90                  95

Asp Leu Leu Lys Asp Leu Glu Glu Gly Ile Gln Thr Leu Met Gly Arg
            100                 105                 110

Leu Glu Asp Gly Ser Pro Arg Thr Gly Gln Ile Phe Lys Gln Thr Tyr
        115                 120                 125

Ser Lys Phe Asp Thr Asn Ser His Asn Asp Asp Ala Leu Leu Lys Asn
    130                 135                 140

Tyr Gly Leu Leu Tyr Cys Phe Arg Lys Asp Met Asp Lys Val Glu Thr
145                 150                 155                 160

Phe Leu Arg Ile Val Gln Cys Arg Ser Val Glu Gly Ser Cys Gly Phe
                165                 170                 175

<210> SEQ ID NO 2
<211> LENGTH: 585
<212> TYPE: PRT
<213> ORGANISM: Homo sapiens

<400> SEQUENCE: 2

Asp Ala His Lys Ser Glu Val Ala His Arg Phe Lys Asp Leu Gly Glu
1               5                   10                  15

Glu Asn Phe Lys Ala Leu Val Leu Ile Ala Phe Ala Gln Tyr Leu Gln
             20                  25                  30

Gln Cys Pro Phe Glu Asp His Val Lys Leu Val Asn Glu Val Thr Glu
         35                  40                  45

Phe Ala Lys Thr Cys Val Ala Asp Glu Ser Ala Glu Asn Cys Asp Lys
     50                  55                  60

Ser Leu His Thr Leu Phe Gly Asp Lys Leu Cys Thr Val Ala Thr Leu
65                  70                  75                  80

Arg Glu Thr Tyr Gly Glu Met Ala Asp Cys Cys Ala Lys Gln Glu Pro
                 85                  90                  95

Glu Arg Asn Glu Cys Phe Leu Gln His Lys Asp Asp Asn Pro Asn Leu
            100                 105                 110

Pro Arg Leu Val Arg Pro Glu Val Asp Val Met Cys Thr Ala Phe His
        115                 120                 125

Asp Asn Glu Glu Thr Phe Leu Lys Lys Tyr Leu Tyr Glu Ile Ala Arg
    130                 135                 140

Arg His Pro Tyr Phe Tyr Ala Pro Glu Leu Leu Phe Phe Ala Lys Arg
145                 150                 155                 160

Tyr Lys Ala Ala Phe Thr Glu Cys Cys Gln Ala Ala Asp Lys Ala Ala
                165                 170                 175

Cys Leu Leu Pro Lys Leu Asp Glu Leu Arg Asp Glu Gly Lys Ala Ser
            180                 185                 190

Ser Ala Lys Gln Arg Leu Lys Cys Ala Ser Leu Gln Lys Phe Gly Glu
        195                 200                 205

Arg Ala Phe Lys Ala Trp Ala Val Ala Arg Leu Ser Gln Arg Phe Pro
    210                 215                 220
```

-continued

```
Lys Ala Glu Phe Ala Glu Val Ser Lys Leu Val Thr Asp Leu Thr Lys
225                 230                 235                 240

Val His Thr Glu Cys Cys His Gly Asp Leu Leu Glu Cys Ala Asp Asp
            245                 250                 255

Arg Ala Asp Leu Ala Lys Tyr Ile Cys Glu Asn Gln Asp Ser Ile Ser
        260                 265                 270

Ser Lys Leu Lys Glu Cys Cys Glu Lys Pro Leu Leu Glu Lys Ser His
    275                 280                 285

Cys Ile Ala Glu Val Glu Asn Asp Glu Met Pro Ala Asp Leu Pro Ser
290                 295                 300

Leu Ala Ala Asp Phe Val Glu Ser Lys Asp Val Cys Lys Asn Tyr Ala
305                 310                 315                 320

Glu Ala Lys Asp Val Phe Leu Gly Met Phe Leu Tyr Glu Tyr Ala Arg
            325                 330                 335

Arg His Pro Asp Tyr Ser Val Val Leu Leu Leu Arg Leu Ala Lys Thr
        340                 345                 350

Tyr Glu Thr Thr Leu Glu Lys Cys Cys Ala Ala Ala Asp Pro His Glu
    355                 360                 365

Cys Tyr Ala Lys Val Phe Asp Glu Phe Lys Pro Leu Val Glu Glu Pro
370                 375                 380

Gln Asn Leu Ile Lys Gln Asn Cys Glu Leu Phe Glu Gln Leu Gly Glu
385                 390                 395                 400

Tyr Lys Phe Gln Asn Ala Leu Leu Val Arg Tyr Thr Lys Lys Val Pro
            405                 410                 415

Gln Val Ser Thr Pro Thr Leu Val Glu Val Ser Arg Asn Leu Gly Lys
        420                 425                 430

Val Gly Ser Lys Cys Cys Lys His Pro Glu Ala Lys Arg Met Pro Cys
    435                 440                 445

Ala Glu Asp Tyr Leu Ser Val Val Leu Asn Gln Leu Cys Val Leu His
450                 455                 460

Glu Lys Thr Pro Val Ser Asp Arg Val Thr Lys Cys Cys Thr Glu Ser
465                 470                 475                 480

Leu Val Asn Arg Arg Pro Cys Phe Ser Ala Leu Glu Val Asp Glu Thr
            485                 490                 495

Tyr Val Pro Lys Glu Phe Asn Ala Glu Thr Phe Thr Phe His Ala Asp
        500                 505                 510

Ile Cys Thr Leu Ser Glu Lys Glu Arg Gln Ile Lys Lys Gln Thr Ala
    515                 520                 525

Leu Val Glu Leu Val Lys His Lys Pro Lys Ala Thr Lys Glu Gln Leu
530                 535                 540

Lys Ala Val Met Asp Asp Phe Ala Ala Phe Val Glu Lys Cys Cys Lys
545                 550                 555                 560

Ala Asp Asp Lys Glu Thr Cys Phe Ala Glu Glu Gly Lys Lys Leu Val
            565                 570                 575

Ala Ala Ser Gln Ala Ala Leu Gly Leu
        580                 585

<210> SEQ ID NO 3
<211> LENGTH: 191
<212> TYPE: PRT
<213> ORGANISM: Homo sapiens

<400> SEQUENCE: 3

Phe Pro Thr Ile Pro Leu Ser Arg Leu Phe Asp Asn Ala Met Leu Arg
```

```
                1               5                    10                   15
        Ala His Arg Leu His Gln Leu Ala Phe Asp Thr Tyr Gln Glu Phe Glu
                        20                    25                   30

Glu Ala Tyr Ile Pro Lys Glu Gln Lys Tyr Ser Phe Leu Gln Asn Pro
                        35                    40                   45

Gln Thr Ser Leu Cys Phe Ser Glu Ser Ile Pro Thr Pro Ser Asn Arg
         50                       55                    60

Glu Glu Thr Gln Gln Lys Ser Asn Leu Glu Leu Leu Arg Ile Ser Leu
         65                       70                    75                   80

Leu Leu Ile Gln Ser Trp Leu Glu Pro Val Gln Phe Leu Arg Ser Val
                        85                    90                   95

Phe Ala Asn Ser Leu Val Tyr Gly Ala Ser Asp Ser Asn Val Tyr Asp
                        100                   105                  110

Leu Leu Lys Asp Leu Glu Glu Gly Ile Gln Thr Leu Met Gly Arg Leu
                        115                   120                  125

Glu Asp Gly Ser Pro Arg Thr Gly Gln Ile Phe Lys Gln Thr Tyr Ser
         130                      135                   140

Lys Phe Asp Thr Asn Ser His Asn Asp Asp Ala Leu Leu Lys Asn Tyr
        145                       150                   155                  160

Gly Leu Leu Tyr Cys Phe Arg Lys Asp Met Asp Lys Val Glu Thr Phe
                        165                   170                  175

Leu Arg Ile Val Gln Cys Arg Ser Val Glu Gly Ser Cys Gly Phe
                        180                   185                  190

<210> SEQ ID NO 4
<211> LENGTH: 5
<212> TYPE: PRT
<213> ORGANISM: Artificial Sequence
<220> FEATURE:
<223> OTHER INFORMATION: primary amino acid sequence of linker portion

<400> SEQUENCE: 4

Gly Gly Gly Gly Ser
1               5

<210> SEQ ID NO 5
<211> LENGTH: 20
<212> TYPE: PRT
<213> ORGANISM: Artificial Sequence
<220> FEATURE:
<223> OTHER INFORMATION: amino acid sequence of an exemplified linker
      portion

<400> SEQUENCE: 5

Gly Gly Gly Gly Ser Gly Gly Gly Ser Gly Gly Gly Ser Gly
1               5                   10                  15

Gly Gly Gly Ser
        20

<210> SEQ ID NO 6
<211> LENGTH: 23
<212> TYPE: DNA
<213> ORGANISM: Murine endogenous retrovirus

<400> SEQUENCE: 6
atgataatat ggccacaacc atg                                          23

<210> SEQ ID NO 7
<211> LENGTH: 23
<212> TYPE: DNA
```

```
<213> ORGANISM: Artificial Sequence
<220> FEATURE:
<223> OTHER INFORMATION: partial nucleic acid sequence of IRES derived
      from mutant type murine Encephalomyocarditis virus, synthetic
      sequence

<400> SEQUENCE: 7
atgataagct tgccacaacc atg                                              23

<210> SEQ ID NO 8
<211> LENGTH: 20
<212> TYPE: DNA
<213> ORGANISM: Artificial Sequence
<220> FEATURE:
<223> OTHER INFORMATION: Primer Hyg-Sfi5', synthetic sequence

<400> SEQUENCE: 8
gaggccgcct cggcctctga                                                  20

<210> SEQ ID NO 9
<211> LENGTH: 29
<212> TYPE: DNA
<213> ORGANISM: Artificial Sequence
<220> FEATURE:
<223> OTHER INFORMATION: Primer Hyg-BstX3', synthetic sequence

<400> SEQUENCE: 9
aaccatcgtg atgggtgcta ttcctttgc                                        29

<210> SEQ ID NO 10
<211> LENGTH: 2216
<212> TYPE: DNA
<213> ORGANISM: Artificial Sequence
<220> FEATURE:
<223> OTHER INFORMATION: IRES-Hygr-mPGKpA, synthetic sequence

<400> SEQUENCE: 10
ctcgaggaat tcactccttc aggtgcaggc ttgcctatca gaaggtggtg gctggtgtgg      60
ccaactggct cacaaatacc actgagatcg acggtatcga taagcttgat atcgaattcc     120
gcccccccccc cctctccctc cccccccccct aacgttactg gccgaagccg cttggaataa     180
ggccggtgtg cgtttgtcta tatgttattt tccaccatat tgccgtcttt tggcaatgtg     240
agggcccgga aacctggccc tgtcttcttg acgagcattc ctaggggtct ttcccctctc     300
gccaaaggaa tgcaaggtct gttgaatgtc gtgaaggaag cagttcctct ggaagcttct     360
tgaagacaaa caacgtctgt agcgaccctt gcaggcagc ggaacccccc acctggcgac      420
aggtgcctct gcggccaaaa gccacgtgta agatacac ctgcaaaggc ggcacaaccc       480
cagtgccacg ttgtgagttg gatagttgtg gaaagagtca atggctctc ctcaagcgta      540
ttcaacaagg ggctgaagga tgcccagaag gtaccccatt gtatgggatc tgatctgggg     600
cctcggtgca catgctttac atgtgtttag tcgaggttaa aaaacgtct aggcccccg       660
aaccacgggg acgtggtttt ccttgaaaa acacgatgat aatatggcca caaccatgaa      720
aaagcctgaa ctcaccgcga cgtctgtcga agtttctg atcgaaaagt tcgacagcgt       780
ctccgacctg atgcagctct cggaggggcga agaatctcgt gctttcagct tcgatgtagg      840
agggcgtgga tatgtcctgc gggtaaatag ctgcgccgat ggtttctaca aagatcgtta      900
tgttcatcgg cactttgcat cggccgcgct cccgattccg gaagtgcttg acattgggga     960
attcagcgag agcctgacct attgcatctc ccgccgtgca cagggtgtca cgttgcaaga    1020
cctgcctgaa accgaactgc ccgctgttct gcagccggtc gcggaggcca tggatgcgat    1080
```

```
cgctgcggcc gatcttagcc agacgagcgg gttcggccca ttcggaccgc aaggaatcgg   1140
tcaatacact acgtggcgtg atttcatatg cgcgattgct gatccccatg tgtatcactg   1200
gcaaactgtg atggacgaca ccgtcagtgc gtccgtcgcg caggctctcg atgagctgat   1260
gctttgggcc gaggactgcc ccgaagtccg gcacctcgtg cacgcggatt tcggctccaa   1320
caatgtcctg acggacaatg ccgcataaca gcggtcatt gactggagcg aggcgatgtt    1380
cggggattcc caatacgagg tcgccaacat cttcttctgg aggccgtggt tggcttgtat   1440
ggagcagcag acgcgctact cgagcggagg catccggagc cttgcaggat cgccgcggct   1500
ccgggcgtat atgctccgca ttggtcttga ccaactctat cagagcttgg ttgacggcaa   1560
tttcgatgat gcagcttggg cgcagggtcg atgcgacgca atcgtccgat ccggagccgg   1620
gactgtcggg cgtacacaaa tcgcccgcag aagcgcggcc gtctggaccg atggctgtgt   1680
agaagtactc gccgatagtg gaaaccgacg ccccagcact cgtccgaggg caaggaata    1740 gtcgagaaat tgatgatcta ttaagcaata aagacgtcca ctaaaatgga agttttctct   1800
gtcatacttt gttaagaagg gtgagaacag agtacctaca ttttgaatgg aaggattgga   1860
gctacggggg tgggggtggg gtgggattag ataaatgcct gctctttact gaaggctctt   1920
tactattgct ttatgataat gtttcatagt tggatatcat aatttaaaca agcaaaacca   1980
aattaagggc cagctcattc ctccactcac gatctataga tccactagct tggcgtaatc   2040
atggtcatag ctgtttcctg tgtgaaattg ttatccgctc acaattccac acaacatacg   2100
agccggaagc ataaagtgta aagcctgggg tgcctaatga gtgagctaac tcacattaat   2160
tgcgttgcgc tcactgcccg ctttccagtc gggaaacctg tcgtgccagc ggatcc       2216
```

<210> SEQ ID NO 11
<211> LENGTH: 341
<212> TYPE: PRT
<213> ORGANISM: Artificial Sequence
<220> FEATURE:
<223> OTHER INFORMATION: amino acid sequence corresponding to hygromycin
      resistance gene

<400> SEQUENCE: 11

```
Met Lys Lys Pro Glu Leu Thr Ala Thr Ser Val Glu Lys Phe Leu Ile
1               5                   10                  15

Glu Lys Phe Asp Ser Val Ser Asp Leu Met Gln Leu Ser Glu Gly Glu
            20                  25                  30

Glu Ser Arg Ala Phe Ser Phe Asp Val Gly Gly Arg Gly Tyr Val Leu
        35                  40                  45

Arg Val Asn Ser Cys Ala Asp Gly Phe Tyr Lys Asp Arg Tyr Val His
    50                  55                  60

Arg His Phe Ala Ser Ala Ala Leu Pro Ile Pro Glu Val Leu Asp Ile
65                  70                  75                  80

Gly Glu Phe Ser Glu Ser Leu Thr Tyr Cys Ile Ser Arg Arg Ala Gln
                85                  90                  95

Gly Val Thr Leu Gln Asp Leu Pro Glu Thr Glu Leu Pro Ala Val Leu
            100                 105                 110

Gln Pro Val Ala Glu Ala Met Asp Ala Ile Ala Ala Ala Asp Leu Ser
        115                 120                 125

Gln Thr Ser Gly Phe Gly Pro Phe Gly Pro Gln Gly Ile Gly Gln Tyr
    130                 135                 140

Thr Thr Trp Arg Asp Phe Ile Cys Ala Ile Ala Asp Pro His Val Tyr
145                 150                 155                 160
```

-continued

```
His Trp Gln Thr Val Met Asp Thr Val Ser Ala Ser Val Ala Gln
            165                 170                 175

Ala Leu Asp Glu Leu Met Leu Trp Ala Glu Asp Cys Pro Glu Val Arg
        180                 185                 190

His Leu Val His Ala Asp Phe Gly Ser Asn Asn Val Leu Thr Asp Asn
            195                 200                 205

Gly Arg Ile Thr Ala Val Ile Asp Trp Ser Glu Ala Met Phe Gly Asp
    210                 215                 220

Ser Gln Tyr Glu Val Ala Asn Ile Phe Phe Trp Arg Pro Trp Leu Ala
225                 230                 235                 240

Cys Met Glu Gln Gln Thr Arg Tyr Phe Glu Arg His Pro Glu Leu
                245                 250                 255

Ala Gly Ser Pro Arg Leu Arg Ala Tyr Met Leu Arg Ile Gly Leu Asp
            260                 265                 270

Gln Leu Tyr Gln Ser Leu Val Asp Gly Asn Phe Asp Asp Ala Ala Trp
        275                 280                 285

Ala Gln Gly Arg Cys Asp Ala Ile Val Arg Ser Gly Ala Gly Thr Val
    290                 295                 300

Gly Arg Thr Gln Ile Ala Arg Arg Ser Ala Ala Val Trp Thr Asp Gly
305                 310                 315                 320

Cys Val Glu Val Leu Ala Asp Ser Gly Asn Arg Arg Pro Ser Thr Arg
                325                 330                 335

Pro Arg Ala Lys Glu
            340

<210> SEQ ID NO 12
<211> LENGTH: 53
<212> TYPE: DNA
<213> ORGANISM: Artificial Sequence
<220> FEATURE:
<223> OTHER INFORMATION: Primer IRES5', synthetic sequence

<400> SEQUENCE: 12
caactcgagc ggccgccccc cccccctctc cctccccccc ccctaacgtt act         53

<210> SEQ ID NO 13
<211> LENGTH: 22
<212> TYPE: DNA
<213> ORGANISM: Artificial Sequence
<220> FEATURE:
<223> OTHER INFORMATION: Primer IRES3', synthetic sequence

<400> SEQUENCE: 13
caagaagctt ccagaggaac tg                                            22

<210> SEQ ID NO 14
<211> LENGTH: 30
<212> TYPE: DNA
<213> ORGANISM: Artificial Sequence
<220> FEATURE:
<223> OTHER INFORMATION: Primer mPGKP5', synthetic sequence

<400> SEQUENCE: 14
gcgagatctt accgggtagg ggaggcgctt                                    30

<210> SEQ ID NO 15
<211> LENGTH: 30
<212> TYPE: DNA
<213> ORGANISM: Artificial Sequence
<220> FEATURE:
```

<223> OTHER INFORMATION: Primer mPGKP3', synthetic sequence

<400> SEQUENCE: 15
gaggaattcg atgatcggtc gaaaggcccg                                      30

<210> SEQ ID NO 16
<211> LENGTH: 532
<212> TYPE: DNA
<213> ORGANISM: Artificial Sequence
<220> FEATURE:
<223> OTHER INFORMATION: mPGKp, synthetic sequence

<400> SEQUENCE: 16
gcgagatctt accgggtagg ggaggcgctt ttcccaaggc agtctggagc atgcgcttta     60
gcagccccgc tgggcacttg gcgctacaca agtggcctct ggcctcgcac acattccaca   120
tccaccggta ggcgccaacc ggctccgttc tttggtggcc ccttcgcgcc accttctact   180
cctcccctag tcaggaagtt cccccccgcc ccgcagctcg cgtcgtgcag gacgtgacaa   240
atggaagtag cacgtctcac tagtctcgtg cagatggaca gcaccgctga gcaatggaag   300
cgggtaggcc tttggggcag cggccaatag cagctttgct ccttcgcttt ctgggctcag   360
aggctgggaa gggtgggtc cggggcggg ctcaggggcg ggctcagggg cggggcgggc    420
gcccgaaggt cctccggagg cccggcattc tgcacgcttc aaaagcgcac gtctgccgcg   480
ctgttctcct cttcctcatc tccgggcctt tcgaccgatc atcgaattcc tc           532

<210> SEQ ID NO 17
<211> LENGTH: 36
<212> TYPE: DNA
<213> ORGANISM: Artificial Sequence
<220> FEATURE:
<223> OTHER INFORMATION: Primer GS5', synthetic sequence

<400> SEQUENCE: 17
aatatggcca caaccatggc gacctcagca agttcc                               36

<210> SEQ ID NO 18
<211> LENGTH: 38
<212> TYPE: DNA
<213> ORGANISM: Artificial Sequence
<220> FEATURE:
<223> OTHER INFORMATION: Primer GS3', synthetic sequence

<400> SEQUENCE: 18
ggaggatccc tcgagttagt ttttgtattg gaagggct                             38

<210> SEQ ID NO 19
<211> LENGTH: 28
<212> TYPE: DNA
<213> ORGANISM: Artificial Sequence
<220> FEATURE:
<223> OTHER INFORMATION: Primer puro5', synthetic sequence

<400> SEQUENCE: 19
gcttaagatg accgagtaca agcccacg                                        28

<210> SEQ ID NO 20
<211> LENGTH: 30
<212> TYPE: DNA
<213> ORGANISM: Artificial Sequence
<220> FEATURE:
<223> OTHER INFORMATION: Primer puro3', synthetic sequence

<400> SEQUENCE: 20

```
cccatcgtga tggtcaggca ccgggcttgc                                        30
```

<210> SEQ ID NO 21
<211> LENGTH: 620
<212> TYPE: DNA
<213> ORGANISM: Artificial Sequence
<220> FEATURE:
<223> OTHER INFORMATION: nucleic acid sequence containing puromycin
      resistance gene, synthetic sequence

<400> SEQUENCE: 21

```
gcttaagatg accgagtaca agcccacggt gcgcctcgcc acccgcgacg acgtccccag        60
ggccgtacgc accctcgccg ccgcgttcgc cgactacccc gccacgcgcc acaccgtcga       120
tccggaccgc cacatcgagc gggtcaccga gctgcaagaa ctcttcctca cgcgcgtcgg       180
gctcgacatc ggcaaggtgt gggtcgcgga cgacggcgcc gcggtggcgg tctggaccac       240
gccggagagc gtcgaagcgg gggcggtgtt cgccgagatc ggcccgcgca tggccgagtt       300
gagcggttcc cggctggccg cgcagcaaca gatggaaggc ctcctggcgc cgcaccggcc       360
caaggagccc cgcgtggttc ctggccaccg tcggcgtctcg cccgaccacc agggcaaggg       420
tctgggcagc gccgtcgtgc tccccggagt ggaggcggcc gagcgcgccg ggtgccccgc       480
cttcctggag acctccgcgc cccgcaacct ccccttctac gagcggctcg gcttcaccgt       540
caccgccgac gtcgaggtgc ccgaaggacc gcgcacctgg tgcatgaccc gcaagcccgg       600
tgcctgacca tcacgatggg                                                  620
```

<210> SEQ ID NO 22
<211> LENGTH: 199
<212> TYPE: PRT
<213> ORGANISM: Artificial Sequence
<220> FEATURE:
<223> OTHER INFORMATION: amino acid sequence corresponding to puromycin
      resistance gene

<400> SEQUENCE: 22

```
Met Thr Glu Tyr Lys Pro Thr Val Arg Leu Ala Thr Arg Asp Asp Val
1               5                   10                  15

Pro Arg Ala Val Arg Thr Leu Ala Ala Ala Phe Ala Asp Tyr Pro Ala
            20                  25                  30

Thr Arg His Thr Val Asp Pro Asp Arg His Ile Glu Arg Val Thr Glu
        35                  40                  45

Leu Gln Glu Leu Phe Leu Thr Arg Val Gly Leu Asp Ile Gly Lys Val
    50                  55                  60

Trp Val Ala Asp Asp Gly Ala Ala Val Ala Val Trp Thr Thr Pro Glu
65                  70                  75                  80

Ser Val Glu Ala Gly Ala Val Phe Ala Glu Ile Gly Pro Arg Met Ala
                85                  90                  95

Glu Leu Ser Gly Ser Arg Leu Ala Ala Gln Gln Gln Met Glu Gly Leu
            100                 105                 110

Leu Ala Pro His Arg Pro Lys Glu Pro Ala Trp Phe Leu Ala Thr Val
        115                 120                 125

Gly Val Ser Pro Asp His Gln Gly Lys Gly Leu Gly Ser Ala Val Val
    130                 135                 140

Leu Pro Gly Val Glu Ala Ala Glu Arg Ala Gly Val Pro Ala Phe Leu
145                 150                 155                 160

Glu Thr Ser Ala Pro Arg Asn Leu Pro Phe Tyr Glu Arg Leu Gly Phe
                165                 170                 175
```

```
Thr Val Thr Ala Asp Val Glu Val Pro Glu Gly Pro Arg Thr Trp Cys
            180                 185                 190

Met Thr Arg Lys Pro Gly Ala
        195

<210> SEQ ID NO 23
<211> LENGTH: 44
<212> TYPE: DNA
<213> ORGANISM: Artificial Sequence
<220> FEATURE:
<223> OTHER INFORMATION: Primer SV40polyA5', synthetic sequence

<400> SEQUENCE: 23
caacaagcgg ccgccctcga gttccctta gtgagggtta atgc                    44

<210> SEQ ID NO 24
<211> LENGTH: 24
<212> TYPE: DNA
<213> ORGANISM: Artificial Sequence
<220> FEATURE:
<223> OTHER INFORMATION: Primer SV40polyA3', synthetic sequence

<400> SEQUENCE: 24
cccctgaacc tgaaacataa aatg                                         24

<210> SEQ ID NO 25
<211> LENGTH: 25
<212> TYPE: DNA
<213> ORGANISM: Artificial Sequence
<220> FEATURE:
<223> OTHER INFORMATION: Primer mIRES-GS5', synthetic sequence

<400> SEQUENCE: 25
acacgatgat aagcttgcca caacc                                        25

<210> SEQ ID NO 26
<211> LENGTH: 21
<212> TYPE: DNA
<213> ORGANISM: Artificial Sequence
<220> FEATURE:
<223> OTHER INFORMATION: Primer mIRES-GS3', synthetic sequence

<400> SEQUENCE: 26
ctccacgata tccctgccat a                                            21

<210> SEQ ID NO 27
<211> LENGTH: 776
<212> TYPE: PRT
<213> ORGANISM: Artificial Sequence
<220> FEATURE:
<223> OTHER INFORMATION: amino acid sequence of HSA-22K hGH

<400> SEQUENCE: 27

Asp Ala His Lys Ser Glu Val Ala His Arg Phe Lys Asp Leu Gly Glu
1               5                   10                  15

Glu Asn Phe Lys Ala Leu Val Leu Ile Ala Phe Ala Gln Tyr Leu Gln
            20                  25                  30

Gln Cys Pro Phe Glu Asp His Val Lys Leu Val Asn Glu Val Thr Glu
        35                  40                  45

Phe Ala Lys Thr Cys Val Ala Asp Glu Ser Ala Glu Asn Cys Asp Lys
    50                  55                  60

Ser Leu His Thr Leu Phe Gly Asp Lys Leu Cys Thr Val Ala Thr Leu
65                  70                  75                  80
```

```
Arg Glu Thr Tyr Gly Glu Met Ala Asp Cys Cys Ala Lys Gln Glu Pro
                85                  90                  95

Glu Arg Asn Glu Cys Phe Leu Gln His Lys Asp Asp Asn Pro Asn Leu
            100                 105                 110

Pro Arg Leu Val Arg Pro Glu Val Asp Val Met Cys Thr Ala Phe His
        115                 120                 125

Asp Asn Glu Glu Thr Phe Leu Lys Lys Tyr Leu Tyr Glu Ile Ala Arg
130                 135                 140

Arg His Pro Tyr Phe Tyr Ala Pro Glu Leu Leu Phe Phe Ala Lys Arg
145                 150                 155                 160

Tyr Lys Ala Ala Phe Thr Glu Cys Cys Gln Ala Ala Asp Lys Ala Ala
                165                 170                 175

Cys Leu Leu Pro Lys Leu Asp Glu Leu Arg Asp Glu Gly Lys Ala Ser
            180                 185                 190

Ser Ala Lys Gln Arg Leu Lys Cys Ala Ser Leu Gln Lys Phe Gly Glu
        195                 200                 205

Arg Ala Phe Lys Ala Trp Ala Val Ala Arg Leu Ser Gln Arg Phe Pro
210                 215                 220

Lys Ala Glu Phe Ala Glu Val Ser Lys Leu Val Thr Asp Leu Thr Lys
225                 230                 235                 240

Val His Thr Glu Cys Cys His Gly Asp Leu Leu Glu Cys Ala Asp Asp
                245                 250                 255

Arg Ala Asp Leu Ala Lys Tyr Ile Cys Glu Asn Gln Asp Ser Ile Ser
            260                 265                 270

Ser Lys Leu Lys Glu Cys Cys Glu Lys Pro Leu Leu Glu Lys Ser His
        275                 280                 285

Cys Ile Ala Glu Val Glu Asn Asp Glu Met Pro Ala Asp Leu Pro Ser
290                 295                 300

Leu Ala Ala Asp Phe Val Glu Ser Lys Asp Val Cys Lys Asn Tyr Ala
305                 310                 315                 320

Glu Ala Lys Asp Val Phe Leu Gly Met Phe Leu Tyr Glu Tyr Ala Arg
                325                 330                 335

Arg His Pro Asp Tyr Ser Val Val Leu Leu Leu Arg Leu Ala Lys Thr
            340                 345                 350

Tyr Glu Thr Thr Leu Glu Lys Cys Cys Ala Ala Ala Asp Pro His Glu
        355                 360                 365

Cys Tyr Ala Lys Val Phe Asp Glu Phe Lys Pro Leu Val Glu Glu Pro
370                 375                 380

Gln Asn Leu Ile Lys Gln Asn Cys Glu Leu Phe Glu Gln Leu Gly Glu
385                 390                 395                 400

Tyr Lys Phe Gln Asn Ala Leu Leu Val Arg Tyr Thr Lys Lys Val Pro
                405                 410                 415

Gln Val Ser Thr Pro Thr Leu Val Glu Val Ser Arg Asn Leu Gly Lys
            420                 425                 430

Val Gly Ser Lys Cys Cys Lys His Pro Glu Ala Lys Arg Met Pro Cys
        435                 440                 445

Ala Glu Asp Tyr Leu Ser Val Val Leu Asn Gln Leu Cys Val Leu His
450                 455                 460

Glu Lys Thr Pro Val Ser Asp Arg Val Thr Lys Cys Cys Thr Glu Ser
465                 470                 475                 480

Leu Val Asn Arg Arg Pro Cys Phe Ser Ala Leu Glu Val Asp Glu Thr
                485                 490                 495
```

-continued

```
Tyr Val Pro Lys Glu Phe Asn Ala Glu Thr Phe Thr Phe His Ala Asp
            500                 505                 510

Ile Cys Thr Leu Ser Glu Lys Glu Arg Gln Ile Lys Lys Gln Thr Ala
        515                 520                 525
Leu Val Glu Leu Val Lys His Lys Pro Lys Ala Thr Lys Glu Gln Leu
    530                 535                 540
Lys Ala Val Met Asp Asp Phe Ala Ala Phe Val Glu Lys Cys Cys Lys
545                 550                 555                 560

Ala Asp Asp Lys Glu Thr Cys Phe Ala Glu Glu Gly Lys Lys Leu Val
                565                 570                 575
Ala Ala Ser Gln Ala Ala Leu Gly Leu Phe Pro Thr Ile Pro Leu Ser
            580                 585                 590
Arg Leu Phe Asp Asn Ala Met Leu Arg Ala His Arg Leu His Gln Leu
        595                 600                 605
Ala Phe Asp Thr Tyr Gln Glu Phe Glu Glu Ala Tyr Ile Pro Lys Glu
    610                 615                 620
Gln Lys Tyr Ser Phe Leu Gln Asn Pro Gln Thr Ser Leu Cys Phe Ser
625                 630                 635                 640
Glu Ser Ile Pro Thr Pro Ser Asn Arg Glu Glu Thr Gln Gln Lys Ser
                645                 650                 655
Asn Leu Glu Leu Leu Arg Ile Ser Leu Leu Leu Ile Gln Ser Trp Leu
            660                 665                 670
Glu Pro Val Gln Phe Leu Arg Ser Val Phe Ala Asn Ser Leu Val Tyr
        675                 680                 685
Gly Ala Ser Asp Ser Asn Val Tyr Asp Leu Leu Lys Asp Leu Glu Glu
    690                 695                 700
Gly Ile Gln Thr Leu Met Gly Arg Leu Glu Asp Gly Ser Pro Arg Thr
705                 710                 715                 720
Gly Gln Ile Phe Lys Gln Thr Tyr Ser Lys Phe Asp Thr Asn Ser His
                725                 730                 735
Asn Asp Asp Ala Leu Leu Lys Asn Tyr Gly Leu Leu Tyr Cys Phe Arg
            740                 745                 750
Lys Asp Met Asp Lys Val Glu Thr Phe Leu Arg Ile Val Gln Cys Arg
        755                 760                 765
Ser Val Glu Gly Ser Cys Gly Phe
    770                 775
```

<210> SEQ ID NO 28
<211> LENGTH: 2421
<212> TYPE: DNA
<213> ORGANISM: Artificial Sequence
<220> FEATURE:
<223> OTHER INFORMATION: nucleic acid sequence containing HSA-22K hGH gene, synthetic sequence

<400> SEQUENCE: 28

```
acgcgtcacc atgaagtggg taacctttat ttcccttctt tttctcttta gctcggctta      60
ttccaggggt gtgtttcgtc gagatgcaca caagagtgag gttgctcatc ggtttaaaga     120
tttgggagaa gaaaatttca aagccttggt gttgattgcc tttgctcagt atcttcagca     180
gtgtccattt gaagatcatg taaaattagt gaatgaagta actgaatttg caaaaacatg     240
tgttgctgat gagtcagctg aaaattgtga caaatcactt catacccttt ttggagacaa     300
attatgcaca gttgcaactc ttcgtgaaac ctatggtgaa atggctgact gctgtgcaaa     360
acaagaacct gagagaaatg aatgcttctt gcaacacaaa gatgacaacc caaacctccc     420
```

-continued

```
ccgattggtg agaccagagg ttgatgtgat gtgcactgct tttcatgaca atgaagagac      480
attttttgaaa aaatacttat atgaaattgc cagaagacat ccttactttt atgccccgga     540
actccttttc tttgctaaaa ggtataaagc tgcttttaca gaatgttgcc aagctgctga      600
taaagctgcc tgcctgttgc caaagctcga tgaacttcgg gatgaaggga aggcttcgtc      660
tgccaaacag agactcaagt gtgccagtct ccaaaaattt ggagaaagag ctttcaaagc      720
atgggcagta gctcgcctga gccagagatt tcccaaagct gagtttgcag aagtttccaa      780
gttagtgaca gatcttacca agtccacac ggaatgctgc catggagatc tgcttgaatg       840
tgctgatgac agggcggacc ttgccaagta tatctgtgaa atcaagatt cgatctccag       900
taaactgaag gaatgctgtg aaaaacctct gttggaaaaa tcccactgca ttgccgaagt      960
ggaaaatgat gagatgcctg ctgacttgcc ttcattagct gctgattttg ttgaaagtaa     1020
ggatgtttgc aaaaactatg ctgaggcaaa ggatgtcttc ctgggcatgt ttttgtatga     1080
atatgcaaga aggcatcctg attactctgt cgtgctgctg ctgagacttg ccaagacata     1140
tgaaaccact ctagagaagt gctgtgccgc tgcagatcct catgaatgct atgccaaagt     1200
gttcgatgaa tttaaacctc ttgtggaaga gcctcagaat ttaatcaaac aaaattgtga     1260
gcttttgag cagcttggag agtacaaatt ccagaatgcg ctattagttc gttacaccaa      1320
gaaagtaccc caagtgtcaa ctccaactct tgtagaggtc tcaagaaacc taggaaaagt     1380
gggcagcaaa tgttgtaaac atcctgaagc aaaaagaatg ccctgtgcag aagactatct     1440
atccgtggtc ctgaaccagt tatgtgtgtt gcatgagaaa acgccagtaa gtgacagagt     1500
caccaaatgc tgcacagaat ccttggtgaa caggcgacca tgcttttcag ctctggaagt     1560
cgatgaaaca tacgttccca aagagtttaa tgctgaaaca ttcaccttcc atgcagatat     1620
atgcacactt tctgagaagg agagacaaat caagaaacaa actgcacttg ttgagctcgt     1680
gaaacacaag cccaaggcaa caaagagca actgaaagct gttatggatg atttcgcagc     1740
ttttgtagag aagtgctgca aggctgacga taaggagacc tgctttgccg aggagggtaa    1800
aaaacttgtt gctgcaagtc aagctgcctt aggcttattc ccaaccattc ccttatccag     1860
gcttttttgac aacgctatgc tccgcgccca tcgtctgcac cagctggcct ttgacaccta    1920
ccaggagttt gaagaagcct atatcccaaa ggaacagaag tattcattcc tgcagaaccc    1980
ccagacctcc ctctgtttct cagagtctat tccgacaccc tccaacaggg aggaaacaca    2040
acagaaatcc aacctagagc tgctccgcat ctccctgctg ctcatccagt cgtggctgga    2100
gcccgtgcag ttcctcagga gtgtcttcgc caacagcctg gtgtacggcg cctctgacag    2160
caacgtctat gacctcctaa aggacctaga ggaaggcatc caaacgctga tggggaggct    2220
ggaagatggc agcccccgga ctgggcagat cttcaagcag acctacagca agttcgacac    2280
aaactcacac aacgatgacg cactactcaa gaactacggg ctgctctact gcttcaggaa    2340
ggacatggac aaggtcgaga cattcctgcg catcgtgcag tgccgctctg tggagggcag    2400
ctgtggcttc taagcggccg c                                              2421
```

<210> SEQ ID NO 29
<211> LENGTH: 761
<212> TYPE: PRT
<213> ORGANISM: Artificial Sequence
<220> FEATURE:
<223> OTHER INFORMATION: amino acid sequence of HSA-20K hGH

<400> SEQUENCE: 29

Asp Ala His Lys Ser Glu Val Ala His Arg Phe Lys Asp Leu Gly Glu

-continued

```
1               5                   10                  15
Glu Asn Phe Lys Ala Leu Val Leu Ile Ala Phe Ala Gln Tyr Leu Gln
                20                  25                  30
Gln Cys Pro Phe Glu Asp His Val Lys Leu Val Asn Glu Val Thr Glu
                35                  40                  45
Phe Ala Lys Thr Cys Val Ala Asp Glu Ser Ala Glu Asn Cys Asp Lys
                50                  55                  60
Ser Leu His Thr Leu Phe Gly Asp Lys Leu Cys Thr Val Ala Thr Leu
 65                  70                  75                  80
Arg Glu Thr Tyr Gly Glu Met Ala Asp Cys Cys Ala Lys Gln Glu Pro
                85                  90                  95
Glu Arg Asn Glu Cys Phe Leu Gln His Lys Asp Asp Asn Pro Asn Leu
                100                 105                 110
Pro Arg Leu Val Arg Pro Glu Val Asp Val Met Cys Thr Ala Phe His
                115                 120                 125
Asp Asn Glu Glu Thr Phe Leu Lys Lys Tyr Leu Tyr Glu Ile Ala Arg
                130                 135                 140
Arg His Pro Tyr Phe Tyr Ala Pro Glu Leu Leu Phe Phe Ala Lys Arg
145                 150                 155                 160
Tyr Lys Ala Ala Phe Thr Glu Cys Cys Gln Ala Ala Asp Lys Ala Ala
                165                 170                 175
Cys Leu Leu Pro Lys Leu Asp Glu Leu Arg Asp Glu Gly Lys Ala Ser
                180                 185                 190
Ser Ala Lys Gln Arg Leu Lys Cys Ala Ser Leu Gln Lys Phe Gly Glu
                195                 200                 205
Arg Ala Phe Lys Ala Trp Ala Val Ala Arg Leu Ser Gln Arg Phe Pro
                210                 215                 220
Lys Ala Glu Phe Ala Glu Val Ser Lys Leu Val Thr Asp Leu Thr Lys
225                 230                 235                 240
Val His Thr Glu Cys Cys His Gly Asp Leu Leu Glu Cys Ala Asp Asp
                245                 250                 255
Arg Ala Asp Leu Ala Lys Tyr Ile Cys Glu Asn Gln Asp Ser Ile Ser
                260                 265                 270
Ser Lys Leu Lys Glu Cys Cys Glu Lys Pro Leu Leu Glu Lys Ser His
                275                 280                 285
Cys Ile Ala Glu Val Glu Asn Asp Glu Met Pro Ala Asp Leu Pro Ser
                290                 295                 300
Leu Ala Ala Asp Phe Val Glu Ser Lys Asp Val Cys Lys Asn Tyr Ala
305                 310                 315                 320
Glu Ala Lys Asp Val Phe Leu Gly Met Phe Leu Tyr Glu Tyr Ala Arg
                325                 330                 335
Arg His Pro Asp Tyr Ser Val Val Leu Leu Arg Leu Ala Lys Thr
                340                 345                 350
Tyr Glu Thr Thr Leu Glu Lys Cys Cys Ala Ala Ala Asp Pro His Glu
                355                 360                 365
Cys Tyr Ala Lys Val Phe Asp Glu Phe Lys Pro Leu Val Glu Glu Pro
                370                 375                 380
Gln Asn Leu Ile Lys Gln Asn Cys Glu Leu Phe Glu Gln Leu Gly Glu
385                 390                 395                 400
Tyr Lys Phe Gln Asn Ala Leu Leu Val Arg Tyr Thr Lys Lys Val Pro
                405                 410                 415
Gln Val Ser Thr Pro Thr Leu Val Glu Val Ser Arg Asn Leu Gly Lys
                420                 425                 430
```

Val Gly Ser Lys Cys Cys Lys His Pro Glu Ala Lys Arg Met Pro Cys
        435                 440                 445
Ala Glu Asp Tyr Leu Ser Val Leu Asn Gln Leu Cys Val Leu His
450                 455                 460
Glu Lys Thr Pro Val Ser Asp Arg Val Thr Lys Cys Cys Thr Glu Ser
465                 470                 475                 480
Leu Val Asn Arg Arg Pro Cys Phe Ser Ala Leu Glu Val Asp Glu Thr
                485                 490                 495
Tyr Val Pro Lys Glu Phe Asn Ala Glu Thr Phe Thr Phe His Ala Asp
                500                 505                 510
Ile Cys Thr Leu Ser Glu Lys Glu Arg Gln Ile Lys Lys Gln Thr Ala
                515                 520                 525
Leu Val Glu Leu Val Lys His Lys Pro Lys Ala Thr Lys Glu Gln Leu
530                 535                 540
Lys Ala Val Met Asp Asp Phe Ala Ala Phe Val Glu Lys Cys Cys Lys
545                 550                 555                 560
Ala Asp Asp Lys Glu Thr Cys Phe Ala Glu Glu Gly Lys Lys Leu Val
                565                 570                 575
Ala Ala Ser Gln Ala Ala Leu Gly Leu Phe Pro Thr Ile Pro Leu Ser
                580                 585                 590
Arg Leu Phe Asp Asn Ala Met Leu Arg Ala His Arg Leu His Gln Leu
                595                 600                 605
Ala Phe Asp Thr Tyr Gln Glu Phe Asn Pro Gln Thr Ser Leu Cys Phe
                610                 615                 620
Ser Glu Ser Ile Pro Thr Pro Ser Asn Arg Glu Glu Thr Gln Gln Lys
625                 630                 635                 640
Ser Asn Leu Glu Leu Leu Arg Ile Ser Leu Leu Leu Ile Gln Ser Trp
                645                 650                 655
Leu Glu Pro Val Gln Phe Leu Arg Ser Val Phe Ala Asn Ser Leu Val
                660                 665                 670
Tyr Gly Ala Ser Asp Ser Asn Val Tyr Asp Leu Leu Lys Asp Leu Glu
                675                 680                 685
Glu Gly Ile Gln Thr Leu Met Gly Arg Leu Glu Asp Gly Ser Pro Arg
                690                 695                 700
Thr Gly Gln Ile Phe Lys Gln Thr Tyr Ser Lys Phe Asp Thr Asn Ser
705                 710                 715                 720
His Asn Asp Asp Ala Leu Leu Lys Asn Tyr Gly Leu Leu Tyr Cys Phe
                725                 730                 735
Arg Lys Asp Met Asp Lys Val Glu Thr Phe Leu Arg Ile Val Gln Cys
                740                 745                 750
Arg Ser Val Glu Gly Ser Cys Gly Phe
                755                 760

<210> SEQ ID NO 30
<211> LENGTH: 56
<212> TYPE: DNA
<213> ORGANISM: Artificial Sequence
<220> FEATURE:
<223> OTHER INFORMATION: Primer YA055, synthetic sequence

<400> SEQUENCE: 30
cagctggcct ttgacaccta ccaggagttt aaccccccaga cctccctctg tttctc          56

<210> SEQ ID NO 31
<211> LENGTH: 40

```
<212> TYPE: DNA
<213> ORGANISM: Artificial Sequence
<220> FEATURE:
<223> OTHER INFORMATION: Primer YA056, synthetic sequence

<400> SEQUENCE: 31
tttggcggcc gcttagaagc cacagctgcc ctccacagag                          40

<210> SEQ ID NO 32
<211> LENGTH: 47
<212> TYPE: DNA
<213> ORGANISM: Artificial Sequence
<220> FEATURE:
<223> OTHER INFORMATION: Primer YA036, synthetic sequence

<400> SEQUENCE: 32
ccggtcgaca cgcgtcgcca ccatgaagtg ggtaaccttt atttccc                  47

<210> SEQ ID NO 33
<211> LENGTH: 2379
<212> TYPE: DNA
<213> ORGANISM: Artificial Sequence
<220> FEATURE:
<223> OTHER INFORMATION: nucleic acid sequence containing HSA-20K hGH
      gene, synthetic sequence

<400> SEQUENCE: 33
acgcgtcgcc accatgaagt gggtaacctt tatttccctt cttttctct ttagctcggc      60 ttattccagg ggtgtgtttc gtcgagatgc acacaagagt gaggttgctc atcggtttaa    120
agatttggga agagaaaatt tcaaagcctt ggtgttgatt gcctttgctc agtatcttca    180
gcagtgtcca tttgaagatc atgtaaaatt agtgaatgaa gtaactgaat tgcaaaaac    240 atgtgttgct gatgagtcag ctgaaaattg tgacaaatca cttcataccc tttttggaga    300
caaattatgc acagttgcaa ctcttcgtga aacctatggt gaaatggctg actgctgtgc    360
aaaacaagaa cctgagagaa atgaatgctt cttgcaacac aaagatgaca acccaaacct    420
cccccgattg gtgagaccag aggttgatgt gatgtgcact gcttttcatg acaatgaaga    480 gacattttg aaaaaatact tatatgaaat tgccagaaga catccttact tttatgcccc    540
ggaactcctt ttctttgcta aaaggtataa agctgctttt acagaatgtt gccaagctgc    600
tgataaagct gcctgcctgt tgccaaagct cgatgaactt cgggatgaag gaaggcttc    660 gtctgccaaa cagagactca gtgtgccag tctccaaaaa tttggagaaa gagctttcaa    720
agcatgggca gtagctcgcc tgagccagag atttcccaaa gctgagtttg cagaagtttc    780
caagttagtg acagatctta ccaaagtcca cacggaatgc tgccatggag atctgcttga    840
atgtgctgat gacagggcgg accttgccaa gtatatctgt gaaaatcaag attcgatctc    900
cagtaaactg aaggaatgct gtgaaaaacc tctgttggaa aaatcccact gcattgccga    960
agtggaaaat gatgagatgc ctgctgactt gccttcatta gctgctgatt ttgttgaaag   1020
taaggatgtt tgcaaaaact atgctgaggc aaaggatgtc ttcctgggca tgttttttgta  1080 tgaatatgca agaaggcatc ctgattactc tgtcgtgctg ctgctgagac ttgccaagac   1140
atatgaaacc actctagaga agtgctgtgc cgctgcagat cctcatgaat gctatgccaa   1200
agtgttcgat gaatttaaac ctcttgtgga agagcctcag aatttaatca acaaaaattg   1260
tgagcttttt gagcagcttg gagagtacaa attccagaat gcgctattag ttcgttacac   1320
caagaaagta ccccaagtgt caactccaac tcttgtagag gtctcaagaa acctaggaaa   1380
agtgggcagc aaatgttgta aacatcctga agcaaaaaga atgccctgtg cagaagacta   1440
```

```
tctatccgtg gtcctgaacc agttatgtgt gttgcatgag aaaacgccag taagtgacag   1500
agtcaccaaa tgctgcacag aatccttggt gaacaggcga ccatgctttt cagctctgga   1560
agtcgatgaa acatacgttc ccaaagagtt taatgctgaa acattcaccct tccatgcaga   1620 tatatgcaca ctttctgaga aggagagaca aatcaagaaa caaactgcac ttgttgagct   1680
cgtgaaacac aagcccaagg caacaaaaga gcaactgaaa gctgttatgg atgatttcgc   1740
agcttttgta gagaagtgct gcaaggctga cgataaggag acctgctttg ccgaggaggg   1800
taaaaaactt gttgctgcaa gtcaagctgc cttaggctta ttcccaacca ttcccttatc   1860
caggcttttt gacaacgcta tgctccgcgc ccatcgtctg caccagctgg cctttgacac   1920
ctaccaggag tttaaccccc agacctccct ctgtttctca gagtctattc cgacaccctc   1980 caacaggag gaaacacaac agaaatccaa cctagagctg ctccgcatct ccctgctgct   2040
catccagtcg tggctggagc ccgtgcagtt cctcaggagt gtcttcgcca acagcctggt   2100
gtacggcgcc tctgacagca cgtctatga cctcctaaag gacctagagg aaggcatcca   2160
aacgctgatg gggaggctgg aagatggcag cccccggact gggcagatct tcaagcagac   2220
ctacagcaag ttcgacacaa actcacacaa cgatgacgca ctactcaaga actacgggct   2280
gctctactgc ttcaggaagg acatggacaa ggtcgagaca ttcctgcgca tcgtgcagtg   2340
ccgctctgtg gagggcagct gtggcttcta agcggccgc                          2379

<210> SEQ ID NO 34
<211> LENGTH: 56
<212> TYPE: DNA
<213> ORGANISM: Artificial Sequence
<220> FEATURE:
<223> OTHER INFORMATION: Primer YA065, synthetic sequence

<400> SEQUENCE: 34
tccggatccg cctccaccag agcctcctcc acctaagcct aaggcagctt gacttg       56

<210> SEQ ID NO 35
<211> LENGTH: 60
<212> TYPE: DNA
<213> ORGANISM: Artificial Sequence
<220> FEATURE:
<223> OTHER INFORMATION: Primer YA066, synthetic sequence

<400> SEQUENCE: 35
ggcggatccg gaggcggagg gtcgggtgga ggaggctctt tcccaaccat tcccttatcc   60

<210> SEQ ID NO 36
<211> LENGTH: 781
<212> TYPE: PRT
<213> ORGANISM: Artificial Sequence
<220> FEATURE:
<223> OTHER INFORMATION: amino acid sequence of HSA-[linker]-20K hGH

<400> SEQUENCE: 36

Asp Ala His Lys Ser Glu Val Ala His Arg Phe Lys Asp Leu Gly Glu
1               5                   10                  15

Glu Asn Phe Lys Ala Leu Val Leu Ile Ala Phe Ala Gln Tyr Leu Gln
                20                  25                  30

Gln Cys Pro Phe Glu Asp His Val Lys Leu Val Asn Glu Val Thr Glu
            35                  40                  45

Phe Ala Lys Thr Cys Val Ala Asp Glu Ser Ala Glu Asn Cys Asp Lys
        50                  55                  60
```

-continued

```
Ser Leu His Thr Leu Phe Gly Asp Lys Leu Cys Thr Val Ala Thr Leu
 65                  70                  75                  80

Arg Glu Thr Tyr Gly Glu Met Ala Asp Cys Cys Ala Lys Gln Glu Pro
                 85                  90                  95

Glu Arg Asn Glu Cys Phe Leu Gln His Lys Asp Asp Asn Pro Asn Leu
            100                 105                 110

Pro Arg Leu Val Arg Pro Glu Val Asp Val Met Cys Thr Ala Phe His
        115                 120                 125

Asp Asn Glu Glu Thr Phe Leu Lys Lys Tyr Leu Tyr Glu Ile Ala Arg
    130                 135                 140

Arg His Pro Tyr Phe Tyr Ala Pro Glu Leu Leu Phe Phe Ala Lys Arg
145                 150                 155                 160

Tyr Lys Ala Ala Phe Thr Glu Cys Cys Gln Ala Ala Asp Lys Ala Ala
                165                 170                 175

Cys Leu Leu Pro Lys Leu Asp Glu Leu Arg Asp Glu Gly Lys Ala Ser
            180                 185                 190

Ser Ala Lys Gln Arg Leu Lys Cys Ala Ser Leu Gln Lys Phe Gly Glu
        195                 200                 205

Arg Ala Phe Lys Ala Trp Ala Val Ala Arg Leu Ser Gln Arg Phe Pro
    210                 215                 220

Lys Ala Glu Phe Ala Glu Val Ser Lys Leu Val Thr Asp Leu Thr Lys
225                 230                 235                 240

Val His Thr Glu Cys Cys His Gly Asp Leu Leu Glu Cys Ala Asp Asp
                245                 250                 255

Arg Ala Asp Leu Ala Lys Tyr Ile Cys Glu Asn Gln Asp Ser Ile Ser
            260                 265                 270

Ser Lys Leu Lys Glu Cys Cys Glu Lys Pro Leu Leu Glu Lys Ser His
        275                 280                 285

Cys Ile Ala Glu Val Glu Asn Asp Glu Met Pro Ala Asp Leu Pro Ser
    290                 295                 300

Leu Ala Ala Asp Phe Val Glu Ser Lys Asp Val Cys Lys Asn Tyr Ala
305                 310                 315                 320

Glu Ala Lys Asp Val Phe Leu Gly Met Phe Leu Tyr Glu Tyr Ala Arg
                325                 330                 335

Arg His Pro Asp Tyr Ser Val Val Leu Leu Leu Arg Leu Ala Lys Thr
            340                 345                 350

Tyr Glu Thr Thr Leu Glu Lys Cys Cys Ala Ala Ala Asp Pro His Glu
        355                 360                 365

Cys Tyr Ala Lys Val Phe Asp Glu Phe Lys Pro Leu Val Glu Glu Pro
    370                 375                 380

Gln Asn Leu Ile Lys Gln Asn Cys Glu Leu Phe Glu Gln Leu Gly Glu
385                 390                 395                 400

Tyr Lys Phe Gln Asn Ala Leu Leu Val Arg Tyr Thr Lys Lys Val Pro
                405                 410                 415

Gln Val Ser Thr Pro Thr Leu Val Glu Val Ser Arg Asn Leu Gly Lys
            420                 425                 430

Val Gly Ser Lys Cys Cys Lys His Pro Glu Ala Lys Arg Met Pro Cys
        435                 440                 445

Ala Glu Asp Tyr Leu Ser Val Val Leu Asn Gln Leu Cys Val Leu His
    450                 455                 460

Glu Lys Thr Pro Val Ser Asp Arg Val Thr Lys Cys Cys Thr Glu Ser
465                 470                 475                 480

Leu Val Asn Arg Arg Pro Cys Phe Ser Ala Leu Glu Val Asp Glu Thr
```

```
            485                 490                 495
Tyr Val Pro Lys Glu Phe Asn Ala Glu Thr Phe Thr Phe His Ala Asp
            500                 505                 510

Ile Cys Thr Leu Ser Glu Lys Glu Arg Gln Ile Lys Lys Gln Thr Ala
            515                 520                 525

Leu Val Glu Leu Val Lys His Lys Pro Lys Ala Thr Lys Glu Gln Leu
    530                 535                 540

Lys Ala Val Met Asp Asp Phe Ala Ala Phe Val Glu Lys Cys Cys Lys
545                 550                 555                 560

Ala Asp Asp Lys Glu Thr Cys Phe Ala Glu Glu Gly Lys Lys Leu Val
                565                 570                 575

Ala Ala Ser Gln Ala Ala Leu Gly Leu Gly Gly Gly Ser Gly Gly
            580                 585                 590

Gly Gly Ser Gly Gly Gly Ser Gly Gly Gly Ser Phe Pro Thr
    595                 600                 605

Ile Pro Leu Ser Arg Leu Phe Asp Asn Ala Met Leu Arg Ala His Arg
    610                 615                 620

Leu His Gln Leu Ala Phe Asp Thr Tyr Gln Glu Phe Asn Pro Gln Thr
625                 630                 635                 640

Ser Leu Cys Phe Ser Glu Ser Ile Pro Thr Pro Ser Asn Arg Glu Glu
                645                 650                 655

Thr Gln Gln Lys Ser Asn Leu Glu Leu Leu Arg Ile Ser Leu Leu Leu
            660                 665                 670

Ile Gln Ser Trp Leu Glu Pro Val Gln Phe Leu Arg Ser Val Phe Ala
            675                 680                 685

Asn Ser Leu Val Tyr Gly Ala Ser Asp Ser Asn Val Tyr Asp Leu Leu
            690                 695                 700

Lys Asp Leu Glu Glu Gly Ile Gln Thr Leu Met Gly Arg Leu Glu Asp
705                 710                 715                 720

Gly Ser Pro Arg Thr Gly Gln Ile Phe Lys Gln Thr Tyr Ser Lys Phe
                725                 730                 735

Asp Thr Asn Ser His Asn Asp Asp Ala Leu Leu Lys Asn Tyr Gly Leu
            740                 745                 750

Leu Tyr Cys Phe Arg Lys Asp Met Asp Lys Val Glu Thr Phe Leu Arg
            755                 760                 765

Ile Val Gln Cys Arg Ser Val Glu Gly Ser Cys Gly Phe
    770                 775                 780

<210> SEQ ID NO 37
<211> LENGTH: 2439
<212> TYPE: DNA
<213> ORGANISM: Artificial Sequence
<220> FEATURE:
<223> OTHER INFORMATION: nucleic acid sequence containing
      HSA-[linker]-20K hGH gene, synthetic sequence

<400> SEQUENCE: 37
acgcgtcgcc accatgaagt gggtaacctt tatttccctt cttttctct ttagctcggc      60 ttattccagg ggtgtgtttc gtcgagatgc acacaagagt gaggttgctc atcggtttaa    120
agatttggga agaaaaatt tcaaagccct tggtgttgat gcctttgctc agtatcttca    180
gcagtgtcca tttgaagatc atgtaaaatt agtgaatgaa gtaactgaat tgcaaaaac    240 atgtgttgct gatgagtcag ctgaaaattg tgacaaatca cttcataccc ttttggaga    300 caaattatgc acagttgcaa ctcttcgtga aacctatggt gaaatggctg actgctgtgc    360
```

```
aaaacaagaa cctgagagaa atgaatgctt cttgcaacac aaagatgaca acccaaacct      420
cccccgattg gtgagaccag aggttgatgt gatgtgcact gcttttcatg acaatgaaga      480
gacattttg aaaaaatact tatatgaaat tgccagaaga catccttact tttatgcccc       540
ggaactcctt ttctttgcta aaaggtataa agctgctttt acagaatgtt gccaagctgc      600
tgataaagct gcctgcctgt tgccaaagct cgatgaactt cgggatgaag ggaaggcttc      660
gtctgccaaa cagagactca agtgtgccag tctccaaaaa tttggagaaa gagcttcaa       720
agcatgggca gtagctcgcc tgagccagag atttcccaaa gctgagtttg cagaagtttc      780
caagttagtg acagatctta ccaaagtcca cacggaatgc tgccatggag atctgcttga      840
atgtgctgat gacagggcgg accttgccaa gtatatctgt gaaaatcaag attcgatctc      900
cagtaaactg aaggaatgct gtgaaaaacc tctgttggaa aaatcccact gcattgccga      960
agtggaaaat gatgagatgc ctgctgactt gccttcatta gctgctgatt tgttgaaag      1020
taaggatgtt tgcaaaaact atgctgaggc aaaggatgtc ttcctgggca tgttttttgta    1080
tgaatatgca agaaggcatc ctgattactc tgtcgtgctg ctgctgagac ttgccaagac      1140
atatgaaacc actctagaga agtgctgtgc cgctgcagat cctcatgaat gctatgccaa      1200
agtgttcgat gaatttaaac ctcttgtgga agagcctcag aatttaatca acaaaattg      1260
tgagcttttt gagcagcttg gagagtacaa attccagaat gcgctattag ttcgttacac      1320
caagaaagta ccccaagtgt caactccaac tcttgtagag gtctcaagaa acctaggaaa      1380
agtgggcagc aaatgttgta acatcctgag caaaaagga atgccctgtg cagaagacta      1440
tctatccgtg gtcctgaacc agttatgtgt gttgcatgag aaaacgccag taagtgacag      1500
agtcaccaaa tgctgcacag aatccttggt gaacaggcga ccatgctttt cagctctgga      1560
agtcgatgaa acatacgttc ccaaagagtt taatgctgaa acattcacct tccatgcaga      1620
tatatgcaca ctttctgaga aggagagaca aatcaagaaa caaactgcac ttgttgagct      1680
cgtgaaacac aagcccaagg caacaaaaga gcaactgaaa gctgttatgg atgatttcgc      1740
agcttttgta gagaagtgct gcaaggctga cgataaggag acctgctttg ccgaggaggg      1800
taaaaaactt gttgctgcaa gtcaagctgc cttaggctta ggtggaggag gctctggtgg      1860
aggcggatcc ggaggcggag ggtcgggtgg aggaggctct ttcccaacca ttcccttatc      1920
caggcttttt gacaacgcta tgctccgcgc ccatcgtctg caccagctgg cctttgacac      1980
ctaccaggag tttaacccc agacctccct ctgtttctca gagtctattc cgacaccctc       2040
caacagggag gaaacacaac agaaatccaa cctagagctg ctccgcatct ccctgctgct      2100
catccagtcg tggctggagc ccgtgcagtt cctcaggagt gtcttcgcca acagcctggt      2160
gtacggcgcc tctgacagca acgtctatga cctcctaaag gacctagagg aaggcatcca      2220
aacgctgatg gggaggctgg aagatggcag cccccggact gggcagatct tcaagcagac      2280
ctacagcaag ttcgacacaa actcacacaa cgatgacgca ctactcaaga actacgggct      2340
gctctactgc ttcaggaagg acatggacaa ggtcgagaca ttcctgcgca tcgtgcagtg      2400
ccgctctgtg gagggcagct gtggcttcta agcggccgc                             2439
```

<210> SEQ ID NO 38
<211> LENGTH: 792
<212> TYPE: DNA
<213> ORGANISM: Artificial Sequence
<220> FEATURE:
<223> OTHER INFORMATION: nucleic acid sequence coding synthetic hGHR ECD
      gene, synthetic sequence

<400> SEQUENCE: 38

```
atggacctgt ggcagctcct cctgaccctc gctctggctg gctcctccga tgccttctcc    60
ggctccgagg ccaccgctgc tatcctgagc agggctccct ggtcctgca gagcgtcaac    120
cctggcctga agaccaactc ctccaaagag cccaagttca caagtgcag gtccccgag     180
agggagacct tctcctgtca ttggaccgac gaggtgcacc acggcaccaa gaacctgggc   240
cccatccagc tcttctacac caggaggaac acccaagagt ggacacagga gtggaaggag   300
tgccccgatt acgtgtccgc cggcgagaac agctgctact caactcctc cttcacatcc    360
atctggattc cttattgcat caaactgacc tccaacggcg gcacagtgga tgagaagtgc   420
ttcagcgtcg acgagatcgt gcagcccgat ccccccatcg ctctgaactg gaccctgctg   480
aatgtgtccc tgaccggcat ccacgccgat attcaggtga ggtgggaggc tcccaggaac   540
gctgacatcc agaagggctg gatggtcctg gagtacgagc tgcagtacaa ggaggtcaac   600
gagaccaagt ggaaaatgat ggaccctatc ctgacaacat ccgtccctgt gtacagcctg   660
aaggtggaca aagagtacga ggtgagggtg aggagcaaac agcggaatag cggcaactac   720
ggagaattct ccgaggtgct gtatgtgacc ctgccccaga tgtcccagtt cacctgtgaa   780
gaggactttt ac                                                        792
```

<210> SEQ ID NO 39
<211> LENGTH: 42
<212> TYPE: DNA
<213> ORGANISM: Artificial Sequence
<220> FEATURE:
<223> OTHER INFORMATION: primer YA034, synthetic sequence

<400> SEQUENCE: 39

```
ccgacgcgtc gccaccatgg acctgtggca gctcctcctg ac                       42
```

<210> SEQ ID NO 40
<211> LENGTH: 67
<212> TYPE: DNA
<213> ORGANISM: Artificial Sequence
<220> FEATURE:
<223> OTHER INFORMATION: primer YA035, synthetic sequence

<400> SEQUENCE: 40

```
cactgttagc ccgaatattc cgaagatgat aattaggagc catgggaagt aaaagtcctc    60
ttcacag                                                              67
```

<210> SEQ ID NO 41
<211> LENGTH: 43
<212> TYPE: DNA
<213> ORGANISM: Artificial Sequence
<220> FEATURE:
<223> OTHER INFORMATION: primer K708, synthetic sequence

<400> SEQUENCE: 41

```
ccggtcgacc gccaccatgg atctctggca gctgctgttg acc                      43
```

<210> SEQ ID NO 42
<211> LENGTH: 39
<212> TYPE: DNA
<213> ORGANISM: Artificial Sequence
<220> FEATURE:
<223> OTHER INFORMATION: primer K709, synthetic sequence

<400> SEQUENCE: 42

```
tttggcggcc gcctaaggca tgattttgtt cagttggtc                           39
```

<210> SEQ ID NO 43
<211> LENGTH: 1917
<212> TYPE: DNA
<213> ORGANISM: Artificial Sequence
<220> FEATURE:
<223> OTHER INFORMATION: nucleic acid sequence coding synthetic hGHR gene, synthetic sequence

<400> SEQUENCE: 43

| | | | | | |
|---|---|---|---|---|---|
| atggacctgt | ggcagctcct | cctgaccctc | gctctggctg | ctcctccga | tgccttctcc | 60 |
| ggctccgagg | ccaccgctgc | tatcctgagc | agggctccct | ggtccctgca | gagcgtcaac | 120 |
| cctggcctga | agaccaactc | ctccaaagag | cccaagttca | caaagtgcag | gtcccccgag | 180 |
| agggagacct | tctcctgtca | ttggaccgac | gaggtgcacc | acggcaccaa | gaacctgggc | 240 |
| cccatccagc | tcttctacac | caggaggaac | acccaagagt | ggacacagga | gtggaaggag | 300 |
| tgccccgatt | acgtgtccgc | cggcgagaac | agctgctact | tcaactcctc | cttcacatcc | 360 |
| atctggattc | cttattgcat | caaactgacc | tccaacggcg | gcacagtgga | tgagaagtgc | 420 |
| ttcagcgtcg | acgagatcgt | gcagcccgat | cccccatcg | ctctgaactg | gaccctgctg | 480 |
| aatgtgtccc | tgaccggcat | ccacgccgat | attcaggtga | ggtgggaggc | tcccaggaac | 540 |
| gctgacatcc | agaagggctg | gatggtcctg | gagtacgagc | tgcagtacaa | ggaggtcaac | 600 |
| gagaccaagt | ggaaaatgat | ggaccctatc | ctgacaacat | ccgtccctgt | gtacagcctg | 660 |
| aaggtggaca | agagtacga | ggtgagggtg | aggagcaaac | agcggaatag | cggcaactac | 720 |
| ggagaattct | ccgaggtgct | gtatgtgacc | ctgccccaga | tgtccagtt | cacctgtgaa | 780 |
| gaggactttt | acttcccatg | gctcctaatt | atcatcttcg | gaatattcgg | ctaacagtg | 840 |
| atgctatttg | tattcttatt | ttctaaacag | caaaggatta | aatgctgat | ctgcccccca | 900 |
| gttccagttc | caaagattaa | aggaatcgat | ccagatctcc | tcaaggaagg | aaaattagag | 960 |
| gaggtgaaca | atcttagc | cattcatgat | agctataaac | ccgaattcca | cagtgatgac | 1020 |
| tcttgggttg | aatttattga | gctagatatt | gatgagccag | atgaaaagac | tgaggaatca | 1080 |
| gacacagaca | gacttctaag | cagtgaccat | gagaaatcac | atagtaacct | aggggtgaag | 1140 |
| gatggcgact | ctggacgtac | cagctgttgt | gaacctgaca | ttctggagac | tgatttcaat | 1200 |
| gccaatgaca | tacatgaggg | tacctcgag | gttgctcagc | cacagaggtt | aaagggggaa | 1260 |
| gcagatctct | tatgccttga | ccagaagaat | caaaataact | caccttatca | tgatgcttgc | 1320 |
| cctgctactc | agcagcccag | tgttatccaa | gcagagaaaa | acaaaccaca | accacttcct | 1380 |
| actgaaggag | ctgagtcaac | tcaccaagct | gcccatattc | agctaagcaa | tccaagttca | 1440 |
| ctgtcaaaca | tcgacttta | tgcccaggtg | agcgacatta | ccagcagg | tagtgtggtc | 1500 |
| ctttccccgg | gccaaaagaa | taaggcaggg | atgtcccaat | gtgacatgca | cccggaaatg | 1560 |
| gtctcactct | gccaagaaaa | cttccttatg | acaatgcct | acttctgtga | ggcagatgcc | 1620 |
| aaaaagtgca | tccctgtggc | tcctcacatc | aaggttgaat | cacacataca | gccaagctta | 1680 |
| aaccaagagg | acatttacat | caccacagaa | agccttacca | ctgctgctgg | gaggcctggg | 1740 |
| acaggagaac | atgttccagg | ttctgagatg | cctgtcccag | actatacctc | cattcatata | 1800 |
| gtacagtccc | cacagggcct | catactcaat | gcgactgcct | tgccccttgcc | tgacaaagag | 1860 |
| tttctctcat | catgtggcta | tgtgagcaca | gaccaactga | acaaaatcat | gccttag | 1917 |

<210> SEQ ID NO 44
<211> LENGTH: 43

-continued

<212> TYPE: DNA
<213> ORGANIZM: Artificial Sequence
<220> FEATURE:
<223> OTHER INFORMATION: primer YA001, synthetic sequence

<400> SEQUENCE: 44
ccggtcgacc gccaccatga aggaaaatgt ggcatctgca acc         43

<210> SEQ ID NO 45
<211> LENGTH: 39
<212> TYPE: DNA
<213> ORGANISM: Artificial Sequence
<220> FEATURE:
<223> OTHER INFORMATION: primer YA002, synthetic sequence

<400> SEQUENCE: 45
tttggcggcc gctcagtgaa aggagtgtgt aaaacatgc         39

<210> SEQ ID NO 46
<211> LENGTH: 586
<212> TYPE: PRT
<213> ORGANISM: Homo sapiens

<400> SEQUENCE: 46

```
Arg Asp Ala His Lys Ser Glu Val Ala His Arg Phe Lys Asp Leu Gly
  1               5                  10                  15
Glu Glu Asn Phe Lys Ala Leu Val Leu Ile Ala Phe Ala Gln Tyr Leu
              20                  25                  30
Gln Gln Cys Pro Phe Glu Asp His Val Lys Leu Val Asn Glu Val Thr
          35                  40                  45
Glu Phe Ala Lys Thr Cys Val Ala Asp Glu Ser Ala Glu Asn Cys Asp
      50                  55                  60
Lys Ser Leu His Thr Leu Phe Gly Asp Lys Leu Cys Thr Val Ala Thr
  65                  70                  75                  80
Leu Arg Glu Thr Tyr Gly Glu Met Ala Asp Cys Cys Ala Lys Gln Glu
                  85                  90                  95
Pro Glu Arg Asn Glu Cys Phe Leu Gln His Lys Asp Asp Asn Pro Asn
             100                 105                 110
Leu Pro Arg Leu Val Arg Pro Glu Val Asp Val Met Cys Thr Ala Phe
         115                 120                 125
His Asp Asn Glu Glu Thr Phe Leu Lys Lys Tyr Leu Tyr Glu Ile Ala
     130                 135                 140
Arg Arg His Pro Tyr Phe Tyr Ala Pro Glu Leu Leu Phe Phe Ala Lys
 145                 150                 155                 160
Arg Tyr Lys Ala Ala Phe Thr Glu Cys Cys Gln Ala Ala Asp Lys Ala
                 165                 170                 175
Ala Cys Leu Leu Pro Lys Leu Asp Glu Leu Arg Asp Glu Gly Lys Ala
             180                 185                 190
Ser Ser Ala Lys Gln Arg Leu Lys Cys Ala Ser Leu Gln Lys Phe Gly
         195                 200                 205
Glu Arg Ala Phe Lys Ala Trp Ala Val Ala Arg Leu Ser Gln Arg Phe
     210                 215                 220
Pro Lys Ala Glu Phe Ala Glu Val Ser Lys Leu Val Thr Asp Leu Thr
 225                 230                 235                 240
Lys Val His Thr Glu Cys Cys His Gly Asp Leu Leu Glu Cys Ala Asp
                 245                 250                 255
Asp Arg Ala Asp Leu Ala Lys Tyr Ile Cys Glu Asn Gln Asp Ser Ile
             260                 265                 270
```

```
Ser Ser Lys Leu Lys Glu Cys Cys Glu Lys Pro Leu Leu Glu Lys Ser
        275                 280                 285
His Cys Ile Ala Glu Val Glu Asn Asp Glu Met Pro Ala Asp Leu Pro
        290                 295                 300
Ser Leu Ala Ala Asp Phe Val Glu Ser Lys Asp Val Cys Lys Asn Tyr
305                 310                 315                 320
Thr Glu Ala Lys Asp Val Phe Leu Gly Met Phe Leu Tyr Glu Tyr Ala
                325                 330                 335
Arg Arg His Pro Asp Tyr Ser Val Val Leu Leu Leu Arg Leu Ala Lys
                340                 345                 350
Thr Tyr Glu Thr Thr Leu Glu Lys Cys Cys Ala Ala Ala Asp Pro His
            355                 360                 365
Glu Cys Tyr Ala Lys Val Phe Asp Glu Phe Lys Pro Leu Val Glu Glu
        370                 375                 380
Pro Gln Asn Leu Ile Lys Gln Asn Cys Glu Leu Phe Glu Gln Leu Gly
385                 390                 395                 400
Glu Tyr Lys Phe Gln Asn Ala Leu Leu Val Arg Tyr Thr Lys Lys Val
                405                 410                 415
Pro Gln Val Ser Thr Pro Thr Leu Val Glu Val Ser Arg Asn Leu Gly
                420                 425                 430
Lys Val Gly Ser Lys Cys Cys Lys His Pro Glu Ala Lys Arg Met Pro
            435                 440                 445
Cys Ala Glu Asp Tyr Leu Ser Val Val Leu Asn Gln Leu Cys Val Leu
        450                 455                 460
His Glu Lys Thr Pro Val Ser Asp Arg Val Thr Lys Cys Cys Thr Glu
465                 470                 475                 480
Ser Leu Val Asn Arg Arg Pro Cys Phe Ser Ala Leu Glu Val Asp Glu
                485                 490                 495
Thr Tyr Val Pro Lys Glu Phe Asn Ala Glu Thr Phe Thr Phe His Ala
                500                 505                 510
Asp Ile Cys Thr Leu Ser Glu Lys Glu Arg Gln Ile Lys Lys Gln Thr
            515                 520                 525
Ala Leu Val Glu Leu Val Lys His Lys Pro Lys Ala Thr Lys Glu Gln
        530                 535                 540
Leu Lys Ala Val Met Asp Asp Phe Ala Ala Phe Val Glu Lys Cys Cys
545                 550                 555                 560
Lys Ala Asp Asp Lys Glu Thr Cys Phe Ala Glu Glu Gly Lys Lys Leu
                565                 570                 575
Val Ala Ala Ser Gln Ala Ala Leu Gly Leu
                580                 585
```

SERUM ALBUMIN-20K GROWTH HORMONE FUSION PROTEIN

REFERENCE TO A SEQUENCE LISTING

In accordance with 37 CFR § 1.52(e) (5), the present specification makes reference to a Sequence Listing (submitted electronically as a .txt file named "516488US_ST25.txt". The .txt file was generated on Jun. 15, 2020 and is 62.2 kb in size. The entire contents of the Sequence Listing are herein incorporated by reference.

CROSS-REFERENCE TO RELATED APPLICATIONS

The present application is a continuation of International Application No. PCT/JP2017/009498, filed Mar. 9, 2017, which is based upon and claims the benefits of priority to Japanese Application No. 2016-049102, filed Mar. 14, 2016. The entire contents of these applications are incorporated herein by reference.

FIELD OF THE INVENTION

The present invention relates to a fusion protein in which serum albumin and 20K growth hormone are bound to one another, for example, relates to a pharmaceutical composition for treatment of short stature or the like including as an active ingredient a fusion protein in which the C-terminus of human serum albumin and the N-terminus of 20K human growth hormone are linked directly or via a linker sequence.

BACKGROUND ART

Human serum albumin (HSA) is a protein whose mature form consists of 585 amino acids. HSA is the most abundant component of plasma proteins and has a long half-life of 14 to 20 days in plasma. HSA has the function of transporting endogenous substances such as fatty acids and exogenous substances such as drugs contained in the blood by combining with them. Low molecular weight substances such as drugs are taken into various organs, and then metabolized or excreted. However, substances bound to HSA are generally not to be well taken into organs and become able to circulate in the blood for a longer period of time.

Human serum albumin (HSA) has been known to have several natural variants. Human serum albumin Redhill is one of them (Non-patent Documents 1 and 2). In comparison with the amino acid sequence of the common human serum albumin consisting of 585 amino acids as mentioned above, human serum albumin Redhill differs in that alanine as the 320th amino acid residue from the N-terminus is replaced with threonine, and that one arginine residue is added to the N-terminus, it thus consists of 586 amino acids. This replacement of alanine with threonine give rise to a sequence Asn-Tyr-Thr within the amino acid sequence of albumin Redhill, and this Asn (asparagine) residue in that sequence receives N-glycosylation. Thus, the molecular weight of albumin Redhill is observed to be greater than that of the above common human serum albumin by approximately 2.5 kDa.

There has been reported a method to increase the stability of a protein, such as an enzyme, in plasma by fusing HSA with the protein (Non-patent document 1, Patent documents 1 and 2). A fusion protein of HSA and an enzyme or the like is to be produced, by incorporating a DNA fragment in which the genes encoding the HSA and a gene encoding the enzyme or the like are fused in frame into an expression vector and culturing transformed cells introduced with this expression vector, as a recombinant protein in the medium or in the cells.

Examples of proteins whose stability in plasma is increased by fusion with human serum albumin (HSA) include a fusion protein of HSA with G-CSF (Patent documents 3), a fusion protein of HSA with interferon (Patent document 4), a fusion protein of HSA with GLP-1 (Patent document 5), a fusion protein of HSA with insulin (Patent document 6), and the like.

Human growth hormone (hGH) is a protein secreted from the anterior pituitary under the control of hypothalamus, and is a single chain polypeptide consisting of 191 amino acids and internally cross-linked by two disulfide bonds. Human GH exhibits growth-promoting activity including acceleration of chondrogenesis, acceleration of protein anabolism, and the like, as well as improvement of body composition and lipids metabolism. Children with low secretion of hGH develop growth hormone deficiency short stature, which is characterized by short stature compared to healthy children.

Pharmaceutical preparations (hGH preparation) containing hGH as the active principle, which is prepared as a recombinant protein utilizing *E. coli* cells with an introduced hGH gene and has molecular weight of approximately 22 kDa, are clinically used widely as a therapeutic drug for growth hormone deficiency short stature, short stature in Turner syndrome, short stature in SGA (Small-for-Gestational Age), short stature by chronic renal failure, short stature in Prader-Willi syndrome, and short stature in achondroplasia, accompanied by no epiphyseal closure. After subcutaneous or intramuscular administration of an hGH preparation, it circulates in the blood, and its growth-promoting activity promotes growth of the patient. Preparations containing hGH are clinically used widely also as a therapeutic drug for adult growth hormone deficiency. Patients with adult growth hormone deficiency show various abnormalities such as abnormal lipid metabolism, and administration of hGH preparation will bring about improved QOL of the patients through, e.g., normalization of patients' lipid metabolism. Growject™, e.g., is available as an hGH preparation for growth hormone deficiency short stature and adult growth hormone deficiency.

HGH secreted from the anterior pituitary under the control of the hypothalamus includes hGH (22K hGH) having a molecular weight of about 22 kDa, and a variant (20K hGH) having a molecular weight of about 20 kDa, in which 15 amino acids is deleted at positions 32-46 from the N-terminus of the 191 amino acids that forms 22K hGH. The abundance ratio of 20K hGH in total hGH in blood is about 5 to 15%. It is also known that 20K hGH shows a growth-promoting activities equivalent to that of 22K hGH.

The stability of hGH in plasma is also increased by fusing it with human serum albumin (HSA) (Patent Documents 4, 5, and 7 to 10). However, all of these reports relate to a fusion protein of HSA and 22K hGH.

Those attempts to improve stability of hGH in plasma were made in response to clinical needs. The half-life of hGH in plasma is regarded to be less than 20 minutes, and hGH administered to a patient thus quickly disappears from the blood. For hGH to exhibit its pharmacological activity in a patient, therefore, it must be administered to the patient either three times a week intramuscularly or everyday subcutaneously. Such frequent administration imposes a burden on patients. So, reduction of administration frequency, if achieved by increasing the stability of hGH in plasma and thereby elongating its half-life in plasma, would be desirable as leading to reduction of patients' burden.

PRIOR ART DOCUMENTS

Patent Documents

[Patent Document 1] JP H07-503368
[Patent Document 2] JP H03-178998
[Patent Document 3] JP H07-503844
[Patent Document 4] JP 2003-530838
[Patent Document 5] JP 2005-514060
[Patent Document 6] JP 2010-500031
[Patent Document 7] JP 2000-502901
[Patent Document 8] JP 2008-518615
[Patent Document 9] JP 2013-501036
[Patent Document 10] JP 2013-518038

Non-Patent Documents

[Non-patent Document 1] Poznansky MJ. et al., FEBS Letter. 239, 18-22 (1988)

SUMMARY OF INVENTION

Technical Problem

Under the above background, one object of the present invention is to provide a drug having growth-promoting activity but low prolactin-like activity, which contains a fusion protein having a human serum albumin part and a 20K human growth hormone (20K hGH) part as an active ingredient.

Means to Solve the Problem

In a study for the above-mentioned object, the present inventors have found that the prolactin-like activity of a fusion protein in which the C-terminus of human serum albumin binds to the N-terminus of 20K hGH is lower than that of 22K hGH, thereby completing the present invention. Thus the present invention includes what follows:

(1) A fusion protein having a growth-promoting activity, and having a human serum albumin part and a 20K human growth hormone part.

(2) The fusion protein according to 1 above, wherein the 20K human growth hormone part has an amino acid sequence selected from the group consisting of (a) to (c) below, (a) the amino acid sequence set forth as SEQ ID NO:1, wherein not more than 8 amino acids are deleted, not more than 8 amino acids are substituted by different amino acids, and not more than 8 amino acids are added, (b) the amino acid sequence set forth as SEQ ID NO:1, wherein not more than 4 amino acids are deleted, not more than 4 amino acids are substituted by different amino acids, and not more than 4 amino acids are added, and (c) the amino acid sequence set forth as SEQ ID NO:1, wherein not more than 2 amino acids are deleted, not more than 2 amino acids are substituted by different amino acids, and not more than 2 amino acids are added.

(3) The fusion protein according to 1 above, wherein the 20K human growth hormone part has an amino acid sequence selected from the group consisting of (a) to (c) below, (a) the amino acid sequence set forth as SEQ ID NO:1, wherein 1 to 8 amino acids are deleted, (b) the amino acid sequence set forth as SEQ ID NO:1, wherein 1 to 8 amino acids are substituted by different amino acids, and (c) the amino acid sequence set forth as SEQ ID NO:1, wherein 1 to 8 amino acids are added.

(4) The fusion protein according to 1 above, wherein the 20K human growth hormone part has the amino acid sequence set forth as SEQ ID NO:1.

(5) The fusion protein according to one of 1 to 4 above, wherein the human serum albumin part has an amino acid sequence selected from the group consisting of (a) to (c) below, (a) the amino acid sequence set forth as SEQ ID NO:2, wherein not more than 10 amino acids are deleted, not more than 10 amino acids are substituted by different amino acids, and not more than 10 amino acids are added, (b) the amino acid sequence set forth as SEQ ID NO:2, wherein not more than 5 amino acids are deleted, not more than 5 amino acids are substituted by different amino acids, and not more than 5 amino acids are added, and (c) the amino acid sequence set forth as SEQ ID NO:2, wherein not more than 3 amino acids are deleted, not more than 3 amino acids are substituted by different amino acids, and not more than 3 amino acids are added.

(6) The fusion protein according to one of 1 to 4 above, wherein the human serum albumin part has an amino acid sequence selected from the group consisting of (a) to (c) below, (a) the amino acid sequence set forth as SEQ ID NO:2, wherein 1 to 10 amino acids are deleted, (b) the amino acid sequence set forth as SEQ ID NO:2, wherein 1 to 10 amino acids are substituted by different amino acid, and (c) the amino acid sequence set forth as SEQ ID NO:2, wherein 1 to 10 amino acids are added.

(7) The fusion protein according to one of 1 to 4 above, wherein the human serum albumin part has the amino acid sequence set forth as SEQ ID NO:2.

(8) The fusion protein according to one of 1 to 4 above, wherein the human serum albumin part has the amino acid sequence set forth as SEQ ID NO:2, of which the tyrosin residue occurring at position 319 from the N-terminus is substituted by an amino acid residue except proline residue and the alanine residue occurring at position 320 from the N-terminus is substituted by threonine or serine.

(9) The fusion protein according to one of 1 to 4 above, wherein the human serum albumin part has the amino acid sequence set forth as SEQ ID NO:46.

(10) The fusion protein according to one of 1 to 9 above, wherein the human serum albumin part and the 20K human growth hormone part are linked via a linker part.

(11) The fusion protein according to 10 above, wherein the linker part consists of a non-peptide linker or a peptide linker.

(12) The fusion protein according to 11 above, wherein the linker part consists of the non-peptide linker, and the non-peptide linker consists of polyethylene glycol or a derivative thereof.

(13) The fusion protein according to one of 1 to 9 above, the fusion protein being a single chain polypeptide.

(14) The fusion protein according to 13 above, wherein the human serum albumin part is positioned on the N-terminal side of the growth hormone part.

(15) The fusion protein according to 13 above, wherein the growth hormone part is positioned on the N-terminal side of the human serum albumin part.

(16) The fusion protein according to one of 1 to 9 above, which is a single chain polypeptide, and wherein the human serum albumin part and the 20K human growth hormone part are linked via a linker part.

(17) The fusion protein according to 16 above, wherein the C-terminus of the human serum albumin part and the N-terminus of the linker part are linked by a peptide bond, and the C-terminus of the linker part and the N-terminus of the 20K human growth hormone part are linked by a peptide bond.

(18) The fusion protein according to 16 above, wherein the C-terminus of the 20K human growth hormone part and the N-terminus of the linker part are linked by a peptide bond, and the C-terminus of the linker part and the N-terminus of the human serum albumin part are linked by a peptide bond.

(19) The fusion protein according to one of 16 to 18 above, wherein the linker part comprises a peptide linker consisting of 1 to 50 amino acids.

(20) The fusion protein according to 19 above, wherein the linker part comprises an amino acid sequence selected from the group consisting of (a) to (c) below,
(a) an amino acid sequence in which the amino acid sequence set forth as SEQ ID NO:4 is consecutively repeated 2 to 10 times,
(b) an amino acid sequence in which the amino acid sequence set forth as SEQ ID NO:4 is consecutively repeated 2 to 6 times, and
(c) an amino acid sequence in which the amino acid sequence set forth as SEQ ID NO:4 is consecutively repeated 3 to 5 times.

(21) The fusion protein according to 19 above, wherein the linker part consists of a peptide linker comprising an amino acid sequence selected from the group consisting of (a) to (c) below,
(a) the amino acid sequence set forth as SEQ ID NO:4, wherein not more than 2 amino acids are deleted, not more than 2 amino acids are substituted by different amino acids, and not more than 2 amino acids are added, and
(b) the amino acid sequence set forth as SEQ ID NO:4, wherein not more than one amino acid is deleted, not more than one amino acid is substituted by different amino acid, and not more than one amino acid is added.

(22) The fusion protein according to 19 above, wherein the linker part consists of a peptide linker comprising an amino acid sequence selected from the group consisting of (a) to (c),
(a) the amino acid sequence set forth as SEQ ID NO:4, wherein 1 or 2 amino acids are deleted,
(b) the amino acid sequence set forth as SEQ ID NO:4, wherein 1 or 2 amino acids are substituted by different amino acids, and
(c) the amino acid sequence set forth as SEQ ID NO:4, wherein 1 or 2 amino acids are added.

(23) The fusion protein according to 19 above, wherein the linker part consists of a peptide linker comprising the amino acid sequence set forth as SEQ ID NO:4.

(24) The fusion protein according to 19 above, wherein the linker part consists of a peptide linker comprising an amino acid sequence selected from the group consisting of (a) to (c),
(a) the amino acid sequence set forth as SEQ ID NO:5, wherein not more than 5 amino acids are deleted, not more than 5 amino acids are substituted by different amino acids, and not more than 5 amino acids are added,
(b) the amino acid sequence set forth as SEQ ID NO:4, wherein not more than 3 amino acids are deleted, not more than 3 amino acids are substituted by different amino acids, and not more than 3 amino acids are added, and
(c) the amino acid sequence set forth as SEQ ID NO:4, wherein not more than 2 amino acids are deleted, not more than 2 amino acids are substituted by different amino acids, and not more than 2 amino acids are added.

(25) The fusion protein according to 19 above, wherein the linker part consists of a peptide linker comprising an amino acid sequence selected from the group consisting of (a) to (c);
(a) the amino acid sequence set forth as SEQ ID NO:5, wherein 1 to 5 amino acids are deleted,
(b) the amino acid sequence set forth as SEQ ID NO:5, wherein 1 to 5 amino acids are substituted by different amino acids,
(c) the amino acid sequence set forth as SEQ ID NO:5, wherein 1 to 5 amino acids are added.

(26) The fusion protein according to 19 above, wherein the linker part consists of a peptide linker comprising an amino acid sequence set forth as SEQ ID NO:5.

(27) The fusion protein according to 1 above, wherein the C-terminus of the human serum albumin part and the N-terminus of a linker part are linked by a peptide bond, and the C-terminus of the linker part and the N-terminus of the human growth hormone part are linked by a peptide bond, consisting of an amino acid sequence selected from the group consisting of (a) to (c);
(a) the amino acid sequence set forth as SEQ ID NO:36, wherein not more than 10 amino acids are deleted, not more than 10 amino acids are substituted by different amino acids, and not more than 10 amino acids are added,
(b) the amino acid sequence set forth as SEQ ID NO: 36, wherein not more than 5 amino acids are deleted, not more than 5 amino acids are substituted by different amino acids, and not more than 5 amino acids are added, and
(c) the amino acid sequence set forth as SEQ ID NO: 36, wherein not more than 3 amino acids are deleted, not more than 3 amino acids are substituted by different amino acids, and not more than 3 amino acids are added.

(28) The fusion protein according to 1 above, wherein the C-terminus of the human serum albumin part and the N-terminus of a linker part are linked by a peptide bond, and the C-terminus of the linker part and the N-terminus of the human growth hormone part are linked by a peptide bond, consisting of an amino acid sequence selected from the group consisting of (a) to (c),
(a) the amino acid sequence set forth as SEQ ID NO:36, wherein not more than 10 amino acids are deleted,
(b) the amino acid sequence set forth as SEQ ID NO:36, wherein not more than 10 amino acids are substituted by different amino acids, and
(c) the amino acid sequence set forth as SEQ ID NO:36, wherein not more than 10 amino acids are added.

(29) The fusion protein according to 1 above, wherein the C-terminus of the human serum albumin part and the N-terminus of a linker part are linked by a peptide bond, and the C-terminus of the linker part and the N-terminus of the human growth hormone part are linked by a peptide bond, consisting of the amino acid sequence set forth as SEQ ID NO:36.

Effect of Invention

According to the present invention, there is provided a long-lasting growth hormone preparation which can be used as a therapeutic agent for growth hormone deficiency short stature, having lower prolactin-like activity and higher stability in blood than the wild-type 22K GH by fusing 20K human growth hormone with human serum albumin.

DESCRIPTION OF EMBODIMENTS

Figure 1:
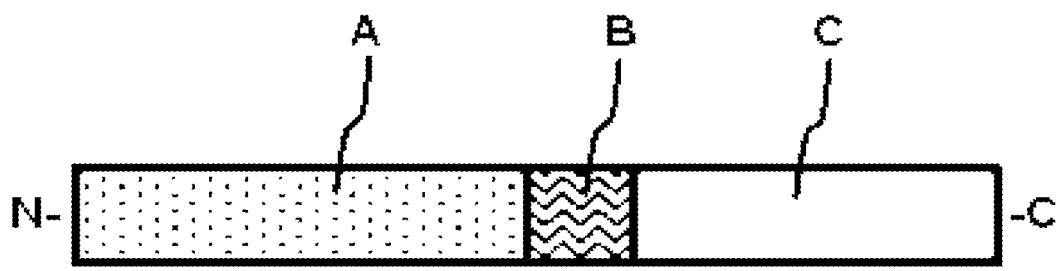
FIG. 1 is a diagram schematically showing a fusion protein of a single polypeptide chain having an HSA part, a linker part, and a 20K hGH part in the order from the N-terminal side. In the figure, "A" designates a human serum albumin part, "B" a linker part, "C" a 20K hGH part, "N-" an N-terminal, and "—C" a C-terminal, respectively.

The present invention relates to a fusion protein in which a polypeptide including human serum albumin or a mutant thereof is linked with a polypeptide including 20K human growth hormone or a mutant thereof. The term "fusing polypeptides" refers to binding different polypeptides by covalent bond directly or indirectly via a linker moiety.

As a method for binding two different polypeptides, for example, a method is generally applied in which an expression vector incorporating a DNA fragment produced by linking, downstream of the gene encoding one of the polypeptides, the gene encoding the other polypeptide in-frame, is constructed, and host cells transformed with this expression vector are cultured, thereby a recombinant protein is expressed. The resulting recombinant protein is a single chain polypeptide in which two polypeptides are peptide-linked directly or via another amino acid sequence.

Besides, as a method for binding two different polypeptides, a method also may be employed in which both of the polypeptides are separately prepared as recombinant proteins, and these two polypeptides then are linked via a non-peptide linker or a peptide linker. Examples of non-peptide linker that may be used include polyethylene glycol, polypropylene glycol, copolymers of ethylene glycol and propylene glycol, polyoxyethylated polyol, polyvinyl alcohol, polysaccharide, dextran, polyvinyl ether, biodegradable polymer, lipid polymers, chitins, hyaluronic acid, derivatives thereof, or combinations thereof.

In the present invention, the term "human serum albumin" or "HSA" does not only mean the wild-type human serum albumin consisting of 585 amino acids set forth as SEQ ID NO:2 but also includes such HSA mutants as correspond to those produced by substitution of one or more amino acids by different amino acids, deletion of one or more amino acids, or the like in the amino acid sequence set forth as SEQ ID NO:2, so long as they still have such functions of wild-type human serum albumin as binding to and carrying intrinsic compounds as well as extrinsic compounds, e.g., drugs, in the blood. When deleting some amino acids, the number of amino acids to be deleted is preferably 1 to 10, more preferably 1 to 5, still more preferably 1 to 3. When substituting some amino acids by different amino acids, the number of amino acids to be substituted is preferably 1 to 10, more preferably 1 to 5, still more preferably 1 to 3. For example, a protein consisting of 584 amino acids produced by deletion of one amino acid from the N- or C-terminus of the amino acid sequence set forth as SEQ ID NO:2 also is included in the meaning of human serum albumin. Further, such substitution and deletion of amino acids can be combined to obtain a desired mutant of HSA. Furthermore, a protein in which one or more amino acids are added to the amino acid sequence of wild-type HSA or a variant thereof, within their amino acid sequences or on their N- or C-terminus, is included in the meaning of HSA of the present invention, so long as they still have such functions of human serum albumin as binding to and carrying intrinsic compounds as well as extrinsic compounds, e.g., drugs, in the blood. The number of amino acids to be added herein is preferably 1 to 10, more preferably 1 to 5, still more preferably 1 to 3. A desirable mutant of HSA can also be obtained by combining such addition, substitution, and deletion of amino acids.

As a mutant of HSA in which the addition, the substitution, and the deletion of amino acids are combined, preferable is a mutant in which 10 or less of amino acids are deleted, 10 or less of amino acids are added, and 10 or less of amino acids are substituted in the amino acid sequence set forth as SEQ ID NO: 2, more preferable is a mutant in which 5 or less of amino acids are deleted, 5 or less of amino acids are added, and 5 or less of amino acids are substituted in the amino acid sequence set forth as SEQ ID NO: 2, further preferable is a mutant in which 3 or less of amino acids are deleted, 3 or less of amino acids are added, and 3 or less of amino acids are substituted in the amino acid sequence set forth as SEQ ID NO: 2.

In the present specification, the substitution of an amino acid with another amino acid may be either conservative or non-conservative amino acid substitution. The conservative amino acid substitution is conducted based on the similarity in polarity, charge, solubility, hydrophobicity, hydrophilicity and/or amphiphilic nature of amino acids. Conservative amino acid substitutions, for example, include the substitution of an amino acid with an amino acid classified in the same group such as aromatic amino acids (Phe, Trp, Tyr), aliphatic amino acids (Ala, Leu, Ile, Val), polar amino acids (Gln, Asn), basic amino acids (Lys, Arg, His), acidic amino acids (Glu, Asp), amino acids having hydroxyl groups (Ser, Thr), and so on. Further, examples of conservative amino acid substitutions include the substitution of an amino acid with an amino acid classified in the same group such as hydrophobic amino acids (Ala, Leu, Ile, Val, Pro, Phe, Trp, Met), polar neutral amino acids (Gly, Ser, Thr, Cys, Tyr, Gln, Asn), and amino acids affecting the conformation of the peptide chain (Pro, Gly).

A preferred embodiment is the mutant of human serum albumin in which alanine at the 320th amino acid from the N-terminal is replaced with threonine or serine, as compared to the amino acids sequence of the wild type human serum albumin consisting of 585 amino acids set forth as SEQ ID NO: 2. Further, a preferred embodiment is the mutant of human serum albumin in which tyrosine, the amino acid residue at the 319th amino acid from the N-terminal, is replaced with an amino acid residue other than proline, and alanine, the amino acid residue at the 320th amino acid from the N-terminal, is replaced with threonine or serine, as compared to the amino acids sequence of the wild type human serum albumin set forth as SEQ ID NO: 2. In these mutants, the amino acid substitution results in a tripeptide sequence represented by Asn-X-Ser or Asn-X-Thr, where X is any amino acid except proline. The asparagine residue in this tripeptide sequence can be glycosylated by an N-linked sugar chain when the genes encoding these mutants are incorporated into an expression vector and expressed in a eukaryotic cell such as a mammalian cell.

In the present invention, the term "human serum albumin Redhill" (HSA-Redhill) means a variant of human serum albumin consisting of 586 amino acids set forth as SEQ ID NO:46. Compared to the wild-type human serum albumin consisting of 585 amino acids set forth as SEQ ID NO:2, human serum albumin Redhill has a sequence in which the amino acid residue at position 320 from the N-terminus is not alanine but threonine, and one arginine residue is added to the N-terminus. As a result of the substitution of alanine by threonine, albumin Redhill contains an amino acid sequence, Asn-Tyr-Thr, within its amino acid sequence, and the Asn (asparagine) residue in this sequence receives N-linked glycosylation. Thus, albumin Redhill is observed as having a molecular weight greater by 2.5 kDa than the ordinary wild-type albumin (SEQ ID NO:2). In the present invention, the term "human serum albumin" or "HSA" also includes HSA-Redhill.

There are mainly two types of human growth hormone secreted from human pituitary gland, 22K human growth hormone and 20K human growth hormone, having different molecular weights each other. 22K growth hormone is a protein having 191 amino acids containing the amino acid sequence set forth as SEQ ID NO:3. Usually, "human growth hormone" or "hGH" refers to this 22K growth hormone, but in the following description, when simply referred to as "human growth hormone" or "hGH", it includes both of 22K human growth hormone and 20K human growth hormone.

The wild-type 20K human growth hormone is a protein, having growth-promoting activity, comprising 176 amino acids, and having amino acid sequence set forth as SEQ ID NO:1 which corresponds to the 22K human growth hormone consisting of 191 amino acids set forth as SEQ ID NO:3 but lacking 15 amino acids, the 32nd to the 46th amino acids from its N-terminus. In the present invention, however, the term "20K human growth hormone" or "20K hGH" includes not only the wild-type 20K hGH represented by SEQ ID NO:1 but also variants of 20K hGH in which one or more amino acids of the amino acid sequence set forth as SEQ ID NO:1 are deleted, substituted by other amino acids, or the like. When amino acids are to be deleted, the number of amino acids to be deleted is preferably 1 to 8, more preferably 1 to 5, still more preferably 1 or 2. When amino acids are substituted by different amino acids, the number of amino acids to be substituted is preferably 1 to 8, more preferably 1 to 4, still more preferably 1 or 2. These substitution and deletion can be combined to obtain a desired mutant of 20K hGH.

Further, a human growth hormone in which one or more amino acids are added to the amino acid sequence of the wild-type 20K human growth hormone or a mutant thereof, within its amino acid sequence or on its N- or C-terminus, is also included in 20K human growth hormone (20K hGH) of the present invention, as far as it shows growth-promoting activity. The number of amino acids to be added herein is preferably 1 to 8, more preferably 1 to 4, still more preferably 1 or 2. Such addition, substitution, and deletion of amino acids can be combined to obtain a desired mutant of 20K hGH.

As a mutant of 20K human growth hormone in which the addition, the substitution, and the deletion of amino acids are combined, preferable is a mutant in which 8 or less of amino acids are deleted, 8 or less of amino acids are added, and 8 or less of amino acids are substituted in the amino acid sequence set forth as SEQ ID NO: 1, more preferable is a mutant in which 4 or less of amino acids are deleted, 4 or less of amino acids are added, and 4 or less of amino acids are substituted in the amino acid sequence set forth as SEQ ID NO: 1, further preferable is a mutant in which 3 or less of amino acids are deleted, 3 or less of amino acids are added, and 3 or less of amino acids are substituted in the amino acid sequence set forth as SEQ ID NO: 1.

The fusion protein of the present invention is a protein in which human serum albumin is fused to 20K hGH, and has a human serum albumin part and a 20K human growth hormone part.

Herein, the term "human serum albumin part" or "HSA part" refers to a part containing an amino acid sequence corresponding to HSA in the fusion protein, and having a function as human serum albumin such as binding to and carrying intrinsic compounds as well as extrinsic compounds, e.g., drugs, in the blood. And herein, the "amino acid sequence derived from HSA" includes the amino acid sequence of wild-type human serum albumin consisting of 585 amino acids set forth as SEQ ID NO:2, and additionally the amino acid sequence of a mutant of HSA in which one or more of amino acids are deleted, or substituted by other amino acids in comparison to the amino acid sequence set forth as SEQ ID NO: 2. When amino acids are to be deleted, the number of amino acids to be deleted is preferably 1 to 10, more preferably 1 to 5, still more preferably 1 or 3. When amino acids are substituted by other amino acids, the number of amino acids to be substituted is preferably 1 to 10, more preferably 1 to 5, still more preferably 1 or 2. For example, the amino acid sequence consisting of 584 amino acids, in which an amino acid at the N- or C-terminus of the amino acid sequence set forth as SEQ ID NO: 2 is deleted, is also included in "amino acid sequence derived from HSA". A desirable amino acid sequence of a mutant of HSA can be obtained by combining such substitution and deletion of amino acids.

Further, an amino acid sequence in which one or more amino acids are added to the amino acid sequence of wild-type HSA or a variant thereof, within those amino acid sequences or on their N- or C-terminus, is also included in "amino acid sequence derived from HSA". The number of amino acids to be added herein is preferably 1 to 10, more preferably 1 to 5, still more preferably 1 to 3. A desirable mutant of HSA can be obtained by combining such addition, substitution, and deletion of amino acids. However, when a fusion protein is prepared as a single chain polypeptide having a linker part as described in detail below, it is assumed that the amino acid sequence considered to be a part of the linker part preferentially belongs to the linker part, not to the HSA part.

As a mutant of HSA in which such addition, substitution, and deletion of amino acids are combined, preferable is a mutant in which 10 or less of amino acids are deleted, 10 or less of amino acids are added, and 10 or less of amino acids are substituted in the amino acid sequence set forth as SEQ ID NO:2, more preferable is a mutant in which 5 or less of amino acids are deleted, 5 or less of amino acids are added, and 5 or less of amino acids are substituted in the amino acid sequence set forth as SEQ ID NO:2, further preferable is a mutant in which 3 or less of amino acids are deleted, 3 or less of amino acids are added, and 3 or less of amino acids are substituted in the amino acid sequence set forth as SEQ ID NO:2.

Preferred embodiments of variants of human serum albumin that can be used as the human serum albumin part include such a variant in which alanine, the 320th amino acid from N-terminus in comparison to wild-type human serum albumin consisting of 585 amino acids set forth as SEQ ID NO: 2, is substituted by threonine or serine. In addition, preferred embodiments of a variant of HSA include a human serum albumin in which tyrosin as the 319th amino acid residue from the N-terminus is replaced with an amino acid residue other than proline residue, and alanine residue as the 320th amino acid residue from the N-terminus is replaced with threonine or serine residue in comparison to the amino acid sequence of the wild-type human serum albumin consisting of 585 amino acids set forth as SEQ ID NO:2. In these variants, tripeptide sequence represented by Asn-X-Ser or Asn-X-Thr (X may be any one of amino acid except proline) arises by the substitution of amino acid. The asparagine residue in this tripeptide sequence can be glycosylated by an N-linked sugar chain when the gene encoding the fusion protein is incorporated into an expression vector and expressed in eukaryotic cells such as mammalian cells. Human serum albumin Redhill (HSA-Redhill) consisting of 586 amino acids set forth as SEQ ID NO:46 can also be used as the human serum albumin part.

In the fusion protein, the term "20K human growth hormone part" or "20K hGH part" refers to a moiety containing an amino acid sequence derived from 20K hGH and having growth-promoting activity. Here, the "amino acid sequence derived from 20K hGH" refers to not only the amino acid sequence of the wild-type 20K human growth hormone consisting of 176 amino acids set forth as SEQ ID NO: 1 but also the amino acid sequence of a mutant of 20K human growth hormone in which one or more of amino acids have been deleted, replaced with other amino acids, or the like. When deleting some amino acids, the number of amino acid to be deleted is preferably 1-8, more preferably 1-4, and still more preferably 1 or 2. When substituting some amino acids, the number of amino acid to be substituted is preferably 1-8, more preferably 1-4, and still more preferably 1 or 2. Further, such substitution and deletion of amino acids may be combined to obtain a desired amino acid sequence derived from 20K hGH.

Moreover, an amino acid sequence in which one or more of amino acids have been added within the amino acid sequence or to the N or C-terminus of wild-type 20K human growth hormone or a mutant thereof is also included in the amino acid sequence derived from 20K hGH. The number of amino acids to be added herein is preferably 1 to 8, more preferably 1 to 4, still more preferably 1 or 2. Such addition, substitution and deletion of amino acids may be combined to obtain the desired amino acid sequence of the mutant of 20K human growth hormone. However, when a fusion protein is produced as a single chain polypeptide having a linker part as described in detail below, the amino acid sequence which can be a part of the linker part should preferentially be considered to belong to the linker part, not to the 20K hGH part.

As a mutant of 20K human growth hormone in which the addition, the substitution, and the deletion of amino acids are combined, preferable is a variant in which 8 or less amino acids are deleted, 8 or less amino acids are replaced with different amino acids, and 8 or less amino acids are added in comparison to the amino acid sequence set forth as SEQ NO:1, more preferable is a variant in which 4 or less amino acids are deleted, 4 or less amino acids are replaced with different amino acids, and 4 or less amino acids are added in comparison to the amino acid sequence set forth as SEQ NO:1, further more preferable is a variant in which 2 or less amino acids are deleted, 2 or less amino acids are replaced with different amino acids, and 2 or less amino acids are added in comparison to the amino acid sequence set forth as SEQ NO:1.

In the fusion protein of the present invention, the human serum albumin part and the 20K hGH part are linked directly or via a linker part. Here, the term "linker part" refers to a moiety that does not belong to either the human serum albumin part or the 20K hGH part, and that comprises a peptide chain or a long-chain molecule other than a peptide, or derivatives thereof. When the linker part is a peptide chain or a derivative thereof, the linker part is referred to as consisting of a peptide linker, and when the linker part is a long-chain molecule other than a peptide or a derivative thereof, the linker part is referred to as consisting of a non-peptide linker, The linker part has various functions. These functions include such a function as to connect the HSA part and the 20K hGH part between them, to reduce the mutual interference of both parts, and to give flexibility to the three-dimensional structure of the fusion protein as a hinge which connects two parts between them. In the molecule of the fusion protein, the linker part exerts at least one of these functions.

A fusion protein having the HSA part and the 20K hGH part is produced as a recombinant protein by preparing an expression vector incorporating a DNA fragment in which the gene encoding hGH has been linked downstream or upstream of the gene encoding HSA in frame, and culturing host cells transformed by introduction of the expression vector. The fusion protein thus produced as a recombinant protein consists of a single chain polypeptide. Further, in the present invention, a fusion protein prepared as a recombinant protein is referred to as a recombinant fusion protein.

In the case of preparing a fusion protein as a recombinant fusion protein, it is possible to obtain a fusion protein having the 20K hGH part on the C-terminal side of the HSA part by linking the gene encoding 20K hGH downstream of the gene encoding HSA in frame. Conversely, by linking the gene encoding 20K hGH upstream of the gene encoding HSA in frame, a fusion protein having the 20K hGH part on the N-terminal side of the HSA part can be obtained. In either case, the fusion protein produced as a recombinant fusion protein is a single chain polypeptide.

In the present invention, the term "single chain polypeptide" refers to a polypeptide having one N-terminus and one C-terminus, and having no branched peptide chain. As long as this condition is satisfied, those having intramolecular disulfide bonds, those modified with sugar chains, lipids, phospholipids, or the like are also single-chain polypeptides. In addition, in the case where a single chain polypeptide forms a complex such as a dimer by non-covalent bond, the individual peptide chain forming the complex is understood as a single chain polypeptide, and the complex itself is understandable as an aggregate of single chain polypeptides.

In the present invention, within the single chain polypeptide of the fusion protein, the HSA part can be located at either the N-terminus or C-terminus of the 20K hGH part, but preferably the HSA part is located at the N-terminus of the 20K hGH part.

When the HSA part is located on the N-terminus of the 20K hGH part within the single-chain polypeptide of the fusion protein, the C-terminus of the HSA part and the N-terminus of the 20K human growth hormone part are linked directly or via a linker part. Herein, the "linker part" referred to an amino acid sequence which does not belong to either the HSA part or the 20 K hGH part and is located between the C-terminus of the HSA part and the N-terminus of the 20K hGH part within the single-chain polypeptide. FIG. 1 schematically shows a fusion protein comprising a single chain polypeptide having an HSA part, a linker part, and a 20K hGH part in the order from the N-terminal side. Herein, the linker part consists of a peptide linker, the C-terminus of the human serum albumin part and the N-terminus of the linker part are linked by a peptide bond, and the C-terminal of the linker part and the N-terminus of the 20K human growth hormone part is bound by a peptide bond.

When the 20K hGH part is located on the N-terminal side of the HSA part within the single-chain polypeptide, the C-terminus of the 20K hGH part and the N-terminus of the HSA part are linked directly or via a linker part. Here, the term "linker part" refers to a moiety having an amino acid sequence not belonging to either the HSA part or the 20K hGH part and located between the C-terminus of the 20K hGH part and the N-terminus of the HSA part within the single-chain polypeptide. In this case, the linker part also consists of a peptide linker, and herein the C-terminus of the 20K human growth hormone part and the N-terminus of the linker part are bound by a peptide bond, and the C-terminus of the linker part and the N-terminus of the human serum albumin part are bound by a peptide bond.

The amino acid sequence of the peptide linker is not particularly limited as long as it exerts its functions as a linker part within the fusion protein molecule. Further, the length of the peptide linker is not particularly limited as long as it exerts its functions as a linker part within the fusion protein molecule. The peptide linker comprises one or more amino acids. When the peptide linker comprises a plurality of amino acids, the number of the amino acids is preferably 2 to 50, more preferably 5 to 30, still more preferably 10 to 25. Preferred examples of the peptide linker include those consisting of Gly-Ser, Gly-Gly-Ser, or the amino acid sequence set forth as SEQ ID NO:4 (these are collectively referred to as basic sequences), and those containing these amino acid sequences. For example, the peptide linker contains an amino acid sequence in which the basic sequences are repeated 2 to 10 times, an amino acid sequence in which the basic sequences are repeated 2 to 6 times, or an amino acid sequence in which the basic sequences are repeated three to five times. A preferable example of the amino acid sequence of the peptide linker includes the amino acid sequence set forth as SEQ ID NO: 5 in which SEQ ID NO: 4 is repeated four times.

One or more of amino acids of the linker part may be deleted or replaced with different amino acids in comparison to the amino acid sequence set forth as SEQ ID NO:4. When amino acids are to be deleted, the number of amino acids to be deleted is preferably 1 or 2. When amino acids are substituted by different amino acids, the number of amino acids to be substituted is preferably 1 or 2. Such substitution and deletion of amino acids may be combined to obtain a desired amino acid sequence of a linker part.

Further the amid acid sequence of the linker part may be as such in which one or more amino acids are added to the amino acid sequence set forth as SEQ ID NO:4, within it or on the N-terminus or the C-terminus of it. The number of amino acids to be added in this case is preferably 1 or 2. Such addition, substitution, and deletion of the amino acids can be combined to obtain the desired amino acid sequence of a linker part.

As the amino acid sequence of the linker part in which such addition, substitution, and deletion of amino acids are combined, preferable is that in which 2 or less of amino acids are deleted, 2 or less of amino acids are replaced with different amino acids, and 2 or less of amino acids are added in the amino acid sequence set forth as SEQ ID NO:4, more preferable is that in which 1 or less of amino acid is deleted, 1 or less of amino acid is replaced with a different amino acid, and 1 or less of amino acid is added in the amino acid sequence set forth as SEQ ID NO:4.

One or more of amino acids of the linker part may be deleted or replaced with different amino acids in comparison to the amino acid sequence set forth as SEQ ID NO:5. When amino acids are substituted by different amino acids, the number of amino acids to be substituted is preferably 1 to 5, more preferably 1 to 3, still more preferably 1 or 2. When amino acids are to be deleted, the number of amino acids to be deleted is preferably 1 to 5, more preferably 1 to 3, still more preferably 1 or 2. Such substitution and deletion of amino acids may be combined to obtain a desired amino acid sequence of the linker part.

Further, the amino acid sequence of the linker part may be as such in which one or more amino acids are added to the amino acid sequence set forth as SEQ ID NO:5, within it or on the N- or C-terminus of it. The number of amino acids to be added in this case is preferably 1 to 5, more preferably 1 to 3, still more preferably 1 or 2. Such addition, substitution, and deletion of the amino acids can be combined to obtain the desired amino acid sequence of the linker part.

As the amino acid sequence of the linker part in which such addition, substitution, and deletion of amino acids are combined, preferable is that in which 5 or less of amino acids are deleted, 5 or less of amino acids are replaced with different amino acids, and 5 or less of amino acids are added in the amino acid sequence set forth as SEQ ID NO:5, more preferable is that in which 3 or less of amino acids are deleted, 3 or less of amino acids are replaced with different amino acids, and 3 or less of amino acids are added in the amino acid sequence set forth as SEQ ID NO:5, and still more preferable is that in which 2 or less of amino acids are deleted, 2 or less of amino acids are replaced with different amino acids, and 2 or less of amino acids are added in the amino acid sequence set forth as SEQ ID NO:5.

HSA-[linker]-20K hGH, a fusion protein consisting of 781 amino acids set forth as SEQ ID NO:36 is one of embodiments of the fusion proteins of the present invention, in which the C-terminus of the human serum albumin part and the N-terminus of the linker part are linked by a peptide bond, and the C-terminus of the linker part and the N-terminus of the 20K human growth hormone part are linked by a peptide bond. In the amino acid sequence set forth as SEQ ID NO:36, the portion consisting of 585 amino acids at positions 1 to 585 from the N-terminus corresponds to the human serum albumin part, the portion consisting of 20 amino acids at positions 586 to 605 from the N-terminus corresponds to the linker part, and the portion consisting of amino acids at positions 606 to 781 from the N-terminus corresponds to the linker part.

As desired, one or more of amino acids in the amino acid sequence set forth as SEQ NO:36 may be deleted, replaced with different amino acids, or the like, as long as each part of the fusion protein, ie, the human serum albumin part, the 20 K human growth hormone part, and the linker part exerts its respective functions. When deleting amino acids, the number of amino acids to be deleted is preferably 1 to 10, more preferably 1 to 5, still more preferably 1 to 3. When substituting amino acids with different amino acids, the number of amino acids to be substituted is preferably 1 to 10, more preferably 1 to 5, still more preferably 1 to 3. Such substitution and deletion of amino acids may be combined to obtain a desired fusion protein.

Further, as desired, one or more of amino acids may be added to the amino acid sequence set forth as SEQ NO:36 within it or on N-terminus or C-terminus of it, as long as each part of the fusion protein, ie, the human serum albumin part, the 20K human growth hormone part and, the linker part exerts its respective functions. The number of amino acids to be added herein is preferably 1 to 10, more preferably 1 to 5, still more preferably 1 to 3. Such addition, substitution, and deletion of the amino acids can be combined to obtain a desired fusion protein.

As the desired fusion protein in which the addition, the substitution, and the deletion of amino acids are combined, preferable is that in which 10 or less of amino acids are deleted, 10 or less of amino acids are replaced with different amino acids, and 10 or less of amino acids are added in the amino acid sequence set forth as SEQ ID NO:36, more preferable is that in which 5 or less of amino acids are deleted, 5 or less of amino acids are replaced with different amino acids, and 5 or less of amino acids are added in the amino acid sequence set forth as SEQ ID NO:36, and still more preferable is that in which 3 or less of amino acids are deleted, 3 or less of amino acids are replaced with different amino acids, and 3 or less of amino acids are added in the amino acid sequence set forth as SEQ ID NO:36.

HSA-20K hGH which is a fusion protein consisting of 761 amino acids set forth as SEQ ID NO:29 is one of the embodiments of the fusion proteins of the present invention, wherein the C-terminus of the human serum albumin part and the N-terminus of the 20K human growth hormone part are linked by a peptide bond without via a linker part. In the amino acid sequence represented by SEQ ID NO: 29, a portion consisting of 585 amino acids at positions 1 to 585 from the N-terminus corresponds to the human serum albumin part and a portion consisting of amino acids at positions 586 to 761 from the N-terminus corresponds to the 20K human growth hormone part.

As desired, one or more of amino acids in the amino acid sequence set forth as SEQ NO:29 may be substituted, deleted, or the like, as long as each part of the fusion protein, ie, the human serum albumin part and the 20K human growth hormone part, exerts its respective functions. When substituting the amino acids, the number of amino acids to be substituted is preferably 1 to 10, more preferably 1 to 5, still more preferably 1 to 3. When deleting amino acids, the number of amino acids to be deleted is preferably 1 to 10, more preferably 1 to 5, still more preferably 1 to 3. Such substitution and deletion of amino acids may be combined to obtain a desired fusion protein.

Further, as desired, one or more of amino acids may be added to the amino acid sequence set forth as SEQ NO:29 within it or on N-terminus or C-terminus of it, as long as each part of the fusion protein, ie, the human serum albumin part and the 20K human growth hormone part exerts its respective functions. The number of amino acids to be added herein is preferably 1 to 10, more preferably 1 to 5, still more preferably 1 to 3. Such addition, substitution, and deletion of the amino acids can be combined to obtain a desired fusion protein.

As the desired fusion protein in which such addition, substitution, and deletion of amino acids are combined, preferable is that in which 10 or less of amino acids are deleted, 10 or less of amino acids are replaced with different amino acids, and 10 or less of amino acids are added in the amino acid sequence set forth as SEQ ID NO:29, more preferable is that in which 5 or less of amino acids are deleted, 5 or less of amino acids are replaced with different amino acids, and 5 or less of amino acids are added in the amino acid sequence set forth as SEQ ID NO: 29, and still more preferable is that in which 3 or less of amino acids are deleted, 3 or less of amino acids are replaced with different amino acids, and 3 or less of amino acids are added in the amino acid sequence set forth as SEQ ID NO:29.

A fusion protein having the HSA part and the 20K hGH part is produced as a recombinant protein by preparing an expression vector incorporating a DNA fragment in which the gene encoding hGH has been linked downstream or upstream of the gene encoding HSA in frame, and culturing host cells transformed by introduction of the expression vector.

When producing a fusion protein of the present invention in which the HSA part and the 20K hGH part are linked via a linker part, a DNA fragment encoding a fusion protein has been constructed in which a gene encoding HSA and a gene encoding 20K hGH are linked in frame via a DNA fragment encoding a peptide chain constituting the linker part. A fusion protein can be produced as a recombinant protein by culturing a host cell transformed with an expression vector incorporating this DNA fragment.

The expression vector incorporating the DNA fragment encoding the fusion protein is introduced into a host cell. There is no particular limitation as to the host cell to be used as long as it can express the fusion protein when introduced with the expression vector. An eukaryotic cell such as a mammalian cell, a yeast, a plant cell, and an insect cell, and prokaryotic cells such as *Escherichia coli* and *Bacillus subtilis* can be used, but mammalian cells are preferred.

Though there is no notable limitation as to the species of mammalian cells to be employed as host cells, preferred are cells derived from human, mouse, and Chinese hamster, among which CHO cells, which are derived from Chinese hamster ovary cells, or NS/O cells derived from mouse myeloma, human fibroblasts, and COS cells derived from African green monkey kidney fibroblasts are particularly preferred. And so long as it will lead to expression of the gene in mammalian cells into which it is introduced, there is no notable limitation as to an expression vector employed in which a DNA fragment encoding the fusion protein is incorporated for expressing the gene. The gene introduced into an expression vector is placed downstream of a DNA sequence that regulates the frequency of transcription of the gene in mammalian cells (gene expression regulatory site). Examples of a gene expression regulatory site which can be employed in the present invention include a Cytomegalovirus-derived promoter, SV40 early promoter, human elongation factor-1α (EF-1α) promoter, and human ubiquitin C promoter.

While mammalian cells having such an introduced expression vector come to produce the protein incorporated in the expression vector, the amount of its expression will vary cell by cell and will not be uniform. Mammalian cells into which such expression vectors have been introduced will express proteins incorporated into expression vectors, but the expression levels thereof are not uniform, depending on individual cells. For efficient production of the fusion protein, therefore, a step is required in which the cells exhibiting high expression level of the protein of interest are selected from the mammalian cells into which the expression vector has been introduced. For carrying out such a selection step, a gene acting as a selection marker is introduced in the expression vector.

The most common of such selection markers are enzymes that decompose drugs such as puromycin and neomycin (drug resistance marker). In general, mammalian cells will be killed by one of those drugs that is present beyond certain concentrations. Since cells having an introduced expression vector in which a drug resistance gene is incorporated can decompose the drug with the expressed drug resistance gene to detoxify it or attenuate its toxicity, they can survive even in the presence of such drugs. By introducing into mammalian cells an expression vector having an incorporated drug resistance gene as a selection marker, and then culturing the cells in a medium with a gradually increasing concentration of the drug corresponding to the drug resistance marker, such cells can be obtained that are able to grow even in the presence of higher concentrations of the drug. In the cells selected in this manner, generally, expression levels of the gene encoding the protein of interest incorporated in the expression vector are also elevated along with those of the drug resistance marker, and as a result those cells are selected which express the protein of interest at high levels.

Further, glutamine synthetase (GS) can also be used as a selection marker. Glutamine synthetase is an enzyme which synthesizes glutamine from glutamic acid and ammonia. If mammalian cells are cultured in a medium which contains an inhibitor of glutamine synthetase, e.g., methionine sulfoximine (MSX), yet no glutamine, the cells will be annihilated. However, if mammalian cells have an introduced expression vector in which glutamine synthetase is incorporated as a selection marker, the cells become able to grow even in the presence of higher concentrations of MSX because of their increased levels of glutamine synthetase expression. Here, if culture is continued with concentration of MSX gradually increased, such cells are obtained that can grow even in the presence of still higher concentrations of MSX. Generally, in cells selected by this way, expression levels of the gene encoding the protein of interest incorporated in the expression vector are also elevated along with those of the drug resistance marker, and as a result those cells are selected which express the protein of interest at high levels.

Dihydrofolate reductase (DHFR) can also be used as a selection marker. In the case where DHFR is employed as a selection marker, mammalian cells having the introduced expression vector is cultured in a selection medium containing a DHFR inhibitor such as methotrexate or aminopterin. Culture continued with gradually increasing concentration of a DHFR inhibitor give rise to such cells that can grow even in the presence of higher concentrations of the DHFR inhibitor. Generally, in cells selected in this manner, expression levels of the gene encoding the protein of interest incorporated in the expression vector are also elevated along with those of DHFR, and as a result those cells are selected which express the protein of interest at high levels.

An expression vector are known in which glutamine synthetase (GS) is placed as a selection marker downstream of the gene encoding a protein of interest via an internal ribosome entry site (IRES) (WO 2012/063799, WO 2013/161958). The expression vectors described in these documents can be used particularly preferably for production of the fusion protein of the present invention.

For example, an expression vector for expression of a protein of interest which comprises a gene expression regulatory site, a gene encoding the protein downstream thereof, an internal ribosome entry site further downstream thereof, and a gene encoding glutamine synthetase still further downstream thereof, and further comprises dihydrofolate reductase gene or a drug resistance gene either downstream of the gene expression regulatory site or downstream of a gene expression regulatory site other than "said gene expression regulatory site", can be preferably used in producing the fusion protein of the present invention. In this vector, a cytomegalovirus-derived promoter, SV40 early promoter, and human elongation factor-1α promoter (hEF-1α promoter), and human ubiquitin C promoter are preferably used as the first gene expression regulatory site or the second gene expression regulatory site, among which hEF-1α promoter is particularly preferred.

Further, as an internal ribosome entry site, preferably used is one of those derived from the 5' untranslated region of a virus or a gene selected from the group consisting of Picornaviridae, Picornaviridae Aphthovirus, hepatitis A virus, hepatitis C virus, coronavirus, bovine enterovirus, Theiler's murine encephalomyelitis virus, Coxsackie B virus, human immunoglobulin heavy chain binding protein gene, *Drosophila antennapedia* gene, and *Drosophila ultra-*

*bithorax* gene, among which particularly preferable is the internal ribosome entry site derived from the 5' untranslated region of mouse encephalomyocarditis virus. In the case where the 5' untranslated region of the mouse encephalomyocarditis virus is used, not only its wild-type but also those in which some of the plural start codons included in the wile-type internal ribosome entry sites are destroyed can preferably be employed. The drug resistance gene employed in the expression vector of the present invention is preferably puromycin or neomycin resistance gene, and more preferably puromycin resistance gene.

Furthermore, for example, an expression vector for expression of a protein of interest which comprises human elongation factor-1α promoter, a gene encoding the protein downstream thereof, and an internal ribosome entry site derived from the 5' untranslated region of mouse encephalomyocarditis virus further downstream thereof, and a gene encoding glutamine synthetase further downstream thereof, and further comprises another gene expression regulatory site and dihydrofolate reductase gene downstream thereof, wherein the internal ribosome entry site is one in which some of the plural start codons included in the wile-type internal ribosome entry sites are destroyed, can preferably be employed in producing a fusion protein of the present invention. An example of such vectors is one described in WO 2013/161958.

Still further, for example, an expression vector for expression of a protein of interest which comprises human elongation factor-1α promoter, a gene encoding the protein downstream thereof, an internal ribosome entry site derived from the 5' untranslated region of mouse encephalomyocarditis virus further downstream thereof, and a gene encoding glutamine synthetase still further downstream thereof, and further comprises another gene expression regulatory site and a drug resistance gene downstream thereof, wherein the internal ribosome entry site is one in which some of the plural start codons included in the wile-type internal ribosome entry sites are destroyed, can preferably be employed in producing a fusion protein of the present invention. Examples of such vectors are pE-mIRES-GS-puro described in WO 2012/063799 and pE-mIRES-GS-mNeo described in WO 2013/161958.

There are three start codons (ATG) at the 3' end of the internal ribosome entry site derived from the 5' untranslated region of the wild-type mouse encephalomyocarditis virus. The partial sequences containing those three start codons is shown as SEQ ID NO:6 (5'-ATGataatATGgccacaaccATG-3': the start codon ATG is shown in upper case letters). An example in which one of the start codons in this sequence is destroyed is one set forth as SEQ ID NO:7 (5'-atgataagcttgccacaaccatg-3'), and pE-mIRES-GS-puro and pE-mIRES-GS-mNeo above mentioned are expression vectors having IRES comprising the sequence set forth as SEQ ID NO:7.

In one embodiment of present invention, mammalian cells having an introduced expression vector, in which a DNA fragment encoding a fusion protein is incorporated, are subjected to selective culture in a selection medium to select cells showing high levels of their expression.

In the case where DHFR is used as a selection marker in selective culture, the concentration of a DHFR inhibitor in the selection medium is increased stepwise. The maximum concentration of it, where the DHFR inhibitor is methotrexate, is preferably 0.25 to 5 µM, more preferably 0.5 to 1.5 µM, and still more preferably about 1.0 µM.

In the case where GS is employed as the selection marker, the concentration of a GS inhibitor in the selection medium is increased stepwise. The maximum concentration of it, where the GS inhibitor is MSX, is preferably 100 to 1000 µM, more preferably 200 to 500 µM, and still more preferably about 300 µM. As a selection medium, a medium containing no glutamine is generally employed here.

In the case where an enzyme that decomposes puromycin is employed as a selection marker, the maximum concentration of puromycin in the selection medium is preferably 3 to 30 µg/mL, more preferably 5 to 20 µg/mL, and still more preferably about 10 µg/mL.

In the case where an enzyme that decomposes neomycin is employed as a selection marker, the maximum concentration of G418 in the selection medium is preferably 0.1 to 2 mg/mL, more preferably 0.5 to 1.5 mg/mL, and still more preferably about 1 mg/mL.

As a medium for culturing mammalian cells, either for selection culture or for production of the recombinant protein mentioned below (recombinant fusion protein production medium), any medium may be used without notable limitation so long as it allows cultivation of mammalian cells to let them grow in it, and among them a serum-free medium is preferably employed.

The cells selected by selection culture showing high levels of expression of the recombinant fusion protein are employed as recombinant fusion protein producing cells in the production of the recombinant fusion protein. Production of the recombinant fusion protein is performed by culturing the recombinant fusion protein producing cells in a medium for recombinant fusion protein production. This culture is called production culture.

In the present invention, as a serum-free medium employed for recombinant fusion protein production, a medium is preferably used that contains, e.g., 3 to 700 mg/L of amino acids, 0.001 to 50 mg/L of vitamins, 0.3 to 10 g/L of monosaccharides, 0.1 to 10000 mg/L inorganic salts, 0.001 to 0.1 mg/L of trace elements, 0.1 to 50 mg/L of nucleosides, 0.001 to 10 mg/L of fatty acids, 0.01 to 1 mg/L of biotin, 0.1 to 20 µg/L of hydrocortisone, 0.1 to 20 mg/L of insulin, 0.1 to 10 mg/L of vitamin B12, 0.01 to 1 mg/L of putrescine, 10 to 500 mg/L of sodium pyruvate, and water soluble iron compounds. Thymidine, hypoxanthine, a conventional pH indicator and antibiotics may also be added to the medium.

As a serum-free medium for recombinant protein production, DMEM/F12 medium (mixture medium of DMEM and F12), well known to a skilled artisan, may be used as a base medium. Furthermore, as a serum-free medium, DMEM (HG)HAM modified (R5) medium may also be used, which contains sodium bicarbonate, L-glutamine, D-glucose, insulin, sodium selenite, diaminobutane, hydrocortisone, iron(II) sulfate, asparagine, aspartic acid, serine, and polyvinylalcohol. Further, commercially available serum-free mediums, such as CD OptiCHO™ medium, CHO-S-SFM II medium, or CD CHO medium (Thermo Fisher Scientific Inc.), EX-CELL™ 302 medium, or EX-CELL™325-PF medium (SAFC Biosciences Inc.), may be used, too, as a base medium.

A fusion protein having the HSA part and the 20K hGH part can also be produced by separately preparing the HSA part and the 20K hGH part as recombinant proteins and binding them via either a peptide linker or a non-peptide linker. Herein, the term "peptide linker" refers to a peptide chain or its derivative which includes 1 to 50 amino acids and whose N-terminus and C-terminus are covalently bound to either HSA or 20K hGH to produce a fusion protein having a HSA part and a 20K hGH part by combining HSA and 20K hGH. As the peptide linker, those consisting of Gly-Ser, Gly-Gly-Ser, or the amino acid sequence set forth as SEQ ID NO:4 (these sequences are collectively referred to as basic sequences) and those including these sequences can be used. For example, those containing an amino acid sequence in which the basic sequences are repeated 2 to 10 times, those containing the amino acid sequence in which the basic sequences are repeated 2 to 6 times, those containing the amino acid sequence in which the basic sequences are repeated 3 to 5 times, and the like can be used. A preferable example of the amino acid sequence of the peptide linker includes the amino acid sequence set forth as SEQ ID NO:5. Further, the amino acid sequence of the peptide linker may be as such wherein one or more amino acids in the amino acid sequence set forth as SEQ ID NO:4 or SEQ ID NO:5 have been deleted, added, substituted by different amino acids, or the like.

"Non-peptide linker" is selected from polyethylene glycol (PEG), polypropylene glycol, a copolymer of ethylene glycol and propylene glycol, polyoxyethylated polyol, polyvinyl alcohol, polysaccharide, dextran, polyvinyl ether, biodegradable polymer, Lipid polymers, chitins, and hyaluronic acid, derivatives thereof, or a combination thereof. Non-peptide linker via functional groups in itself is covalently bound to both HSA and 20K hGH to produce a fusion protein having a HSA part and a 20K hGH part.

A fusion protein in which HSA and 20K hGH are bound together using PEG as a non-peptide linker is particularly referred to as HSA-PEG-20K hGH. HSA-PEG-20K hGH can be produced by bonding HSA and PEG to make HSA-PEG and then bonding the HSA-PEG and 20K hGH. Alternatively, HSA-PEG-20K hGH can also be produced by bonding 20K hGH and PEG to make 20K hGH-PEG and then bonding the 20K hGH-PEG with HSA. PEG modified with a functional group such as carbonate, carbonylimidazole, active ester of carboxylic acid, azlactone, cyclic imidothion, isocyanate, isothiocyanate, imidate, or aldehyde is used for bonding PEG with HSA and 20K hGH. To bond PEG to HSA and 20K hGH, PEG modified with functional groups such as carbonate, carbonyldiimidazole, active ester of carboxylic acid, azlactone, cyclic imidethione, isocyanate, isothiocyanate, imidate, aldehyde, or the like is employed. Such functional groups introduced to PEG react mainly with an amino group on the molecules of HSA and 20K hGH, let PEG form covalent bonds with HSA and 20K hGH. Though there is no notable limitation as to the molecular weight of the PEG employed, its mean molecular weight (MW) is as follows: preferably MW=500-60000, more preferably MW=500-20000. For example, PEG whose mean molecular weight is about 300, about 500, about 1000, about 2000, about 4000, about 10000, about 20000, or the like can preferably be used as a non-peptide linker.

HSA-PEG, for example, can be obtained by mixing HSA with a polyethylene glycol having aldehyde groups as functional groups (ALD-PEG-ALD) at a molar ratio HSA/(ALD-PEG-ALD) of 1:1, 1:2.5, 1:5, 1:10, 1:20, or the like, adding a reducing agent such as $NaCNBH_3$ to the mixture, and letting them react. HSA-PEG-20K hGH is then obtained by reacting HSA-PEG with 20K hGH in the presence of a reducing agent such as $NaCNBH_3$. Conversely, HSA-PEG-20K hGH can also be obtained by bonding 20K hGH with ALD-PEG-ALD to produce 20K hGH-PEG and then bonding 20K hGH-PEG with HSA.

The fusion protein of the present invention having a human serum albumin part and a 20K human growth hormone part has growth-promoting activity. The growth-promoting activity can be measured as cell proliferation activity by the assay method using BaF3/hGHR cells as described in Example 9. More specifically, the value of the $EC_{50}$ of the fusion protein is preferably 1.0 to 6.0 times, more preferably 1.5 to 2.5 times, still more preferably 1.6 to 2.3 times, and still more preferably 1.6 to 2.0 times as compared with that of 22K hGH, when measured by the assay method described in Example 9. According to the measurement method described in Example 9, the larger the $EC_{50}$ value is, the lower the cell proliferation activity is.

In one embodiment of the present invention, a fusion protein also has cell proliferation activity in which the C-terminus of the human serum albumin part and the N-terminus of the linker part are bound by a peptide bond and the C-terminus of the linker part and the N-terminus of the 20K human growth hormone part are bound by a peptide bond to form a single chain polypeptide. The fusion protein exhibits the same or lower cell proliferation activity as compared with 22K hGH when the activity has been measured by a measurement method using BaF3/hGHR cells as described in Example 9. More specifically, the value of the $EC_{50}$ of the fusion protein is preferably 1.0 to 2.5 times, more preferably 1.5 to 2.5 times, still more preferably 1.6 to 2.3 times, and still more preferably 1.6 to 2.0 times as compared with that of 22K hGH, when measured by the assay method described in Example 9.

The protein having the amino acid sequence set forth as SEQ ID NO:29 is an embodiment of the fusion protein in which the C-terminus of the human serum albumin part and the N-terminus of the 20K human growth hormone part are linked by peptide bonds. The value of $EC_{50}$ of this fusion protein is about $4.3 \times 10^{-3}$ nM when measured by the measurement method as described in Example 9. This value is 5.0 to 6.0 times as compared with the $EC_{50}$ value of 22K hGH.

The fusion protein having the amino acid sequence set forth SEQ ID NO:36 is one embodiment of the present invention, in which the C-terminus of the human serum albumin part and the N-terminus of the linker part are bound by a peptide bond, and the C-terminus of the linker part and the N-terminus of the 20K human growth hormone part are bound by a peptide bond to form a single chain polypeptide. The value of $EC_{50}$ of this fusion protein is about $1.5 \times 10^{-3}$ nM when measured by the measurement method as described in Example 9. This value is 1.6 to 2.0 times as compared with the $EC_{50}$ value of 22K hGH.

The fusion protein shows lower prolactin (PRL)-like activity as compared with 22K hGH when measured by a measurement method using BaF3/hPRLR cells as described in Example 11. More specifically, the value of the $EC_{50}$ of the fusion protein is preferably 5 to 22 times, more preferably to 18 times, still more preferably 12 to 15 times as compared with that of 22K hGH, when measured by the assay method described in Example 11. According to the measurement method described in Example 1, the larger the $EC_{50}$ value is, the lower prolactin-like activity is.

In one embodiment of the present invention, a fusion protein also has prolactin-like activity in which the C-terminus of the human serum albumin part and the N-terminus of the linker part are bound by a peptide bond and the C-terminus of the linker part and the N-terminus of the 20K human growth hormone part are bound by a peptide bond to form a single chain polypeptide. The fusion protein exhibits lower prolactin-like activity as compared with 22K hGH when the activity has been measured by a measurement method using BaF3/hGHR cells as described in Example 11. More specifically, the value of the $EC_{50}$ of the fusion protein is preferably 5 to 22 times, more preferably 5 to 20 times, still more preferably 10 to 18 times, and still more preferably 12 to 15 times as compared with that of 22K hGH, when measured by the assay method described in Example 11.

The protein having the amino acid sequence set forth as SEQ ID NO:29 is an embodiment of the fusion protein in which the C-terminus of the human serum albumin part and the N-terminus of the 20K human growth hormone part are linked by peptide bonds. The value of $EC_{50}$ of this fusion protein is about 1.5 nM when measured by the measurement method as described in Example 11. This value is 20 to 22 times as compared with the $EC_{50}$ value of 22K hGH.

The fusion protein having the amino acid sequence set forth SEQ ID NO:36 is an embodiment of the present invention, in which the C-terminus of the human serum albumin part and the N-terminus of the linker part are bound by a peptide bond, and the C-terminus of the linker part and the N-terminus of the 20K human growth hormone part are bound by a peptide bond to form a single chain polypeptide. The value of $EC_{50}$ of this fusion protein is about $9.6 \times 10^{-1}$ nM when measured by the measurement method as described in Example 11. This value is 12 to 15 times as compared with the $EC_{50}$ value of 22K hGH.

A fusion protein of the present invention having the human serum albumin part and the 20K human growth hormone part has an affinity for human growth hormone binding protein (hGHBP). The fusion protein exhibits a lower affinity for hGHBP as compared with 22K hGH when measured by the measurement method as described in Example 12. More specifically, the value of the $IC_{50}$ of the fusion protein is preferably 2.5 to 10 times, more preferably 3.0 to 7.0 times, and still more preferably 3.0 to 6.0 times as compared with that of 22K hGH, when measured by the assay method described in Example 12. According to the measurement method described in Example 12, the greater the value of $IC_{50}$ is, the lower the affinity for hGHBP is. It is noted that the hGHBP used in Example 12 is recombinant hGHBP prepared using *Escherichia coli* and does not have a sugar chain.

In one embodiment of the present invention, a fusion protein also has affinity for human growth hormone binding protein (hGHBP) in which the C-terminus of the human serum albumin part and the N-terminus of the linker part are bound by a peptide bond and the C-terminus of the linker part and the N-terminus of the 20K human growth hormone part are bound by a peptide bond to form a single chain polypeptide. The fusion protein exhibits lower affinity for hGHBP as compared with 22K hGH when the affinity has been measured by a measurement method described in Example 12. More specifically, the value of the $IC_{50}$ of the fusion protein is preferably 2.5 to 10 times, more preferably 3.0 to 7.0 times, still more preferably 3.0 to 6.0 times as compared with that of 22K hGH, when measured by the assay method described in Example 12.

The protein having the amino acid sequence set forth as SEQ ID NO:29 is an embodiment of a fusion protein in which the C-terminus of the human serum albumin part and the N-terminus of the 20K human growth hormone part are linked by peptide bonds. The $IC_{50}$ of the fusion protein value is 3.0 to 6.0 times as compared with that of 22K hGH, when measured by the assay method described in Example 12.

The fusion protein having the amino acid sequence set forth SEQ ID NO:36 is an embodiment of the present invention, in which the C-terminus of the human serum albumin part and the N-terminus of the linker part are bound by a peptide bond, and the C-terminus of the linker part and the N-terminus of the 20K human growth hormone part are bound by a peptide bond to form a single chain polypeptide. The value of $IC_{50}$ of this fusion protein is 3.0 to 6.0 times as compared with the $IC_{50}$ value of 22K hGH.

Namely, as the fusion protein of the present invention has a lower affinity for hGHBP as compared with 22K hGH, it is expected that the abundance ratio of that not binding to hGHBP shall increase in the blood when administered to a human. HGHBP inhibits the binding of human growth hormone to human growth hormone receptor present on the surface of the target cell by binding to human growth hormone. Therefore, it is expected that the fusion protein of the present invention having low affinity to hGHBP has to be affected little by hGHBP and exhibits relatively high growth-promoting activity when administered to a human. Further, since the stability of the fusion protein of the present invention in the blood is increased by the presence of the human serum albumin part, the fusion protein can exert high growth-promoting activity when administered to a human.

Strong signaling into cells via hPRLR has been known to proliferate breast cancer cells. Human growth hormone has prolactin-like activity via hPRLR. Since existing human growth hormone preparations containing 22K hGH as an active ingredient are quickly metabolized when administered to a human, their activity is not sustainedly maintained at a high level in the body with no risk to induce breast cancer. However, in the case of a long-lasting human growth hormone preparation capable of continuously exhibiting high growth-promoting activity in the body when administered to a human, its prolactin-like activity is also maintained high in the body, so possibility to trigger breast cancer arises. However, the fusion protein of the present invention can persistently exhibit high growth-promoting activity in vivo when administered to a human, while having low prolactin-like activity, can almost eliminate the risk of triggering breast cancer or reduce the risk.

The fusion protein of the present invention having the human serum albumin part and the 20K human growth hormone part can be used as a therapeutic agent for various short stature diseases. Such short stature diseases include growth hormone deficiency short stature, short stature in Turner's syndrome, short stature in SGA, short stature in chronic renal failure, short stature in Prader-Willie syndrome, short stature in achondroplasia, short stature in SHOX deficiency, or short stature in Noonan syndrome, all not accompanied by epiphyseal closure. In addition, the fusion protein of the present invention can be used as a therapeutic agent for various growth hormone secretion deficiencies. Such growth hormone secretory deficiencies include adult growth hormone secretion deficiency and the like. In addition, it can be used as a medicament for the treatment of consumption caused by AIDS, and consumption caused by anorexia, but not limited to those, also can be used as a therapeutic agent for the treatment of disorders with such symptoms that could be ameliorated by long-term application of physiological activities of growth hormone, such as growth-promotion activity including acceleration of chondrogenesis, acceleration of protein anabolism, and the like, as well as improvement of body composition and lipids metabolism.

A therapeutic agent containing the fusion protein of the present invention as an active ingredient can be supplied to a medical institution as a lyophilized product or as an aqueous liquid preparation. When prepared as an aqueous liquid formulation, the fusion protein can be supplied as a formulation dissolved in a solution containing a stabilizer, a buffer, and an isotonicity agent and filled in a vial or a syringe. A formulation filled in a syringe is commonly referred to as a pre-filled syringe formulation. The therapeutic agent containing the fusion protein of the present invention as an active ingredient can be administered to a human, for example, by subcutaneous or intramuscular injection.

EXAMPLES

While the present invention will be described in further detail below referring to examples, it is not intended that the present invention be limited to the examples.

[Example 1] Construction of pE-mIRES-GS-Puro

Figure 2:
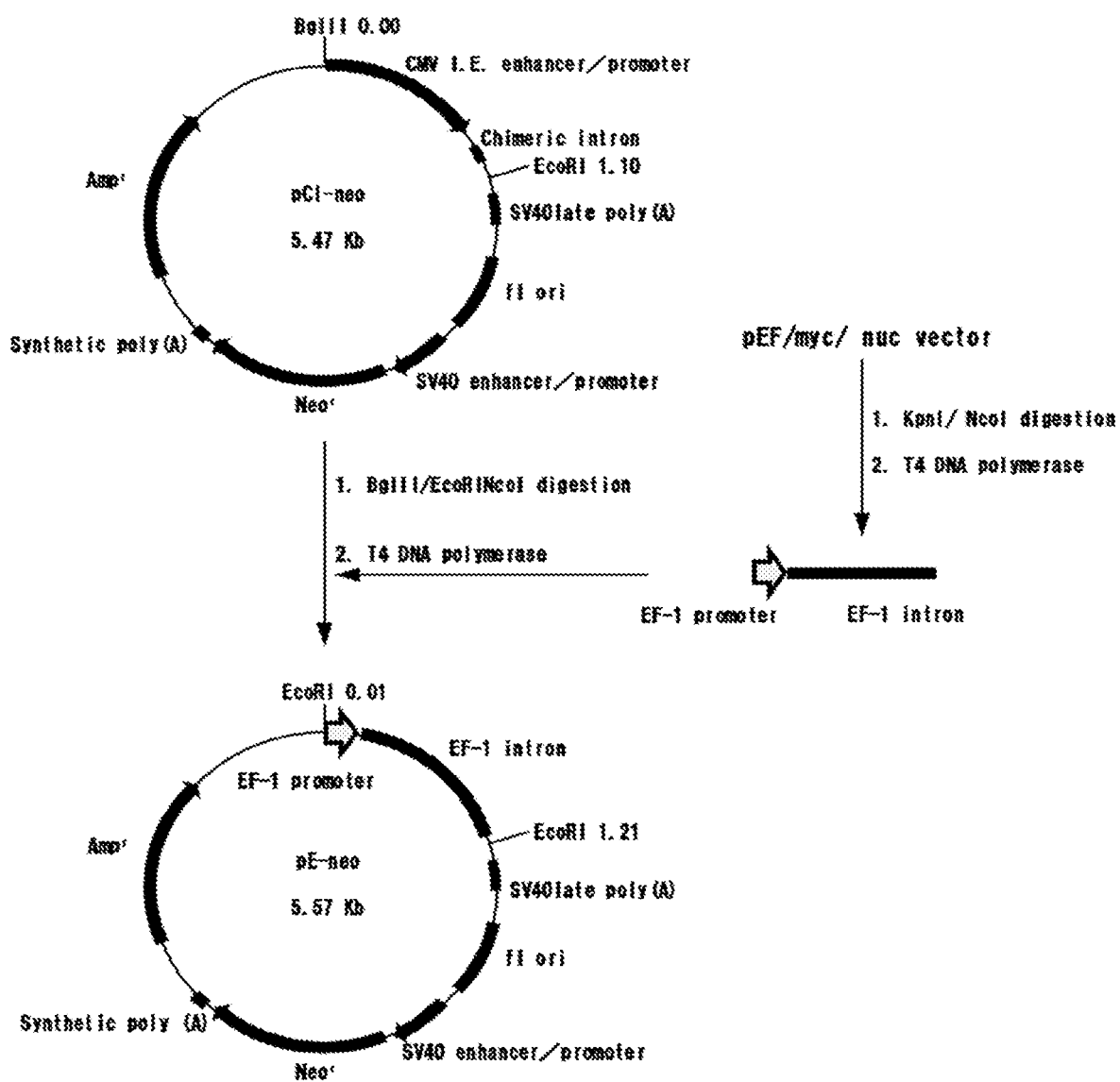
FIG. 2 A flow diagram of the method for construction of pE-neo vector.
Figure 3:
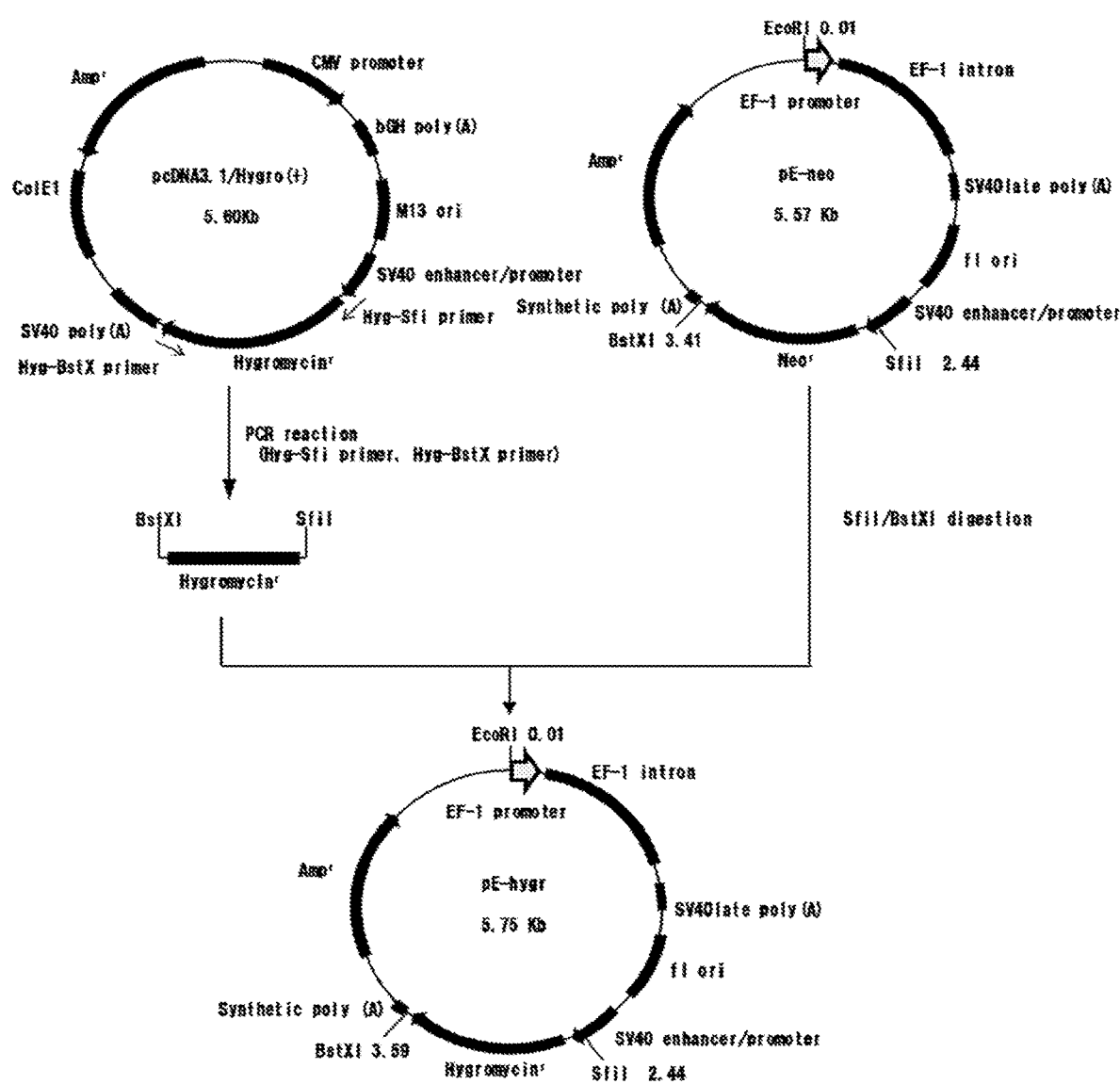
FIG. 3 A flow diagram of the method for construction of pE-hygr vector.

The pEF/myc/nuc vector (Invitrogen Inc.) was digested with restriction enzymes (KpnI and NcoI), a DNA fragment containing the EF-1α promoter and its first intron was excised, and this DNA fragment was blunt ended with T4 DNA polymerase. Separately, pCI-neo (Invitrogen Inc.) was digested with restriction enzymes (BglII and EcoRI), the region containing enhancer/promoter and intron of CMV was removed, and then blunt-ended with T4 DNA polymerase. Into this was inserted the above-mentioned region (after blunt-ended) including above-mentioned EF-1α promoter and its first intron to construct pE-neo vector (FIG. 2).

pE-neo vector was digested with SfiI and BstXI to cut out a region of about 1 kbp including a neomycin resistance gene (FIG. 3). The pE-neo vector was digested with restriction enzymes (SfiI and BstXI), and a region of about kbp containing the neomycin resistance gene was excised (FIG. 3). A hygromycin resistance gene was amplified by PCR using pcDNA3.1/Hygro(+) (Invitrogen Inc.), as a template, and primer Hyg-Sfi5' (SEQ ID NO:8) and primer Hyg-BstX3' (SEQ ID NO:9) (FIG. 3). The hygromycin gene thus amplified then was digested with SfiI and BstXI and inserted into the pE-neo vector mentioned above to construct pE-hygr vector (FIG. 3).

Figure 4A:
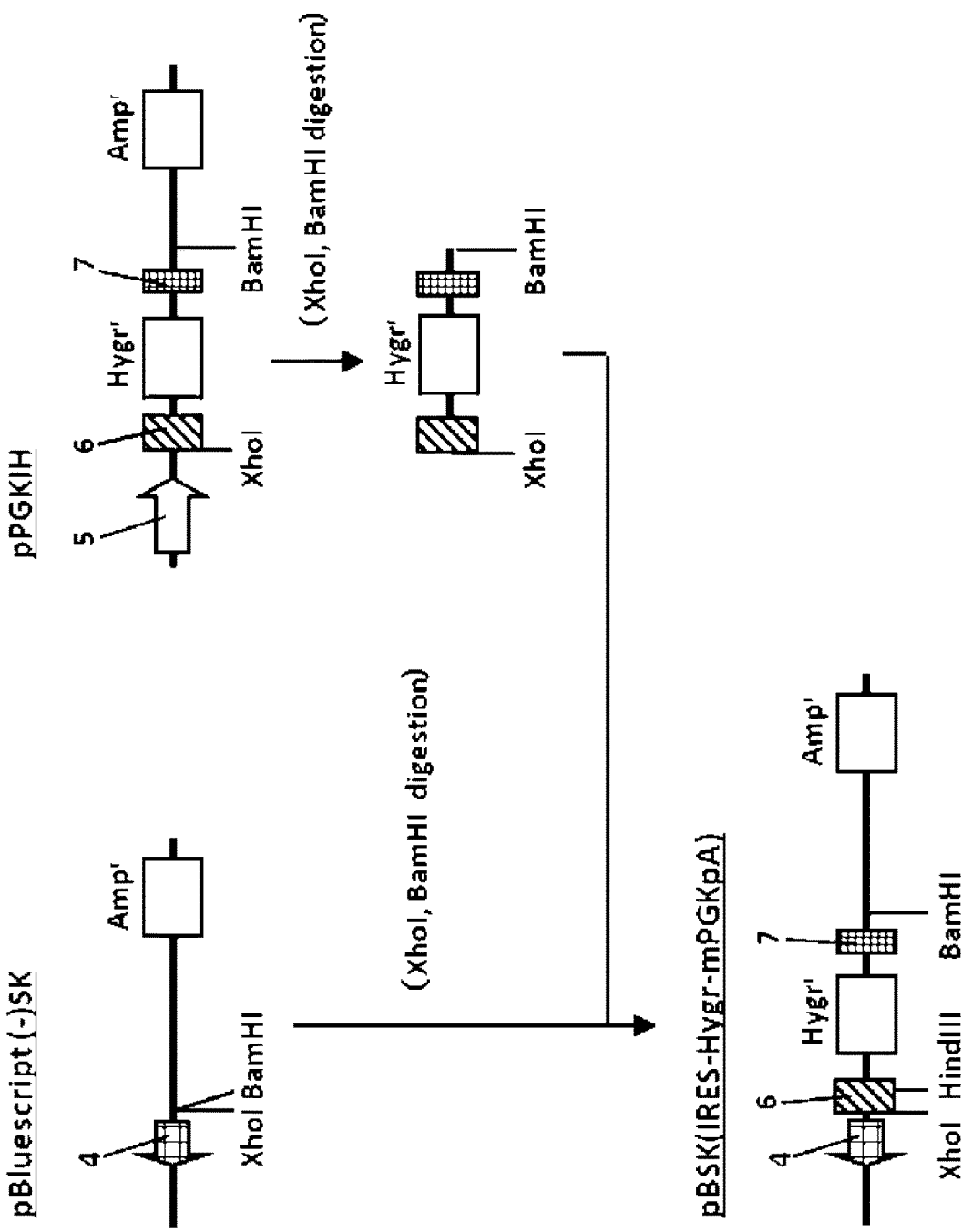
FIG. 4A A flow diagram of the method for construction of pE-IRES-GS-puro.

An expression vector pPGKIH (Miyahara M. et. al., J. Biol. Chem. 275, 613-618 (2000)) was digested with restriction enzymes (XhoI and BamHI) to cut out a DNA fragment consisting of a nucleotide sequence IRES-Hygr-mPGKpA, which included an internal ribosome entry site (IRES) derived from mouse encephalomyocarditis virus (EMCV), a hygromycin resistance gene (Hygr gene), and the polyadenylation region (mPGKpA) of mouse phosphoglycerate kinase (mPGK)(SEQ ID NO:10; from the 5' end, the region consisting of nucleotides 1-6 represents a "XhoI site"; the region consisting of nucleotides 120-715 and nucleotides 716-718 (atg) that follow represents a "nucleotide sequence including the internal ribosome entry site derived from the 5' untranslated region of mouse encephalomyocarditis virus"; the region consisting of nucleotides 716-1741 including in itself the nucleotides 716-718 (atg) represents the "nucleotide sequence encoding a hygromycin resistance gene"; the region consisting of nucleotides 1747-2210 represents a "nucleotide sequence including the polyadenylation region of mouse phosphoglycerate kinase"; and the region at the 3' end consisting of six nucleotides (nucleotides 2211-2216) represents a "BamHI site"). (Besides, the amino acid sequence corresponding to the Hygr gene is set forth as SEQ ID NO:11). This DNA fragment was inserted into pBluescript SK(-)(Stratagene Inc.) between its XhoI and BamHI sites, and the resulting product was designated as pBSK(IRES-Hygr-mPGKpA) (FIG. 4A).

Figure 4B:
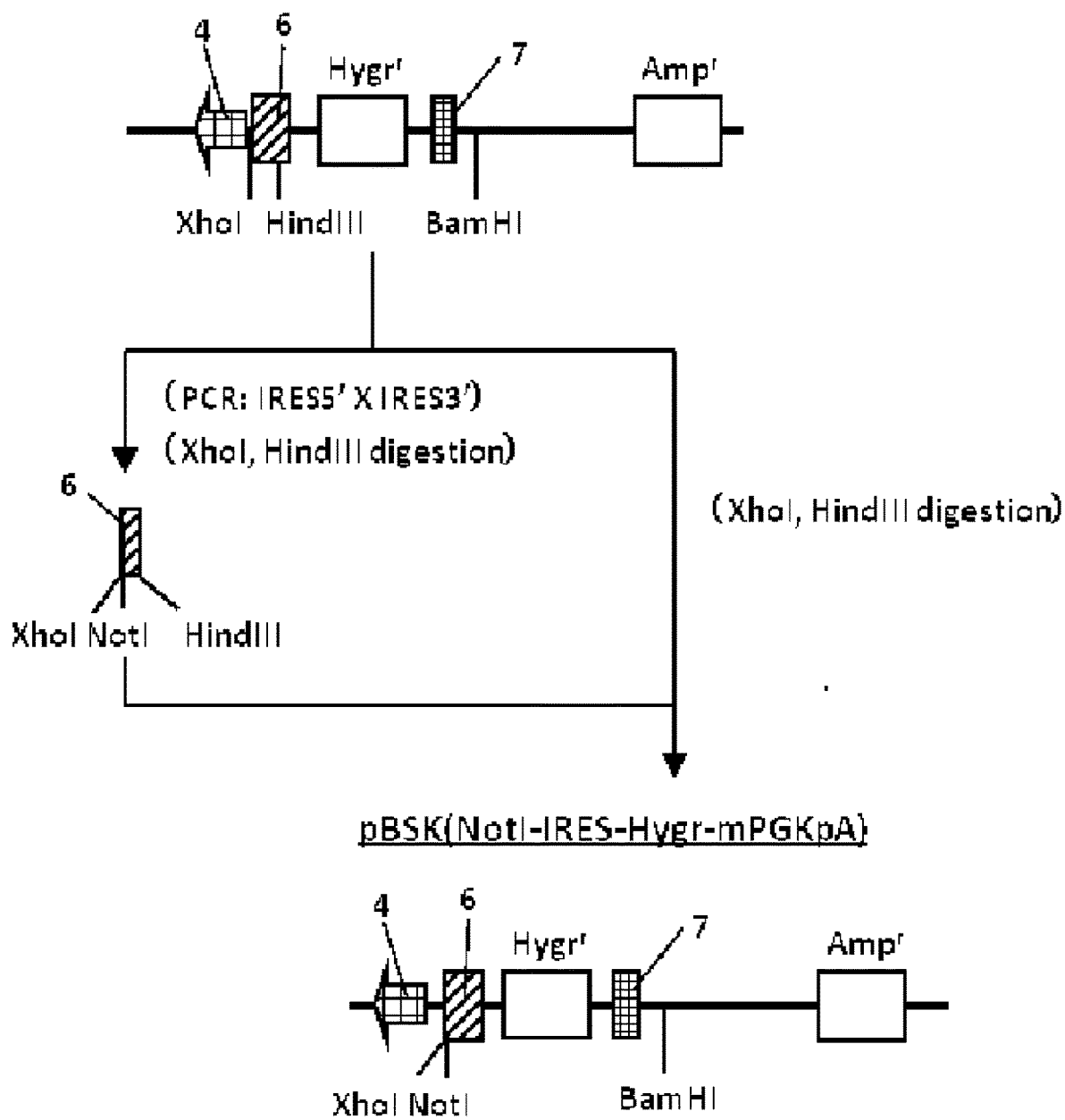
FIG. 4B A flow diagram of the method for construction of pE-IRES-GS-puro.
Figure 4C:
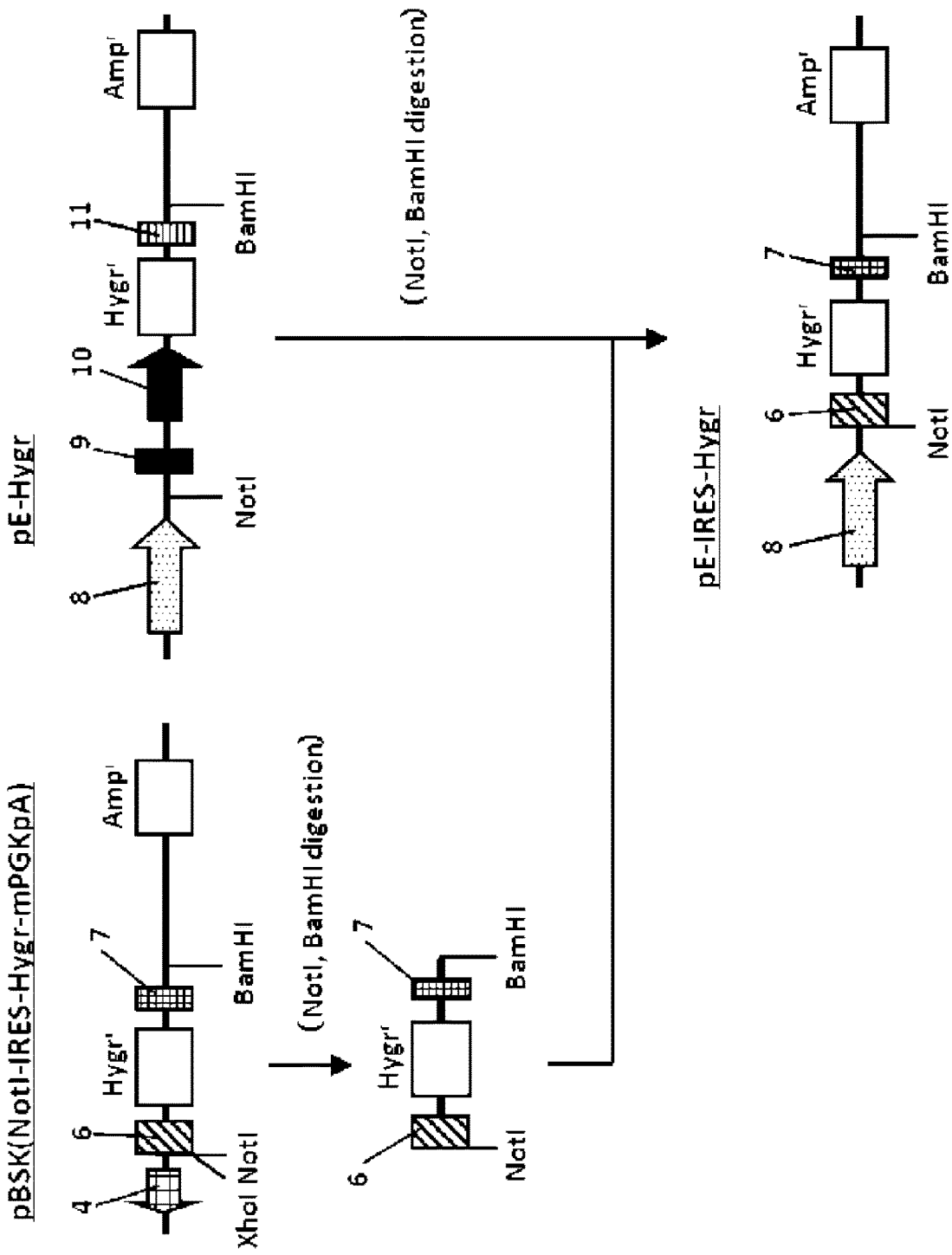
FIG. 4C A flow diagram of the method for construction of pE-IRES-GS-puro.
Figure 4D:
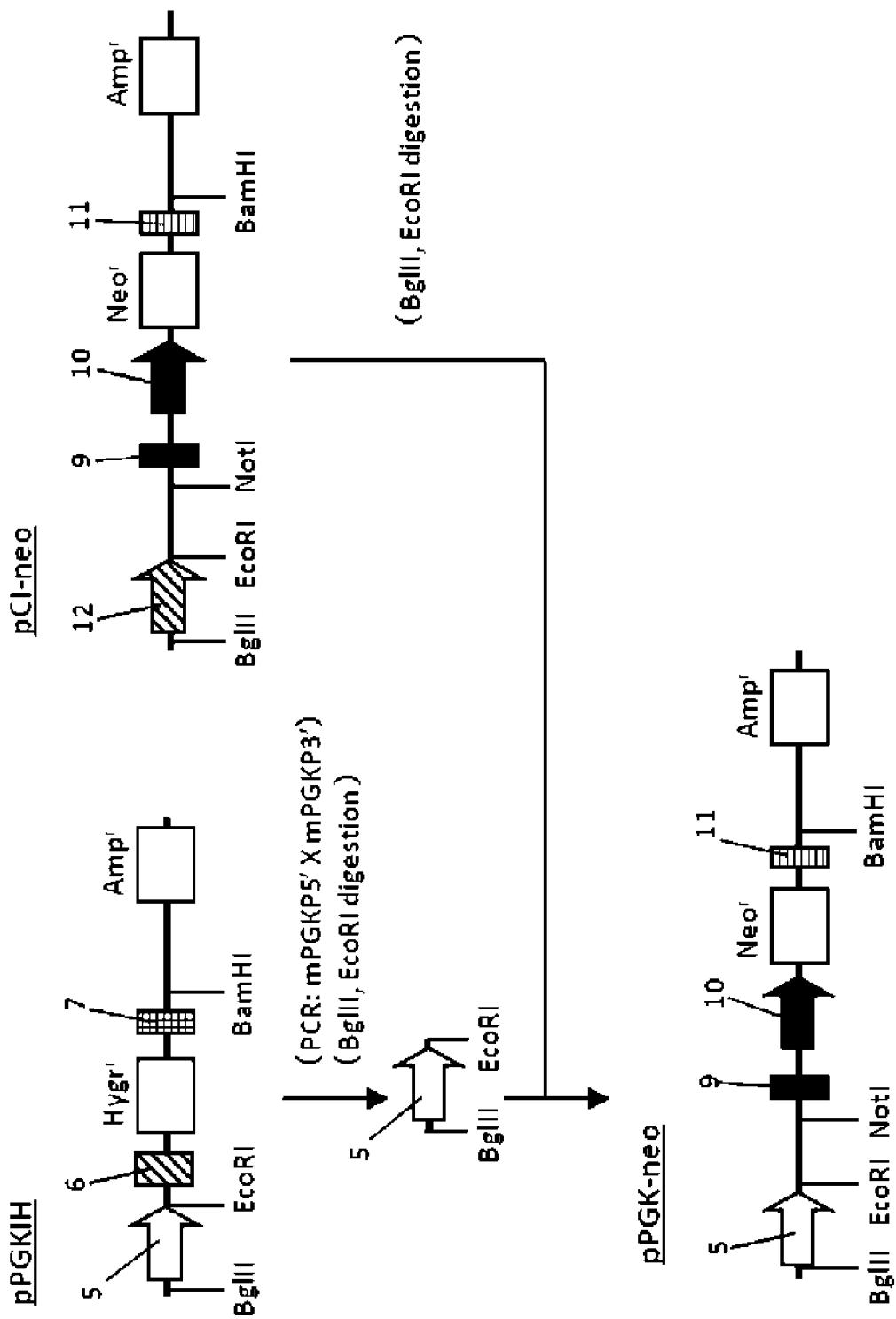
FIG. 4D A flow diagram of the method for construction of pE-IRES-GS-puro.

A DNA fragment containing part of the IRES of EMCV was amplified by PCR using pBSK (IRES-Hygr-mPGKpA), as a template, and primer IRES5' (SEQ ID NO:12) and primer IRES3' (SEQ ID NO:13). This fragment then was digested with restriction enzymes (XhoI and HindIII) and inserted into pBSK(IRES-Hygr-mPGKpA) between its XhoI and HindIII sites, and the resulting product was designated as pBSK(NotI-IRES-Hygr-mPGKpA)(FIG. 4B). pBSK(NotI-IRES-HygromPGKpA) was digested with restriction enzymes (NotI and BamHI) and inserted into the pE-hygr vector between its NotI and BamHI sites, and the resulting product was designated as plasmid pE-IRES-Hygr (FIG. 4C).

Figure 4E:
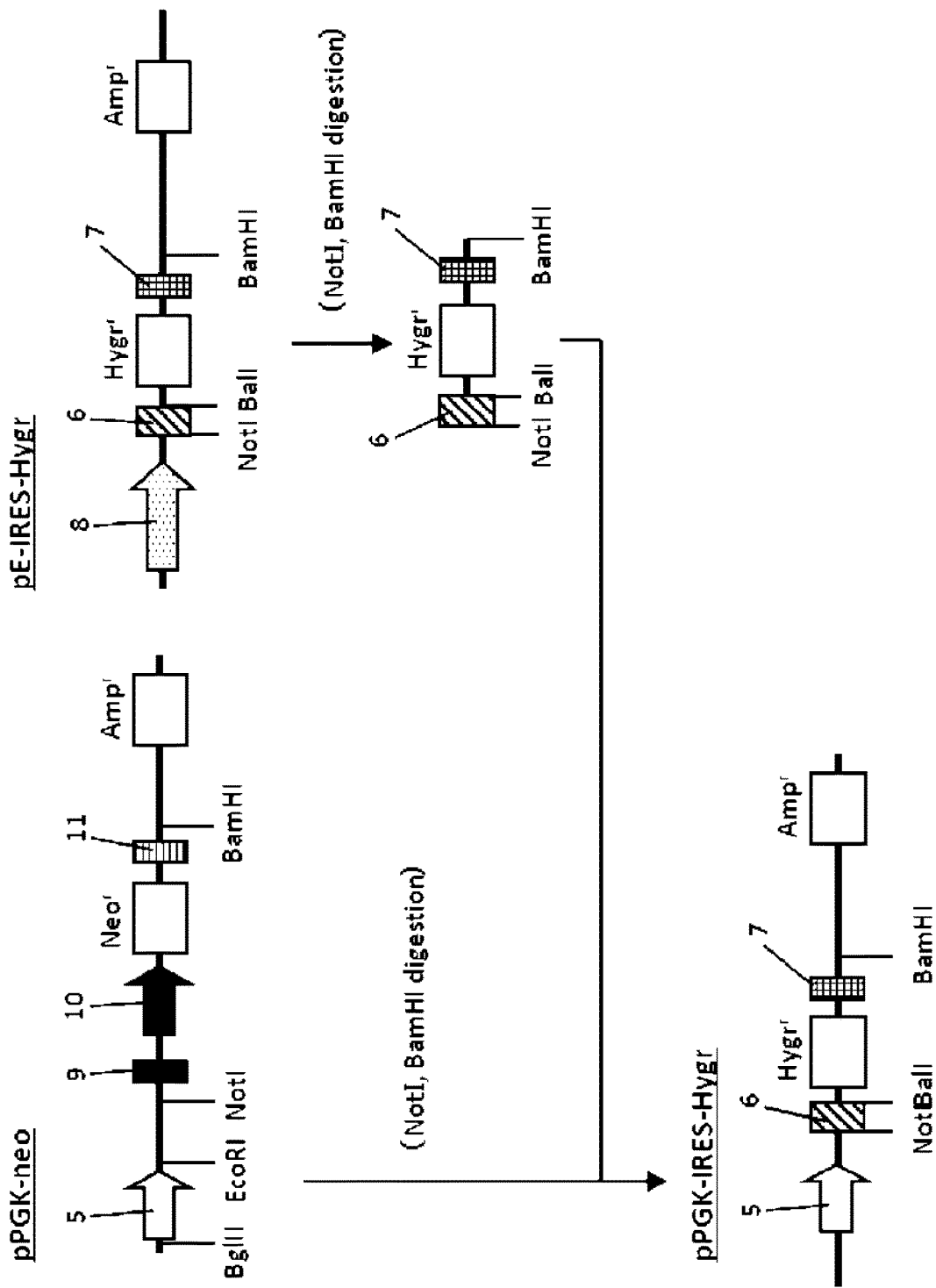
FIG. 4E A flow diagram of the method for construction of pE-IRES-GS-puro.
Figure 4F:
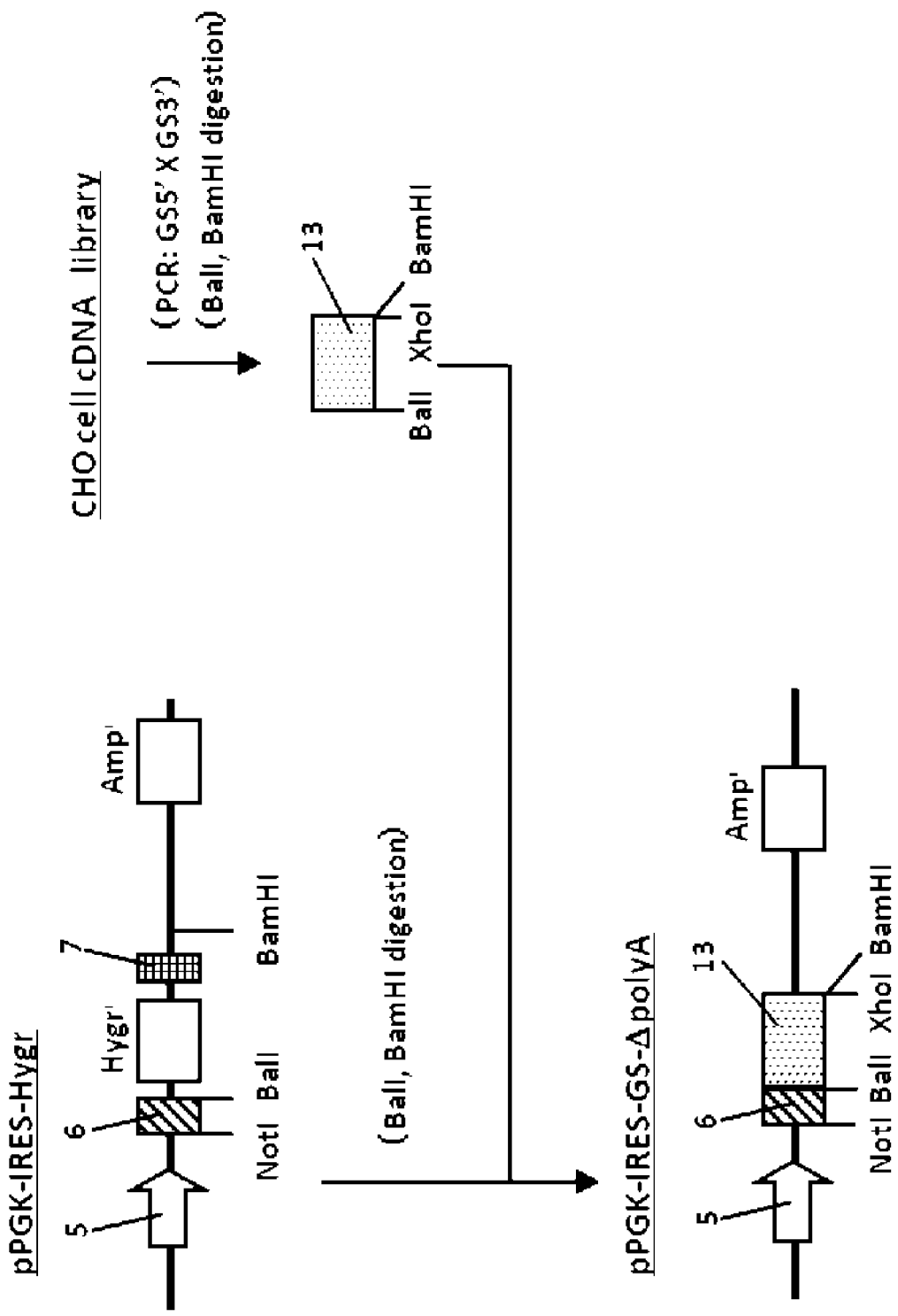
FIG. 4F A flow diagram of the method for construction of pE-IRES-GS-puro.

Using the expression vector pPGKIH, as a template, and primer mPGKP5' (SEQ ID NO:14) and primer mPGKP3' (SEQ ID NO:15), PCR was performed to amplify a DNA fragment consisting of a nucleotide sequence including the promoter region of mPGK (mPGKp)(SEQ ID NO:16, from the 5' end, nucleotides 4-9 represents a "BglII site", the region that follows consisting of nucleotides 10-516 represents a "nucleotide sequence including the promoter region of mouse phosphoglycerate kinase (mPGKp)", and the region that follows consisting of nucleotides 524-529 represents an "EcoRI site"). This DNA fragment then was digested with restriction enzymes (BglII and EcoRI) and inserted into pCI-neo (Promega Inc.) between its BglII and EcoRI sites, and the resulting product was designated as pPGK-neo (FIG. 4-4). pE-IRES-Hygr was digested with restriction enzymes (NotI and BamHI) to cut out a DNA fragment (IRES-Hygr), and this was inserted into pPGK-neo between its NotI and BamHI sites. The resulting product was designated as pPGK-IRES-Hygr (FIG. 4E).

cDNA was prepared from CHO-K1 cells, and using it as a template, and primer GS5' (SEQ ID NO:17) and primer GS3' (SEQ ID NO:18), PCR was performed to amplify a DNA fragment including the GS gene. This DNA fragment was digested with restriction enzymes (BalI and BamHI) and inserted into pPGK-IRES-Hygr between its BalI and BamHI sites. The resulting product was designated as pPGK-IRES-GS-ΔpolyA (FIG. 4F).

Figure 4G:
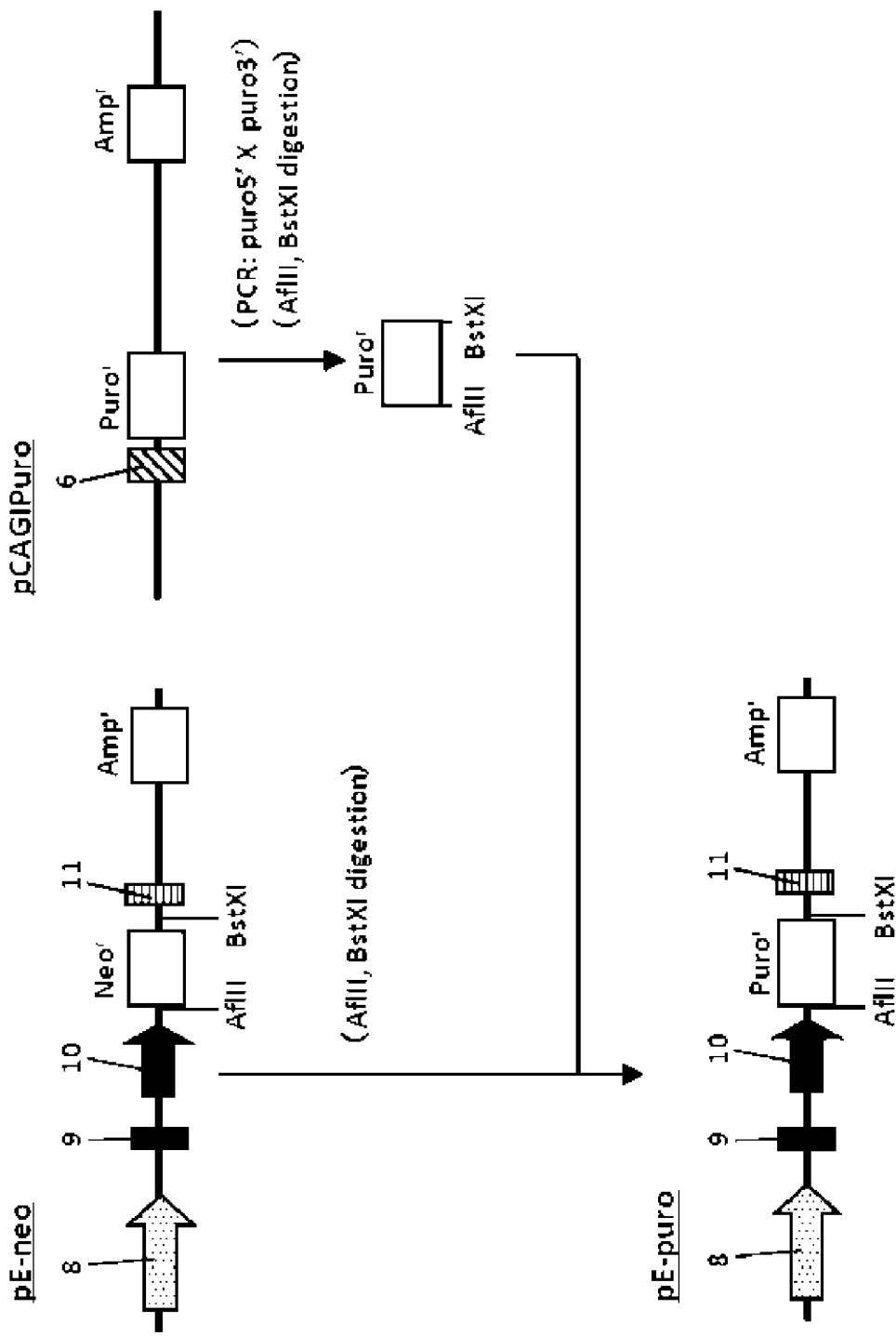
FIG. 4G A flow diagram of the method for construction of pE-IRES-GS-puro.
Figure 4H:
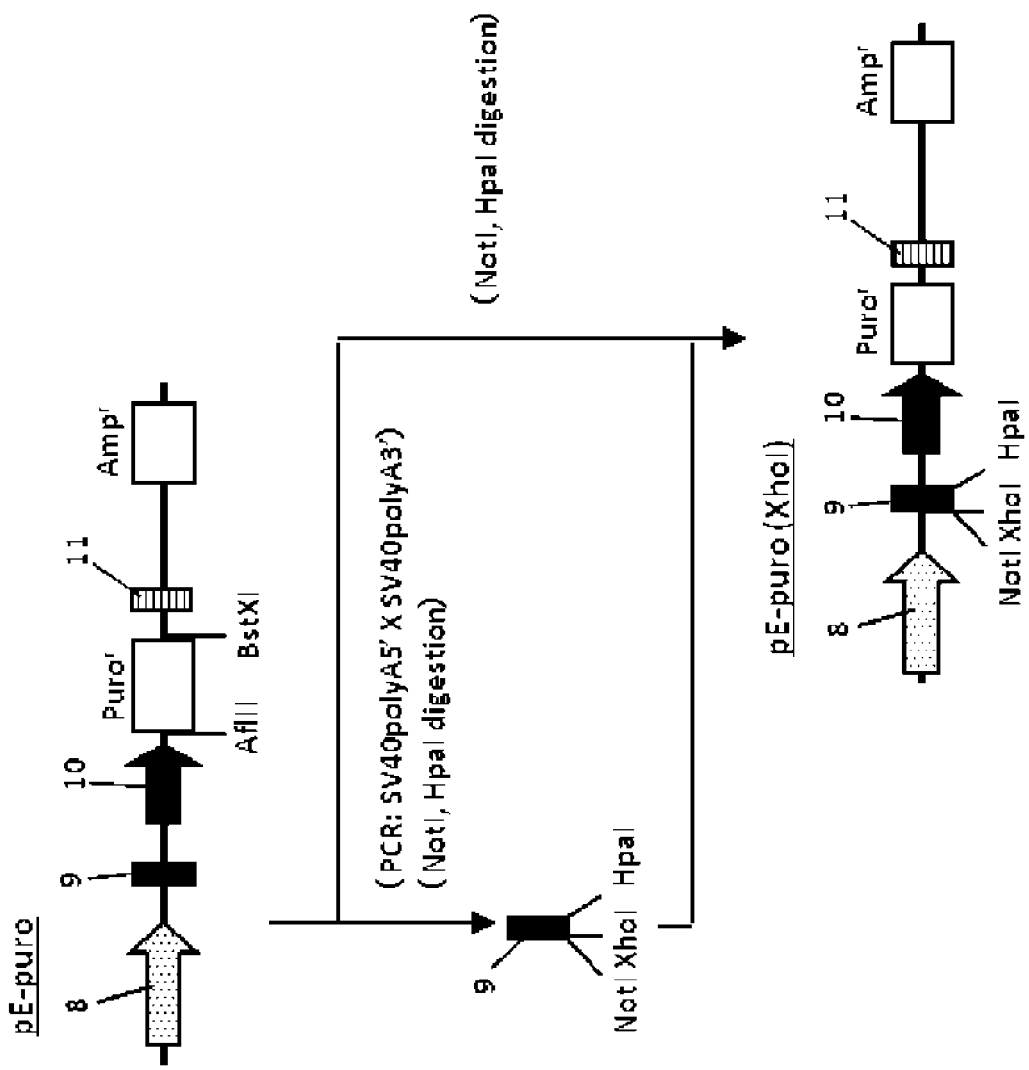
FIG. 4H A flow diagram of the method for construction of pE-IRES-GS-puro.

Using pCAGIPuro (Miyahara M. et. al., J. Biol. Chem. 275, 613-618 (2000)), as a template, and primer puro5' (SEQ ID NO:19) and primer puro3' (SEQ ID NO:20), PCR was performed to amplify a nucleotide sequence including a puromycin resistance gene (puro gene) (SEQ ID NO:21, from the 5'-end, the region consisting of nucleotides 2-7 represents a "AflII" site, the region that follows consisting of nucleotides 8-607 represents a "nucleotide sequence encoding the puromycin resistance gene (puro gene)", and the region that follows consisting of nucleotides 608-619 represents a "BstXI site") (Besides, the amino acid sequence corresponding to the puro gene is set forth as SEQ ID NO:22). This DNA fragment was digested with restriction enzymes (AflII and BstXI) and inserted into the expression vector pE-neo between its AflII and BstXI sites. The resulting product was designated as pE-puro (FIG. 4G).

Figure 4I:
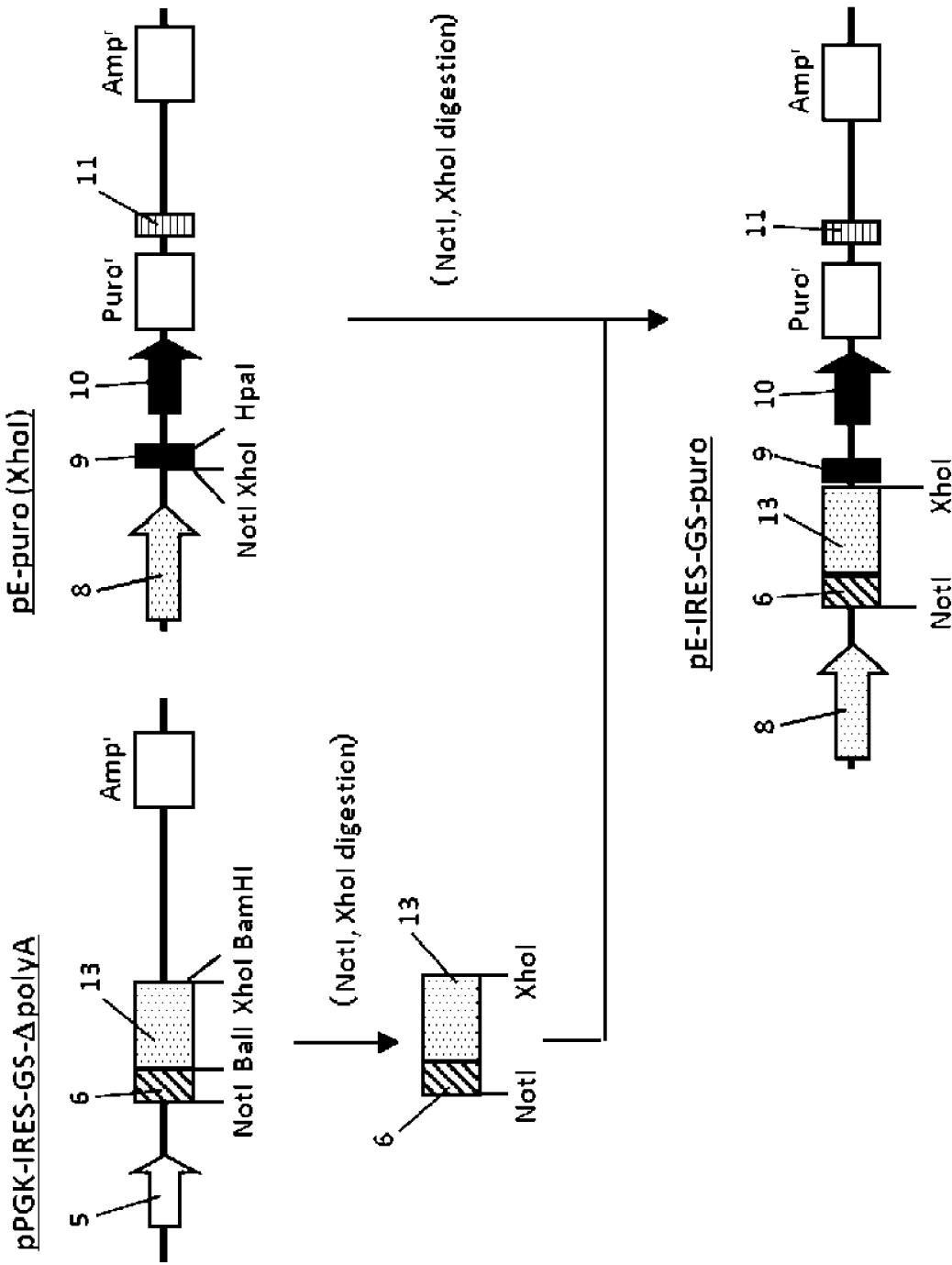
FIG. 4I A flow diagram of the method for construction of pE-IRES-GS-puro.

Using pE-puro, as a template, and primer SV40polyA5' (SEQ ID NO:23) and primer SV40polyA3' (SEQ ID NO:24), PCR was performed to amplify a DNA fragment including SV40 late polyadenylation region. This DNA fragment then was digested with restriction enzymes (NotI and HpaI) and inserted into pE-puro between its NotI and HpaI sites. The resulting product was designated as pE-puro (XhoI) (FIG. 4H). pPGK-IRES-GS-ΔpolyA was digested with restriction enzymes (NotI and XhoI) to cut out a DNA fragment including the IRES-GS region, which then was inserted into the expression vector pE-puro(XhoI) between its NotI and XhoI sites. The resulting product was designated as pE-IRES-GS-puro (FIG. 4I).

Figure 5:
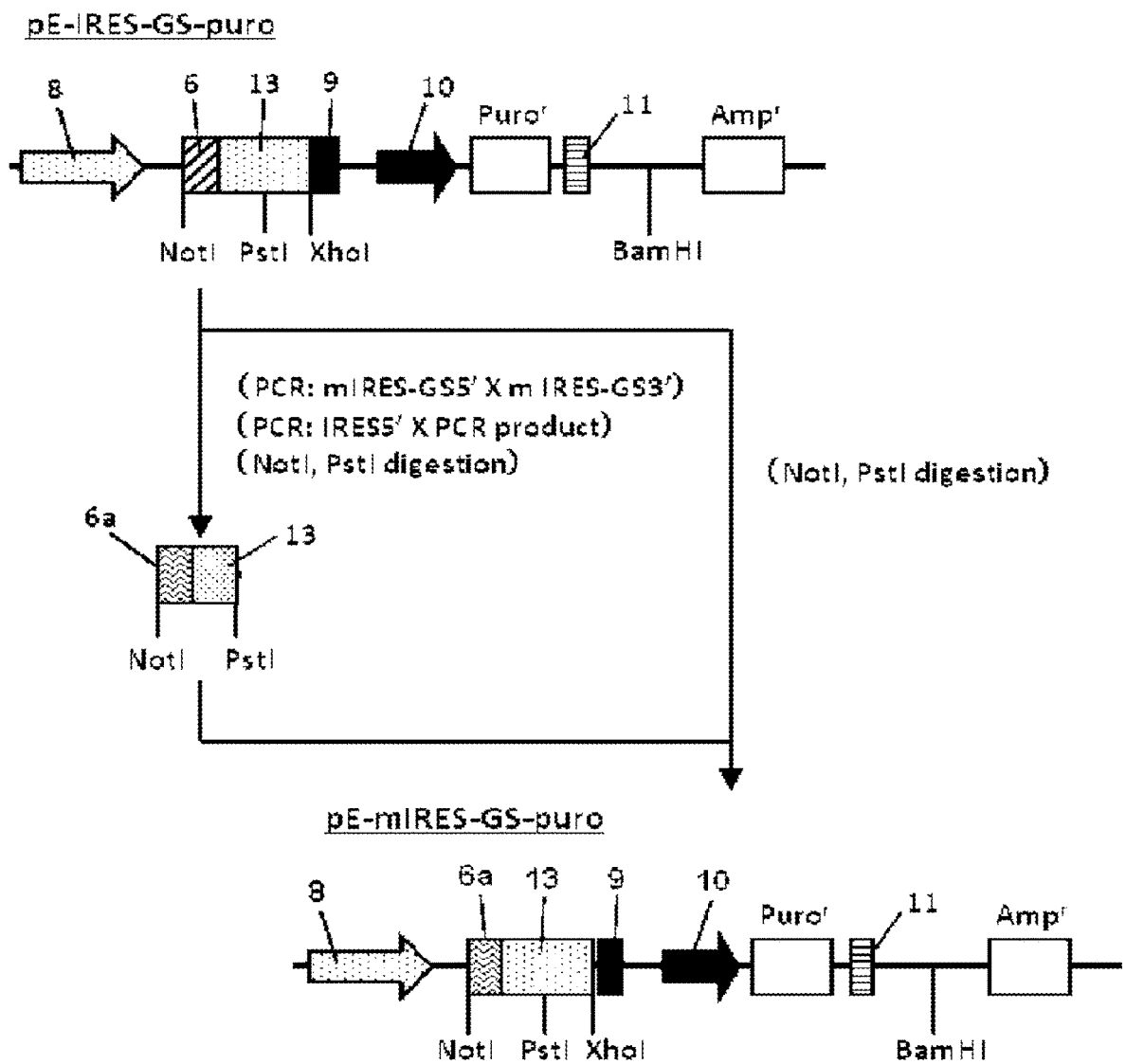
FIG. 5 A flow diagram of the method for construction of pE-mIRES-GS-puro.

Using the expression vector pE-IRES-GS-puro, as a template, and primer mIRES-GS5' (SEQ ID NO:25) and primer mIRES-GS3' (SEQ ID NO:26), PCR was performed to amplify a region from the IRES of EMCV to GS, and thus a DNA fragment was amplified in which the second start codon (ATG) from the 5' end of the IRES of EMCV was destroyed by introduction of a mutation. Using the expression vector pE-IRES-GS-puro, as a template, and the DNA fragment and the above-mentioned primer IRES5', PCR was performed to amplify a DNA fragment including the above-mentioned region from IRES to GS. This DNA fragment was digested with restriction enzymes (NotI and PstI), and a DNA fragment thus cut out was inserted into the expression vector pE-IRES-GS-puro between its NotI and PstI sites. The resulting product was designated as pE-mIRES-GS-puro, an expression vector for mammalian cells (FIG. 5).

[Example 2] Construction of HSA-22K hGH Expression Vector

Figure 6:
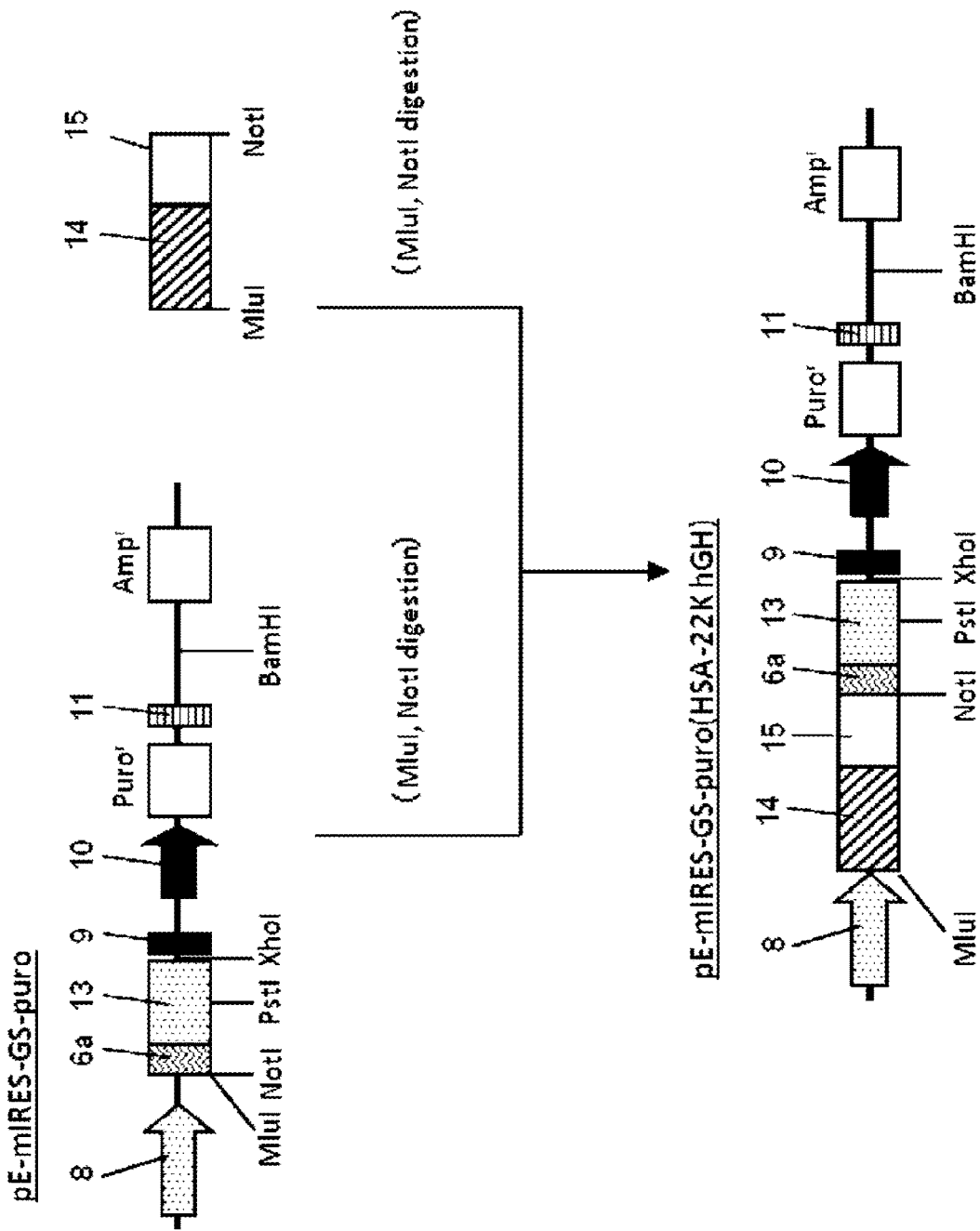
FIG. 6 A flow diagram of the method for construction of HSA-22K hGH expression vector (pE-mIRES-GS-puro (HSA-22KhGH))

A fusion protein having the amino acid sequence set forth as SEQ ID NO:27 in which the C-terminus of HSA and the N-terminus of 22K hGH were fused was designated as HSA-22K hGH. In the amino acid sequence set forth as SEQ ID NO:27, the amino acids at positions 1 to 585 correspond to the amino acid sequence of HSA, and the amino acids at positions 586 to 776 correspond to the amino acid sequence of 22K hGH. A DNA which had a nucleotide sequence set forth as SEQ ID NO:28 containing a gene encoding HSA-22K hGH (HSA-22K hGH gene) was chemically synthesized. This DNA was digested with restriction enzymes (MluI and NotI) and inserted between MluI and NotI sites of pE-mIRES-GS-puro prepared in Example 1 to construct pE-mIRES-GS-puro(HSA-22K hGH), an expression vector for HSA-22K hGH. FIG. 6 shows the schematic structure of pE-mIRES-GS-puro (HSA-22 K hGH).

[Example 3] Construction of HSA-20K hGH Expression Vector

Figure 7:
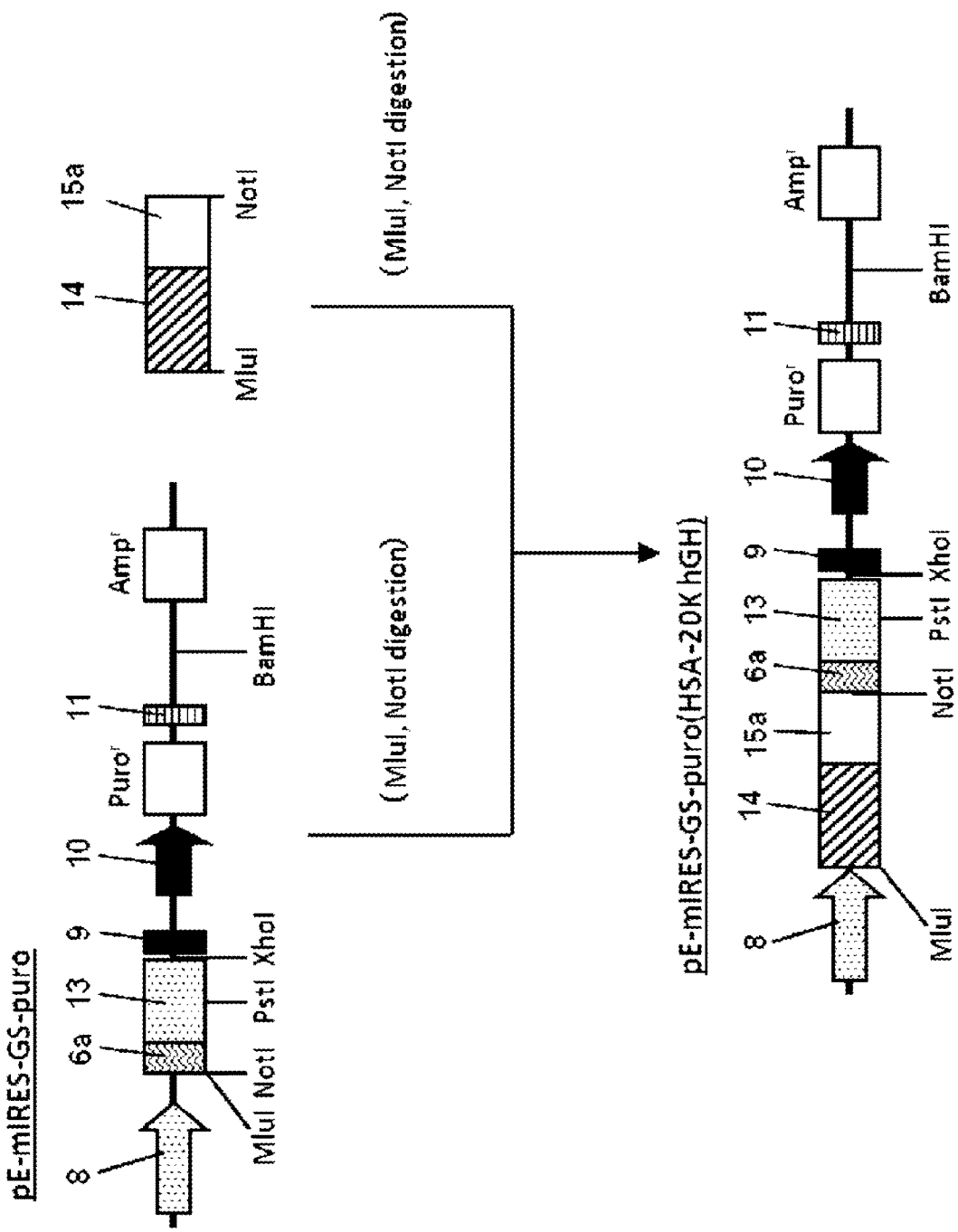
FIG. 7 A flow diagram of the method for construction of HSA-20K hGH expression vector (pE-mIRES-GS-puro (HSA-20KhGH))

A fusion protein having the amino acid set forth as SEQ ID NO:29 in which the C-terminus of HSA and the N-terminus of 20K hGH were fused was designated as HSA-20K hGH. In the amino acid sequence set forth as SEQ ID NO: 29, the amino acids at positions 1 to 585 correspond to the amino acid sequence of HSA, and the amino acids at positions 586 to 761 positions correspond to the amino acid sequence of 20K hGH. PCR was carried out using pE-mIRES-GS-puro (HSA-22K hGH) constructed in Example 2 as a template, and primer YA055 (SEQ ID NO:30) and primer YA056 (SEQ ID NO:31). The obtained PCR product then was subjected to agarose gel electrophoresis, the amplified target DNA fragment was purified with QIAEX II (QIAGEN Inc.), and this DNA fragment was used as a megaprimer. Subsequently, PCR was carried out using pE-mIRES-GS-puro (HSA-22K hGH) as a template, and primer YA 036 (SEQ ID NO:32) and the megaprimer to amplify a DNA fragment having the nucleotide sequence set forth as SEQ ID NO:33 which contained the gene encoding HSA-20K hGH (HSA-20K hGH gene). The obtained PCR product was digested with restriction enzymes (MluI and NotI) and incorporated between MluI and NotI sites of pE-mIRES-GS-puro prepared in Example 1 to construct pE-mIRES-GS-puro(HSA-20KhGH), an expression vector for HSA-20K hGH. FIG. 7 shows the schematic structure of pE-mIRES-GS-puro (HSA-20KhGH).

[Example 4] Construction of HSA-[Linker]-20K hGH Expression Vector

A fusion protein having the amino acid set forth as SEQ ID NO:36 in which the C-terminus of HSA and the N-terminus of 20K hGH were fused via a peptide linker having the amino acid sequence set forth as SEQ ID NO:5 was designated as HSA-[linker]-20K hGH. In the amino acid sequence set forth as SEQ ID NO:36, the amino acids at positions 1 to 585 correspond to the amino acid sequence of HSA, the amino acids at positions 586 to 605 correspond to the amino acid sequence of the peptide linker, and the amino acids at positions 606 to 781 correspond to the amino acid sequence of 20K hGH. PCR was carried out using pE-mIRES-GS-puro(HSA-20KhGH) as a template, and primer YA036 (SEQ ID NO:32) and primer YA065 (SEQ ID NO:34) to amplify a DNA fragment containing a gene encoding HSA-[linker] portion. The obtained PCR product was digested with restriction enzymes (MluI and BamHI), subjected to agarose gel electrophoresis, and the DNA fragment containing the gene encoding HSA-[linker] portion was purified with QIAEX II (QIAGEN Inc.). In addition, PCR was carried out using pE-mIRES-GS-puro (HSA-20KhGH) as a template, and primer YA066 (SEQ ID NO:35) and primer YA056 (SEQ ID NO:31) to amplify a DNA fragment containing 20K hGH gene. The obtained PCR product was digested with restriction enzymes (BamHI and NotI), subjected to agarose gel electrophoresis, and the DNA fragment containing the 20K hGH gene was purified with QIAEX II.

Figure 8:
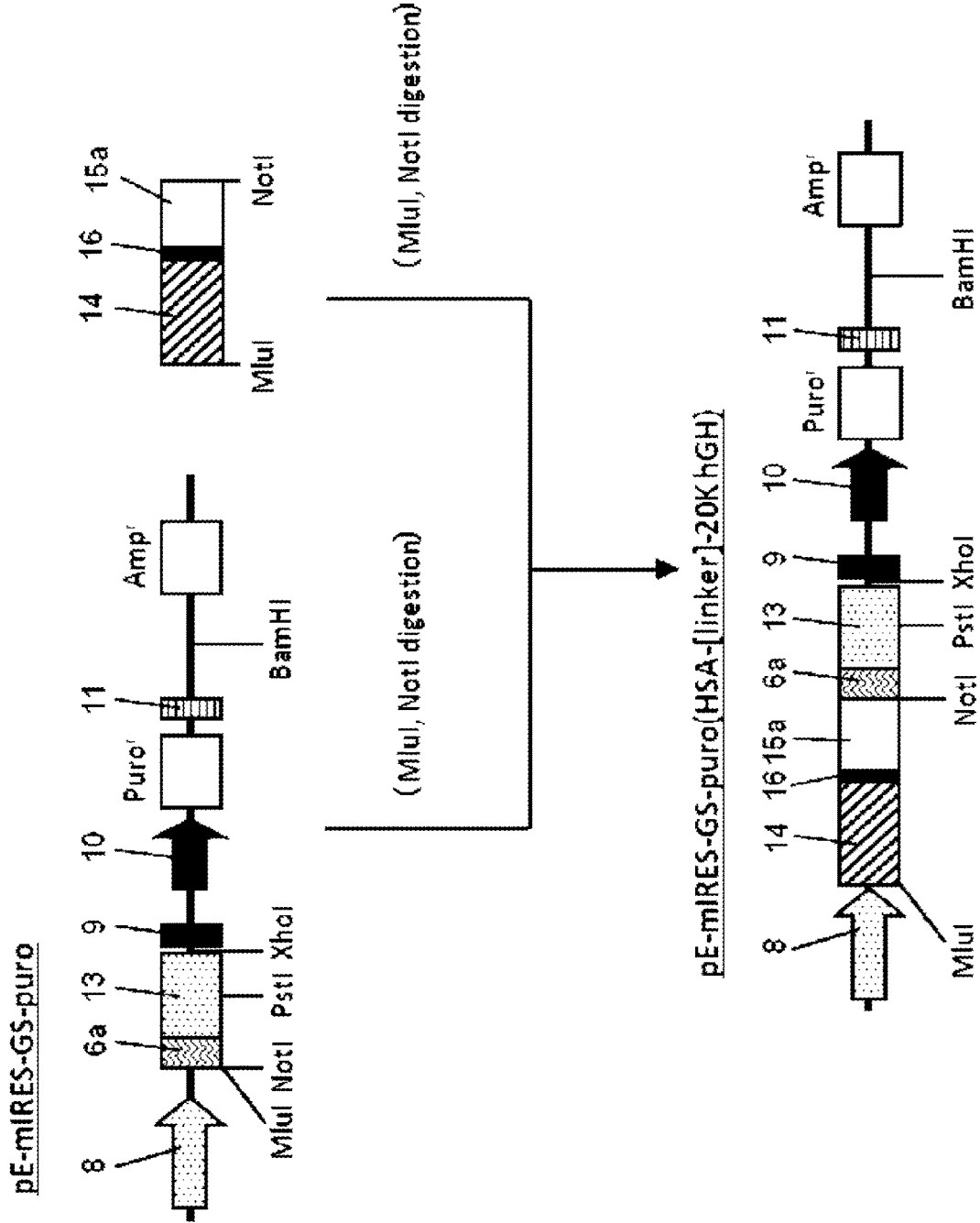
FIG. 8 A flow diagram of the method for construction of HSA-[linker]-20K hGH expression vector (pE-mIRES-GS-puro(HSA-[linker]-20KhGH))

The DNA fragments thus prepared which contained either the gene encoding the HSA-[linker] portion or the DNA fragment containing the 20K hGH gene were mixed and ligated with pE-mIRES-GS-puro already digested with restriction enzymes (MluI and NotI) to incorporate a DNA fragment having the nucleic acid sequence set forth as SEQ ID:36 in which the DNA fragment containing 20K hGH gene is bound downstream of the DNA fragment containing the gene encoding the HSA-[linker] portion, resulting in the construction of pE-mIRES-GS-puro(HSA-[linker]-20KhGH), an expression vector for HSA-[linker]-20K hGH. FIG. 8 shows the schematic structure of pE-mIRES-GS-puro (HSA-[linker]-20KhGH).

The pE-mIRES-GS-puro(HSA-22KhGH), pE-mIRES-GS-puro(HSA-20KhGH) and pE-mIRES-GS-puro(HSA-[linker]-20KhGH) prepared in Examples 2 to 4 were collectively referred to as HSA-hGH expression vectors.

[Example 5] Preparation of Cells for Expression of HSA-hGH Fusion Protein

Using the Gene Pulser Xcell electroporation system (Bio Rad Inc.), CHO-K1 cells, a cell derived from the ovary of Chinese hamster, were transfected with one of pE-mIRES-GS-puro(HSA-22KhGH), the expression vector for HSA-22K hGH, pE-mIRES-GS-puro(HSA-20KhGH), the expression vector for HSA-20K hGH, or pE-mIRES-GS-puro (HSA-[linker]-20KhGH), the expression vector for HSA-[linker]-20K hGH. The cells into which one of the expression vectors had been introduced were subjected to selection culture using CD OptiCHO™ medium (Thermo Fisher Scientific Inc.) containing methionine sulfoximine (SIGMA Inc.) and puromycin (SIGMA Inc.) to establish cells for expression of HSA-22K hGH, cells for expression of HSA-20K hGH, and cells for expression of HSA-[linker]-20K hGH, respectively. During the selection culture, the concentrations of methionine sulfoximine and puromycin were increased in a step wise manner, up to the final concentration of 300 μM for methionine sulfoximine, and 10 μg/mL for puromycin, to selectively promote the cells having stronger drug resistance.

The cells for expressing HSA-22K hGH, the cells for expressing HSA-20K hGH, and the cells for expressing HSA-[linker]-20K hGH were collectively referred to as cells for expressing HSA-hGH fusion protein. And the HSA-hGH fusion proteins obtained by culturing the cells for expressing HSA-hGH fusion protein were collectively referred to as HSA-hGH fusion proteins.

[Example 6] Culture of Cells Expressing HSA-hGH Fusion Protein

Methionine sulfoximine and puromycin were added to CD OptiCHO™ medium (Thermo Fisher Scientific Inc.) to prepare a cell culture medium at concentrations of 300 μM and 10 μg/mL, respectively. Each of HSA-22K hGH-expressing cells, HSA-20K hGH-expressing cells, and HSA-[linker]-20K hGH-expressing cells prepared in Example 5 were added to the cell culture medium at a cell density of $2 \times 10^5$ cells/mL, and cultured at 37° C. under 5% $CO_2$. The cells were subcultured by adding the cells to a fresh culture medium at the cell density of $2 \times 10^5$ cells/mL every 5 days.

[Example 7] Purification of HSA-hGH Fusion Protein

Each of HSA-22K hGH-expressing cells, HSA-20K hGH-expressing cells, and HSA-[linker]-20K hGH-expressing cells were suspended in the cell culture medium at a density of $2 \times 10^5$ cells/mL so that the total amount was to be 240 mL. 30 mL of each of these cell suspensions was added to eight dishes with a diameter of 15 cm and cultured at 37° C. under 5% $CO_2$ for 5 days. After completion of the culture, the medium was recovered and filtered with a membrane filter (pore size 0.22 μm, Millipore Inc.) to prepare a culture supernatant. To each of culture supernatants thus prepared, 1 M Tris-HCl (pH 8.0) or acetic acid was added to adjust the pH to 7.0 to 7.2.

A resin (Capture Select™ anti-hGH resin, Thermo Fisher Scientific Inc.), in which 5 mL of an anti-human growth hormone antibody was bound, was packed in a column made of polypropylene (Polyprep™ column, Bio-Rad Inc.) and equilibrated with 5 column volume of 10 mM Tris-HCl buffer (pH 8.0) containing 500 mM NaCl. And then, each of the culture supernatants whose pH was adjusted as described above was loaded on the column at a flow rate of about 2.5 mL/min to adsorb the HSA-hGH fusion protein to the resin. Subsequently, at the same flow rate, the column was washed with 5 column volumes of 10 mM Tris-HCl buffer (pH 8.0) containing 500 mM NaCl. And then, each of the HSA-hGH fusion proteins was eluted from the resin with 5 column volumes of 0.1 M glycine buffer (pH 3.0). Eluted fractions containing the HSA-hGH fusion protein were collected and immediately the pH was adjusted to about 6.5 by adding 1 M HEPES buffer (pH 8.0) containing 2 M NaCl. The concentrations of HSA-hGH fusion proteins contained in the eluted fractions were measured by a Pierce™ BCA Protein Assay Kit (Thermo Fisher Scientific Inc.) using BSA as a standard substance.

[Example 8] Preparation of BaF3/hGHR Cells

BaF3/hGHR cells having acquired GH-dependent growth ability was produced by introducing of human GH receptor (hGHR) gene into mouse BaF3 cells as follows. PCR was carried out using a hGHR ECD artificially synthesized gene having the nucleotide sequence set for as SEQ ID NO:38 (a 5' side fragment of the hGHR gene encoding the extra cellular domain of hGHR), as a template, and primer YA034 (SEQ ID NO:39) and primer YA035 (SEQ ID NO:40). The PCR product was subjected to agarose electrophoresis and purified using QIAEX II (QIAGEN Inc.). This DNA fragment was employed as megaprimer. Using cDNA derived from human lung as a template, and primer K708 (SEQ ID NO:41) and primer K709 (SEQ ID NO:42), PCR was carried out to multiply a DNA fragment including the full length hGHR gene. The PCR product thus obtained was subjected to agarose electrophoresis, and purified using QIAEX II (QIAGEN Inc.). Using the purified DNA fragment including the full-length hGHR gene as a template, and the above megaprimer and primer K709 (SEQ ID NO:42), PCR was carried out to amplify the DNA fragment having the nucleotide sequence set forth as SEQ ID NO:43, which included a gene encoding the full-length hGHR that had a hGHR ECD artificially synthesized nucleotide sequence on the 5' end. This DNA fragment was digested with restriction enzymes (MluI and NotI) and then inserted between MluI and NotI sites of retrovirus vector pMX-II (Ono Y., Oncogene. 19. 3050-8 (2000)) to provide a retrovirus vector for hGHR expression (hGHR/pMX-II).

In 10 mL of DMEM medium containing 10% FBS, $6 \times 10^6$ of "293 cells" (Dainippon Pharmaceutical Inc.) were suspended. This suspension was added to 10-cm dishes and cultured for 24 hours at 37° C. under 5% $CO_2$. The "293 cells" employed here was human embryonic kidney cells transformed with the E1 gene of adenovirus.

To 500 μL of Opti-MEMI™ medium (Thermo Fisher Scientific Inc.) was added 15 μL of X-tremeGENE™ 9 DNA Transfection Reagent (Roche Inc.) and mixed, and to this mixture, 5 μg of the retrovirus packaging vector pCL-Eco (IMGENEX Inc.) and 5 μg of hGHR/pMX-II were further added and mixed. This mixture solution was left undisturbed for 15 minutes at room temperature, and then added to the above mentioned 10-cm dishes in which the "293 cells" had been cultured for 24 hours. The cells then were cultured for 24 hours at 37° C. under 5% $CO_2$, and the medium then was centrifuged at 3000 rpm for 5 minutes to collect the supernatant. The supernatant thus collected was used as the hGHR expressing retrovirus solution.

WEHI-3 cells (Riken) were cultured in RPM1640 medium containing 10% FBS, and the medium were centrifuged at 3000 rpm for 5 minutes to collect the supernatant. To 2 mL of the hGHR expressing retrovirus solution were added 500 μL of the culture supernatant of WEHI-3 cells and 2.5 mL of RPMI1640 medium containing 10% FBS, and mixed. This mixture solution was added to $2 \times 10^6$ of BaF3 cells (Riken), an IL-3 dependent cell line, and the cells were suspended. This cell suspension was transferred to a 75-cm² culture flask and cultured under 5% $CO_2$ at 37° C. for 8 hours, and following addition of 500 μL of the supernatant of WEHI-3 cell culture and 2.5 mL of RPMI1640 medium containing 10% FBS, cultured for further 16 hours. After completion of the culture, the cells were collected by centrifugation and washed three times with PBS. To the collected cells was added 5 mL of RPM1640 medium containing 10% FBS and 100 ng/mL of 22K hGHR to suspend the cells, and the suspended cells were transferred to a culture flask and cultured under 5% $CO_2$ at 37° C. to obtain BaF3 cells that had acquired GH-dependent growth ability as a result of the expression of the hGHR gene. The cells were designated as BaF3/hGHR cells.

[Example 9] Measurement of Cell Growth Activity Using BaF3/hGHR Cells

Cell growth activity of HSA-hGH fusion protein was evaluated using the BaF3/hGHR cells prepared by the method described in Example 8, that cells were acquired GH-dependent growth ability as a result of the introduction of the human GH receptor (hGHR) gene into the mouse BaF3 cells.

BaF3/hGHR cells at the logarithmic growth phase were washed three times with PBS, and diluted to $1\times10^6$ cells/mL with 15 mL of RPMI1640 medium containing 1% horse serum, and cultured under 5% $CO_2$ at 37° C. for 16 hours. After the culture, the cells were diluted to $3\times10^5$ cells/mL with the same medium, and 100 μL of it was seeded in each well of a 96-well culture plate. The 22K hGH (Growject™, JCR Pharmaceuticals Inc.), 20K hGH (ATGen Inc.), and three species of the HSA-hGH fusion proteins (HSA-22K hGH, HSA-20K hGH, and HSA-[linker]-20K hGH) purified in Example 7) were respectively diluted to prepare 8-stepwise dilutions in the concentration range shown in Table 1.

[Table 1]

TABLE 1

Preparation of diluents of each sample

| Test Sample | Concentration range |
|---|---|
| 22KhGH | 44.8 nM~$2.2 \times 10^{-5}$ nM |
| 20KhGH | 49.0 nM~$2.4 \times 10^{-5}$ nM |
| HSA-22KhGH | 90.3 nM~$4.3 \times 10^{-5}$ nM |
| HSA-20KhGH | 92.3 nM~$4.4 \times 10^{-5}$ nM |
| HSA-[linker]-20KhGH | 91.2 nM~$4.4 \times 10^{-5}$ nM |

The diluted sample solutions thus prepared was added, 20 μL each, to each well of the 96-well culture plate that had been seeded with BaF3/hGHR cells, mixed on a plate shaker, and cultured at 37° C. under 5% $CO_2$ for 22 hours. Thus the final concentration range of each test sample in the medium was about 0.167 times that shown in Table 1. After this culture, CellTiter 96™ Aqueous One Solution Cell Proliferation Assay test solution (Promega Inc.), which was a reagent in colorimetric analysis for counting the number of living cells, was added to the well, 24 μL each, and mixed, and the culture was continued for further 3 hours. Then the absorbance at 490 nm of each well was measured using a plate reader. The values measured were plotted, with absorbance at 490 nm on the vertical axis, and molar concentration (nM) of each test sample on the horizontal axis. As absorbance at 490 nm indicated a relative value corresponding to the number of living cells, the curve produced by plotting the measured values represented the correlation between the concentration of the test sample and the level of the cell growth. The concentration of the test sample at which the level of the cell growth was 50% of the maximum cell growth on the curve was determined as $EC_{50}$. Measurement was carried out two times for each test sample.

[Example 10] Preparation of BaF3/hPRLR Cells

BaF3/hPRLR cells having acquired prolactin-dependent growth ability was produced by introducing of human prolactin receptor (hPRLR) gene into mouse BaF3 cells as follows. PCR was carried out using a human spleen-derived cDNA as template, and primer YA001 (SEQ ID NO:44) and primer YA002 (SEQ ID NO:45) to amplify the hPRLR gene. The obtained PCR product was digested with restriction enzymes (SalI and NotI) and incorporated between SalI and NotI of the retroviral vector pMX-II, which was designated as retroviral vector (hPRLR/pMX-II) for hPRLR expression.

$6\times10^6$ cells of 293 cell were suspended in DMEM containing 10 mL of 10% FBS, and this suspension was added to a 10-cm cell culture dish, and cultured at 37° C. under 5% $CO_2$ for 24 hours.

15 μL of X-treme GENE™ 9 DNA Transfection Reagent (Roche Inc.) was added to 500 μL of Opti-MEMI™ and mixed. To this mixture, 5 μg of pCL-Eco (IMGENEX Inc.) and 5 μg of hPRLR/pMX-II were further added and mixed. This mixed solution was allowed to stand at room temperature for 15 minutes and then added to a 10-cm dish in which the 293 cells had been cultured for 24 hours as described above. Subsequently, the cells were cultured at 37° C. for 24 hours under 5% $CO_2$, and then the medium was centrifuged at 3000 rpm for 5 minutes to collect the supernatant. The collected supernatant was used as hPRLR-expressing retrovirus solution.

To 2 mL of hPRLR expressing-retrovirus solution, 500 μL of culture supernatant of WEHI-3 cells and 2.5 mL of RPMI 1640 medium containing 10% FBS were added and mixed. This mixed solution was added to $2\times10^6$ cells of BaF3 cell, an IL-3 dependent cell line, to suspend the cells. The cell suspension thus prepared was transferred to a 75 cm$^2$ culture flask and the cells were cultured at 37° C. under 5% $CO_2$ for 8 hours. Subsequently, 500 μL of culture supernatant of WEHI-3 cells and 2.5 mL of RPMI 1640 containing 10% FBS were added and the cells were cultured for 16 hours. After the culture, the cells were collected by centrifugation and washed three times with PBS. 5 mL of RPMI 1640 medium containing 100 ng/mL of hPRLR and 10% FBS was added to the collected cells and the cells were suspended. Then the cell suspension was transferred to a culture flask and incubated at 37° C. under 5% $CO_2$ to obtain BaF3 cells which acquired hPRL-dependent proliferative capacity by expressing hPRLR. This cell was designated as a BaF3/hPRLR cell.

[Example 11] Measurement of Prolactin (PRL)-Like Activity Using BaF3/hPRLR Cells The prolactin (PRL)-like activity of each of HSA-hGH fusion proteins was evaluated by the method using BaF3/hPRLR cells which were prepared by the method described in Example 10 and acquired PRL dependent proliferative capacity by introducing human prolactin receptor (hPRLR) gene into mouse BaF3 cells.

The BaF3/hPRLR cells in logarithmic growth phase were washed 3 times with PBS, diluted to $1\times10^6$ cells/mL with 15 mL of RPMI 1640 medium containing 5% FBS and incubated at 37° C. under 5% $CO_2$ for 16 hours. After the culture, the cells were diluted with the same medium to $3\times10^5$ cells/mL, and seeded, 100 μL each, in wells of a 96-well culture plate. Each of 22K hGH (Growject™, JCR Pharma Inc.), 20K hGH (ATGen Inc.), and the three HSA-hGH fusion proteins (HSA-22K hGH, HSA-20K hGH, and HSA-[linker]-20K hGH, purified in example 7) were diluted to prepare 7-stepwise sample dilutions in the concentration range shown in Table 2. Further, as a positive control, human prolactin dilutions (hPRL, R&D System Inc.) were prepared.

[Table 2]

TABLE 2

Preparation of diluents of each sample

| Test Sample | Concentration range |
| --- | --- |
| 22KhGH | 44.8 nM~2.9 × $10^{-3}$ nM |
| 20KhGH | 49.0 nM~3.1 × $10^{-3}$ nM |
| HSA-22KhGH | 90.3 nM~5.8 × $10^{-3}$ nM |
| HSA-20KhGH | 92.3 nM~5.9 × $10^{-3}$ nM |
| HSA-[linker]-20KhGH | 91.2 nM~5.8 × $10^{-3}$ nM |
| hPRL | 43.7 nM~2.8 × $10^{-3}$ nM |

20 μL each of the sample dilutions thus prepared was added to each well of a 96-well culture plate, to which BaF3/hPRLR cells had been added, and mixed using a plate shaker, and the cells were cultured at 37° C. under 5% $CO_2$ for 22 hours. Accordingly, the final concentration range of each test sample in the medium was about 0.167 times that shown in Table 2. After the culture, 24 μL of CellTiter 96™ Aqueous One Solution Cell Proliferation Assay test solution (Promega Inc.) was added to each well and mixed, and the cells were further cultured for 3 hours. The values measured were plotted, with absorbance at 490 nm on the vertical axis, and molar concentration (nM) of each test sample on the horizontal axis. As absorbance at 490 nm indicated a relative value corresponding to the number of living cells, the curve produced by plotting the measured values represented the correlation between the concentration of the test sample and the level of the cell growth. The concentration of the test sample at which the level of the cell growth was 50% of the maximum cell growth on the curve was determined as $EC_{53}$. All the measurements were carried out by double test.

[Example 12] Measurement of Inhibitory Activity of hGHBP on the Cell Growth Activity BaF3/hGHR cells in logarithmic growth phase were washed three times with PBS, diluted to 1×$10^6$ cells/mL with 15 mL of RPMI 1640 medium containing 1% horse serum, and incubated at 37° C. under 5% $CO_2$ for 16 hours.

After the culture, the cells were diluted with the same medium to 3×$10^5$ cells/mL and seeded, 100 μL each, in each well of a 96-well culture plate. Each of HSA-20K hGH, HSA-[linker]-20K hGH, both purified in Example 7, and 22K hGH (Growject™, JCR Pharmaceuticals Inc.) was diluted with PBS containing 0.1% BSA to prepare the diluted sample solutions at the concentration of 0.1 nM.

The diluted sample solution thus prepared, 20 μL each, was added to each well of the 96-well culture plate to which BaF3/hGHR cells had been added. Further, recombinant human growth hormone binding protein (rhGHBP, BioVision Inc.) was dissolved in PBS containing 0.1% BSA at the concentrations of 1, 10, and 100 nM, and added, 20 μL each, to the each well, respectively. Thus the concentrations of hGHBP in the medium were 0.143, 1.43, and 14.3 nM, respectively. After mixing the solutions in a 96-well culture plate with a plate shaker, the cells were cultured at 37° C. under 5% $CO_2$ for 22 hours. After incubation, the absorbance at 490 nm of each well was measured using a plate reader. The values measured were plotted, with absorbance at 490 nm on the vertical axis, and molar concentration (nM) of hGHBP on the horizontal axis. As absorbance at 490 nm indicated a relative value corresponding to the number of living cells, the curve produced by plotting the measured values represented the correlation between the concentration of hGHBP and the growth level of the cells. The concentration of hGHBP at which the level of the cell growth was 50% relative to the maximum value of the level of cell growth on the curve was determined as $IC_{50}$. All the measurements were carried out by double test. The larger the value of $IC_{50}$ measured by this measurement method is, the lower the affinity for hGHBP is.

[Example 13] Pharmacokinetics and Efficacy Analysis Using Cynomolgus Monkey

HSA-22K hGH and HSA-20K hGH purified in Example 7 were subcutaneously administered to male cynomolgus monkeys at a dose of 4.0 mg/kg once, respectively. Administrations of HSA-22K hGH and HSA-20K hGH were performed using three cynomolgus monkeys for each of them.

For pharmacokinetic analysis, peripheral blood of the animals was collected 15 minutes, 1, 4, 8, 12, 24, 48, 72, 120, 168, and 216 hours after administration. The blood was collected in a blood collection tube containing di-potassium EDTA, cooled on ice, and centrifuged (1700×g, 5 minutes, 4° C.) to separate the plasma. The concentration of HSA-hGH fusion protein contained in the plasma thus prepared was measured by the method detailed in Example 14, by plotting the concentration of HSA-hGH fusion protein on the vertical axis and the time after administration on the horizontal axis, C max, $AUC_{0-216h}$, $AUC_{0-inf}$ and $t_{1/2}\beta$ were measured as the pharmacokinetic analysis.

Further, the pharmacological effect of HSA-hGH fusion protein was analyzed as follows using promotion of IGF-1 secretion as an index. Peripheral blood was taken before administration, as well as 6 and 12 hours and 1, 2, 3, 4, 5, 6, 7, 8, and 9 days after administration, and plasma was prepared from the peripheral blood in the above-described manner. The concentration of IGF-1 in the plasma was determined by the method detailed in Example 13, and pharmacological analysis was performed by plotting the concentration of IGF-1 on the vertical axis, and the time elapsed after administration on the horizontal axis. Furthermore, as a control, an additional cynomolgus monkey was provided, and 22K hGH (Growject™) was administered to it subcutaneously at a dose of 0.3 mg/kg for 7 consecutive days, and the concentration of IGF-1 in plasma was measured simultaneously.

[Example 14] Determination of HSA-hGH Fusion Protein in Plasma

Mouse anti-HSA monoclonal antibody and mouse anti-hGH antibody were obtained by culturing hybridoma cells produced by fusing mouse spleen cells immunized by HSA or hGH with myeloma cells by a conventional method well known to those skilled in the art. Mouse anti-hGH monoclonal antibody was dialyzed against 0.1 M $NaHCO_3$ solution (pH 9), and the concentration of the antibody in the solution was measured using NanoDrop™ (Thermo Scientific Inc.). EZ-Link™ NHS-LC-Biotin (Thermo Fisher Scientific Inc.) dissolved at 5 mg/mL in DMSO then was added to the antibody solution at a ratio of 60 μg of NHS-LC-Biotin per 1 mg of the antibody, and after letting a reaction take place for 2 hours at room temperature, the reaction solution was dialyzed against PBS to obtain biotinylated mouse anti-hGH monoclonal antibody. The mouse anti-HSA monoclonal antibody was used as the primary antibody, and the biotinylated mouse anti-hGH monoclonal antibody as the secondary antibody, respectively, in the determination method described below.

The concentration of the HSA-hGH fusion protein in plasma was determined by electrochemiluminescence (ECL) immunoassay. ECL immunoassay is a method in which a sample is quantified by applying electrochemical stimulation to a secondary antibody labeled with a ruthenium complex, SULFO-TAG, on a plate while detecting the luminescence with a CCD camera at the wavelength of 620 nm generated by electrolytic oxidation-reduction of SULFO-TAG.

Measurement was carried out largely in the following manner according to the product manual of Sector Imager 6000. The mouse anti-HSA monoclonal antibody was added to High Bind Plate (Meso Scale Diagnostics Inc.), and left undisturbed for one hour to immobilize the anti-HSA antibody (primary antibody) to the plate. Superblock Blocking buffer in PBS (Thermo Fisher Scientific Inc.) then was added to the plate, and shaken for one hour to block the plate. The plate was washed with PBST (PBS containing 0.05% Tween20), and following addition of a sample, shaken for one hour. The plate was washed with PBST, and after addition of the biotinylated mouse anti-hGH monoclonal antibody (secondary antibody), shaken for one hour. The plate was washed with PBST, and after addition of SULFO-Tag-Streptavidin (Meso Scale Diagnostics Inc.), shaken for one hour. After washing the plate with PBST, Read buffer T (Meso Scale Diagnostics Inc.) was added, and luminescence at 620 nm was measured using Sector Imager 6000 (Meso Scale Diagnostics inc.). Known concentrations of HSA-hGH were determined in the same manner on the same plate to obtain a standard curve, and the concentration of HSA-hGH in the plasma was determined by interpolating the values measured for the sample.

[Example 15] Determination of IGF-1 in Plasma

Determination of IGF-1 in the plasma was carried out by ELISA using Human IGF-I Quantikine ELISA kit (R&D systems Inc.).

[Example 16] Results and Discussion
(Measurement of Cell Growth Activity Using BaF3/hGHR Cells)

Figure 9:
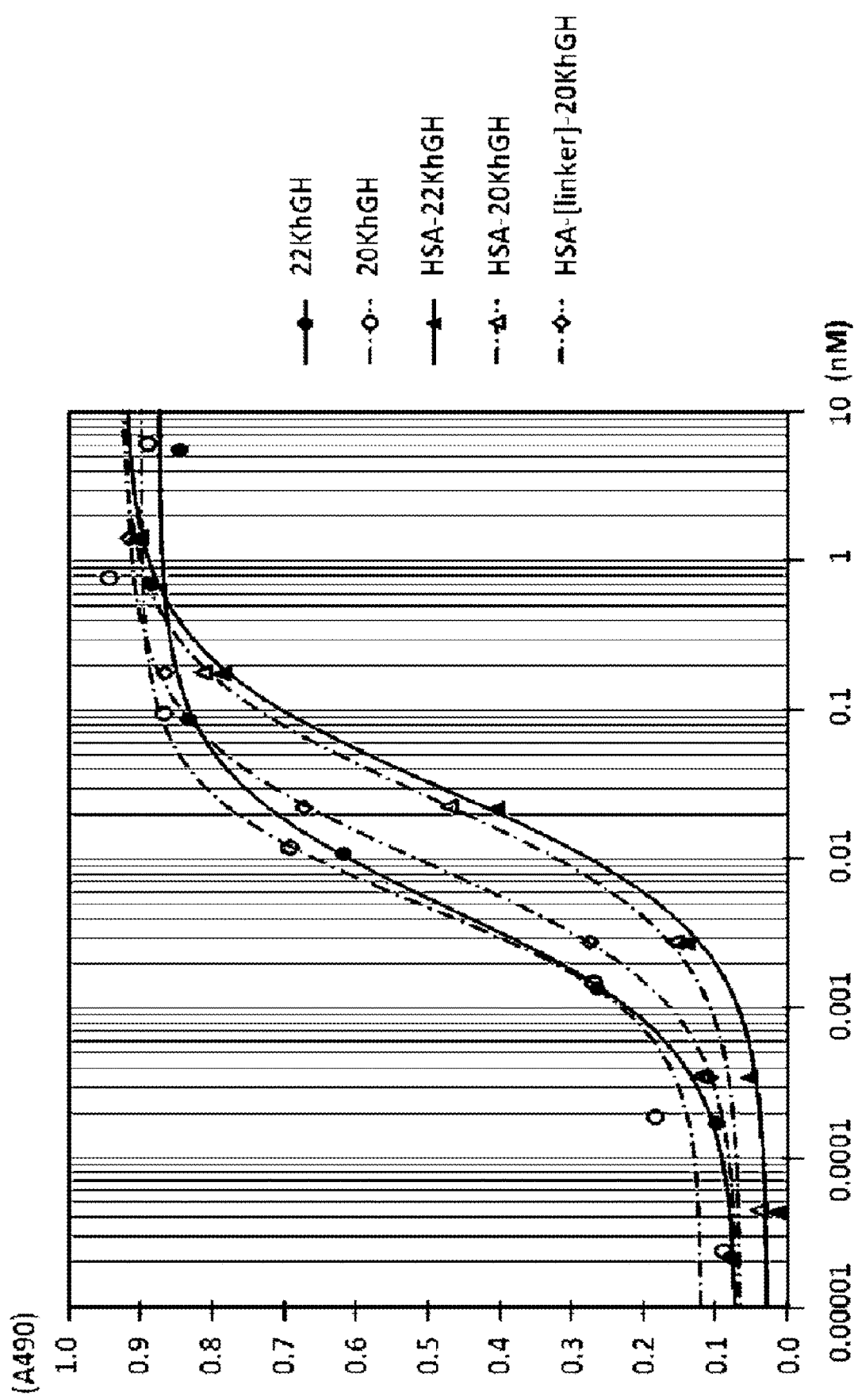
FIG. 9 A figure showing the result of measurement of cell growth activity using BaF3/hGHR cells. The vertical axis denotes absorbance at 490 nm, and the horizontal axis the concentration (nM) of each test sample.

FIG. 9 illustrates the result of the determination of cell growth activity using BaF3/hGHR cells, a figure produced by plotting absorbance at 490 nm on the vertical axis and molar concentration (nM) for each sample on the horizontal axis. The $EC_{50}$ values of each sample were determined based on this figure (Table 3).

[Table 3]

TABLE 3

| | $EC_{50}$ values for each sample (values of cell-growth activity using BaF3/hGHR cells) | | | | |
|---|---|---|---|---|---|
| | 22KhGH | 20KhGH | HSA-22KhGH | HSA-20KhGH | HSA-[linker]-20KhGH |
| $ED_{50}$ (nM) | $8.0 \times 10^{-4}$ | $8.4 \times 10^{-4}$ | $4.9 \times 10^{-3}$ | $4.3 \times 10^{-3}$ | $1.5 \times 10^{-3}$ |

As shown in Table 3, the $EC_{50}$ values of 22K hGH and 20K hGH are $8.0 \times 10^{-4}$ nM and $8.4 \times 10^{-4}$ nM, respectively, indicating that the both have almost equivalent cell growth activities. Further, the $EC_{50}$ of HSA-22K hGH and HSA-20K hGH are $4.9 \times 10^{-3}$ nM and $4.3 \times 10^{-3}$ nM, respectively, indicating that the cell growth activity of HSA-20K hGH is slightly higher than that of HSA-22K hGH. However, the $EC_{50}$ of HSA-22K hGH ($4.9 \times 10^{-3}$ nM) is about 6 times the $EC_{50}$ of the wild-type 22K hGH ($8.0 \times 10^{-4}$ nM), and the $EC_{50}$ of HSA-20K hGH ($4.3 \times 10^{-3}$ nM) is about 5 times the $EC_{50}$ of the wild-type 20K hGH ($8.4 \times 10^{-4}$ nM). That is, when 22K hGH and 20K hGH are fused without a linker to configure the fusion proteins, their cell proliferation activities decrease as compared with their wild-type counterparts.

On the other hand, the $EC_{50}$ of HSA-[linker]-20K hGH obtained by fusing the C-terminus of HSA and the N-terminus of 20K hGH via a linker part consisting of 20 amino acids set forth as SEQ ID NO:5 is $1.5 \times 10^{-3}$ nM, which shows that HSA-[linker]-20K hGH has higher cell growth activity than HSA-20K hGH ($EC_{50}$: $4.3 \times 10^{-3}$ nM). Further, the $EC_{50}$ of HSA-[linker]-20K hGH ($1.5 \times 10^{-3}$ nM) is about 1.9 times the $EC_{50}$ of 22K hGH ($8.0 \times 10^{-4}$ nM). That is, although HSA-[linker]-20K hGH has a slightly lower cell growth activity than 22K hGH, it retains cell growth activity to the extent that it can suitably be used as a therapeutic agent for growth hormone deficiency short stature.

[Example 17] Results and Discussion
(Measurement of Prolactin (PRL)-Like Activity Using BaF3/hPRLR Cells)

Figure 10:
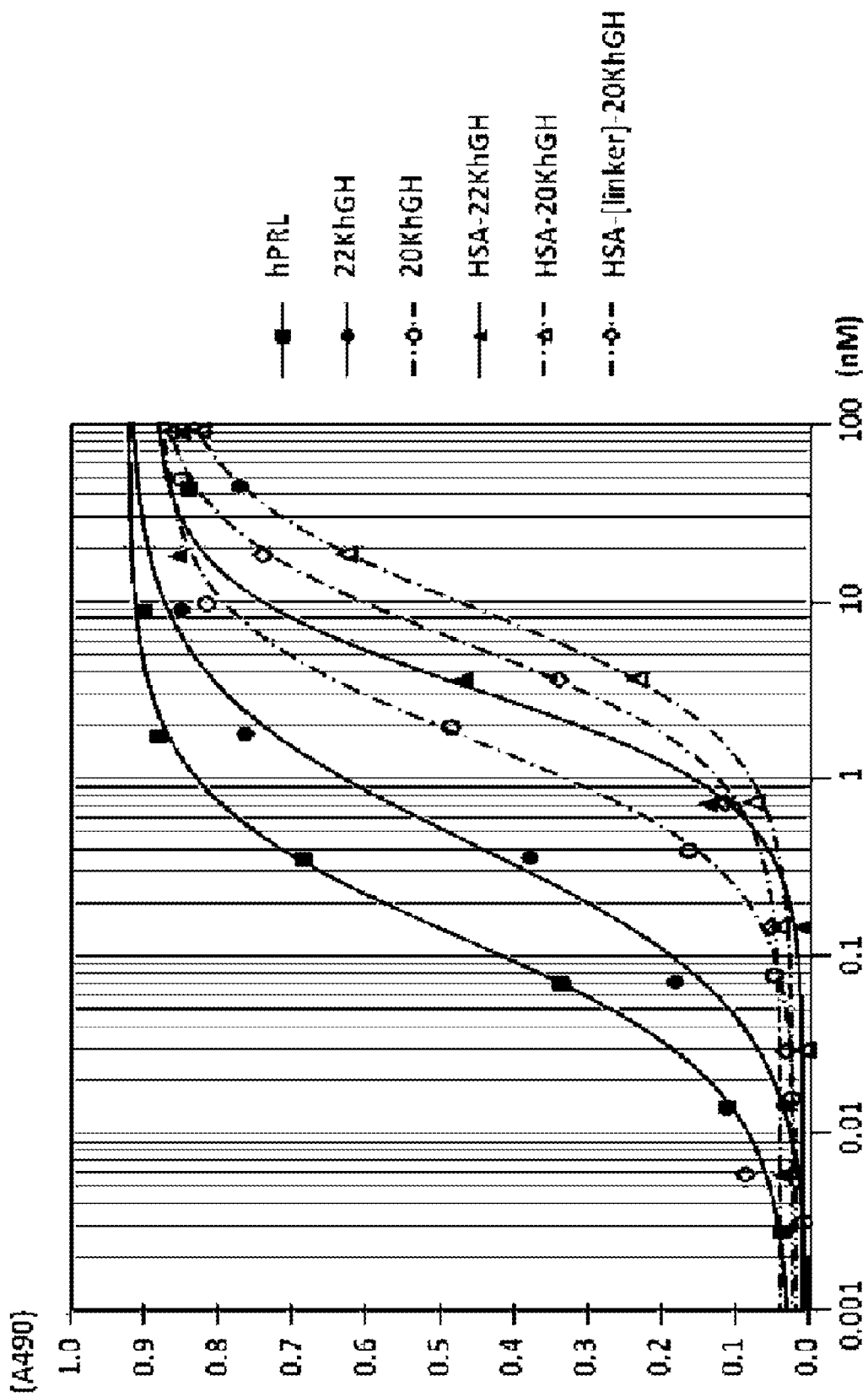
FIG. 10 A figure showing the result of measurement of prolactin (PRL)-like activity using BaF3/hPRLR cells. The vertical axis denotes absorbance at 490 nm, and the horizontal axis the concentration (nM) of each test sample.

FIG. 10 illustrates the result of the determination of prolactin (PRL)-like activity using BaF3/hPRLR cells, a figure produced by plotting absorbance at 490 nm on the vertical axis and molar concentration (nM) for each sample on the horizontal axis. The $EC_{50}$ values for each sample determined based on this figure (Table 4). First of all, the $EC_{50}$ of human prolactin, which was used as a positive control, was $2.1 \times 10^{-3}$ nM, indicating that prolactin (PRL)-like activity can be measured quantitatively by this assay method using BaF/hPRLR cells.

[Table 4]

TABLE 4

| | $EC_{50}$ values for each sample (values of prolactin-like activity using BaF3/hPRLR cells) | | | | |
|---|---|---|---|---|---|
| | 22KhGH | 20KhGH | HSA-22KhGH | HSA-20KhGH | HSA-[linker]-20KhGH |
| $ED_{50}$ (nM) | $7.2 \times 10^{-2}$ | $2.7 \times 10^{-1}$ | $5.2 \times 10^{-1}$ | 1.5 | $9.6 \times 10^{-1}$ |

As shown in Table 4, when comparing $EC_{50}$s of 22K hGH and 20K hGH, the $EC_{50}$ of 22K hGH and 20K hGH are $7.2 \times 10^{-2}$ nM and $2.7 \times 10^{-1}$ nM, respectively, indicating that the prolactin-like activity of 20K hGH is lower than that of 22K hGH.

Further, the $EC_{50}$s of HSA-22K hGH and HSA-20K hGH are $5.2 \times 10^{-1}$ nM and 1.5 nM, respectively, indicating that the prolactin-like activity of HSA-20K hGH is lower than that of HSA-22K hGH, in the same way as comparing wild-types of 22K hGH and 20K hGH.

Further, the $EC_{50}$ of HSA-[linker]-20K hGH, in which the C-terminus of HSA and the N-terminus of 20K hGH are fused via a linker part consisting of 20 amino acids, is $9.6 \times 10^{-1}$ nM. That is, HSA-[linker]-20K hGH has high prolactin-like activity as compared with HSA-20K hGH ($EC_{50}$: 1.5 nM) in which HSA and 20K hGH are linked without via a linker part. However, when comparing prolactin-like activity with 22K hGH, a human growth hormone preparation, $EC_{50}$ of HSA-[linker]-20K hGH ($9.6 \times 10^{-1}$ nM) is about 13 times that of 22K hGH ($7.2 \times 10^{-2}$ nM). These results indicate that HSA-[linker]-20K hGH, in the same way as HSA-20K hGH, has significantly lower prolactin-like activity than wild-type 22K hGH.

[Example 18] Results and Discussion (Inhibitory Activity of hGHBP Against Cell Proliferation Activity)

Figure 11:
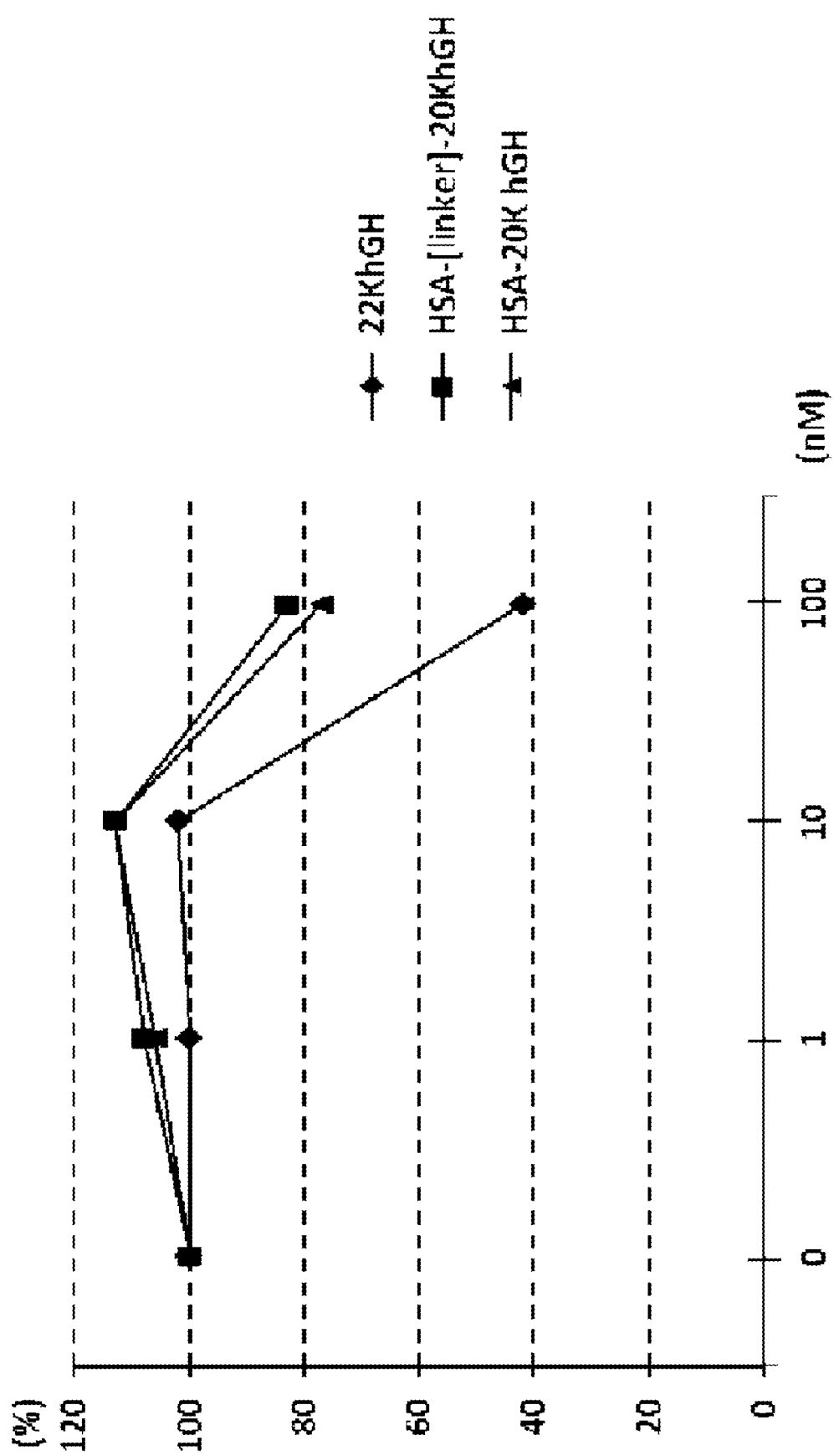
FIG. 11 A figure showing the result of inhibitory activity of hGHBP against cell growth activity. The vertical axis denotes the absorbance at 490 nm relative to the value measured without addition of hGHBP, that value is taken as 100%, and the horizontal axis the concentration (nM) of hGHBP.

FIG. 11 illustrates the result of the determination of prolactin (PRL)-like activity using BaF3/hPRLR cells, a figure produced by plotting absorbance at 490 nm on the vertical axis and molar concentration (nM) of hGHBP on the horizontal axis. The 490 nm of vertical axis represents the relative value (%) when the measured value without hGHBP is taken as 100%. The $IC_{50}$ of hGHBP against 22K hGH is in the range of 60 to 80 nM, whereas the $IC_{50}$s of hGHBP against HSA-20K hGH and HSA-[linker]-20K hGH are both estimated to be 250 nM to 350 nM by extrapolation. These results indicate that both of HSA-20K hGH and HSA-[linker]-20K hGH have lower affinities with hGHBP than 22K hGH.

[Example 19] Results and Discussion (Pharmacokinetic Analysis Using Cynomolgus Monkey)

Figure 12:
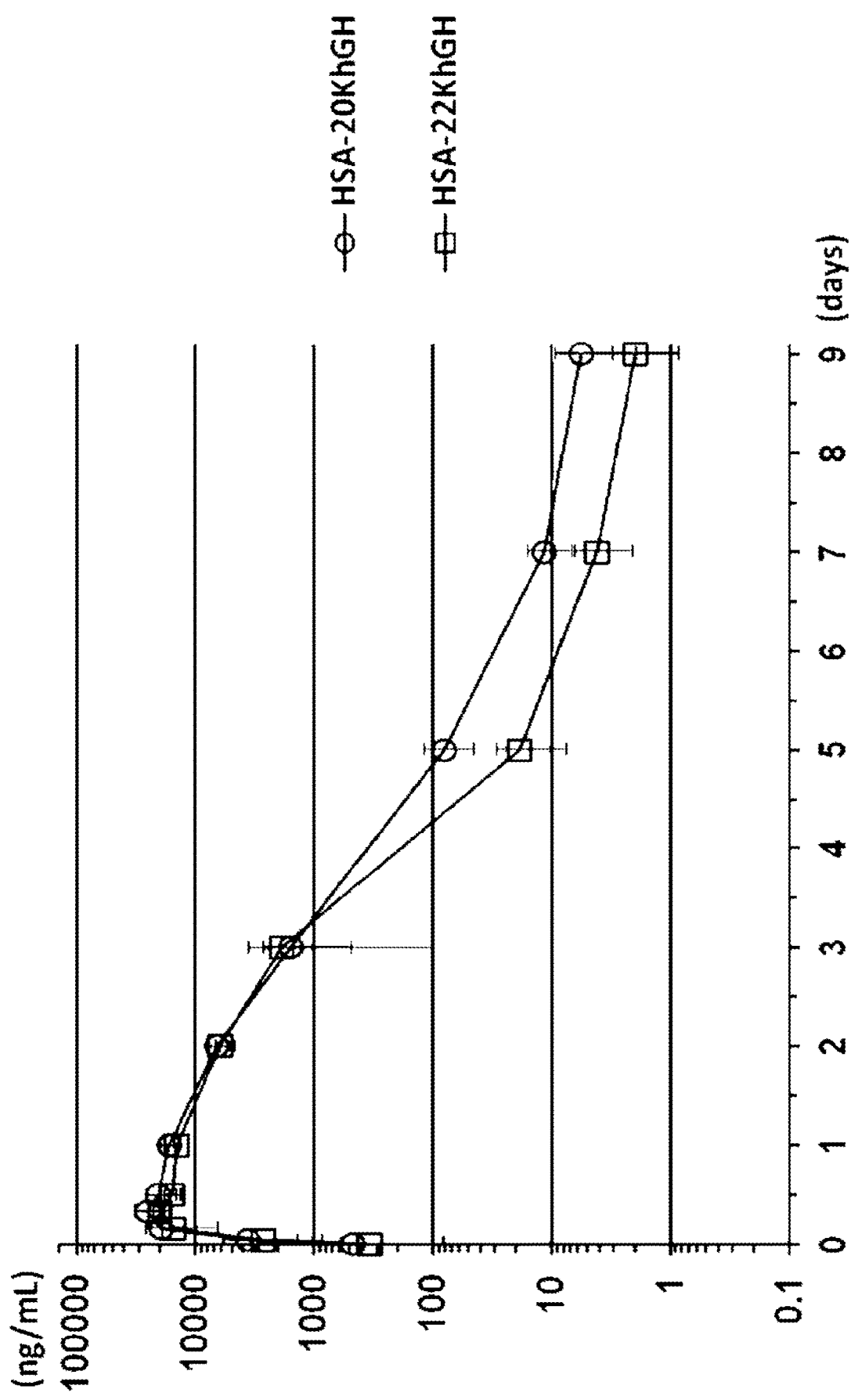
FIG. 12 A figure showing the result of pharmacodynamic analysis of HSA-hGH fusion protein using cynomolgus monkeys. The vertical axis denotes the concentration (ng/mL) of HSA-hGH fusion protein in cynomolgus monkeys' plasma, and the horizontal axis elapsed time (days) after the administration of HSA-hGH fusion protein. The vertical bars in the graph show standard deviation.

FIG. 12 illustrates the result of the determination of pharmacokinetic analysis of HSA-hGH fusion proteins, a figure produced by plotting the concentration of HSA-hGH fusion proteins (HSA-20K hGH and HSA-22K hGH) on vertical axis and the time after administration of the HSA-hGH fusion proteins on the horizontal axis. Table 5 shows the resulting Cmax, $AUC_{0-216h}$, $AUC_{0-inf}$, and $t_{1/2\beta}$ of each test sample based on this figure.
[Table 5]

TABLE 5

Values of Pharmacokinetic analysis for each sample

| | $C_{max}$ (μg/mL) | $AUC_{0-216\,h}$ (μghr/mL) | $AUC_{0-inf}$ (ughr/mL) | $T^{1/2}\beta$(hr) |
|---|---|---|---|---|
| HSA-20KGH | 25.5 ± 7.2 | 871 ± 115 | 872 ± 115 | 28.5 ± 14.7 |
| HSA-22KGH | 20.1 ± 3.4 | 751 ± 54 | 752 ± 55 | 30.0 ± 1.5 |

As shown in Table 5, $AUC_{0-inf}$s of HSA-20 HSA-20K hGH and HSA-22K hGH are 872±115 μg hr/mL and 752±55 μg hr/mL, respectively. Further, as shown in FIG. 12, HSA-20K hGH and HSA-22K hGH are both detected in the blood even on 9th day after administration. Considering that common 22k GH is rapidly degraded after administration, not detected in the blood one day after administration, these data show that hGH is stabilized in the blood by binding it to the C-terminal side of HSA.

[Example 20] Results and Discussion (Pharmacological Analysis Using Cynomolgus Monkey)

Figure 13:
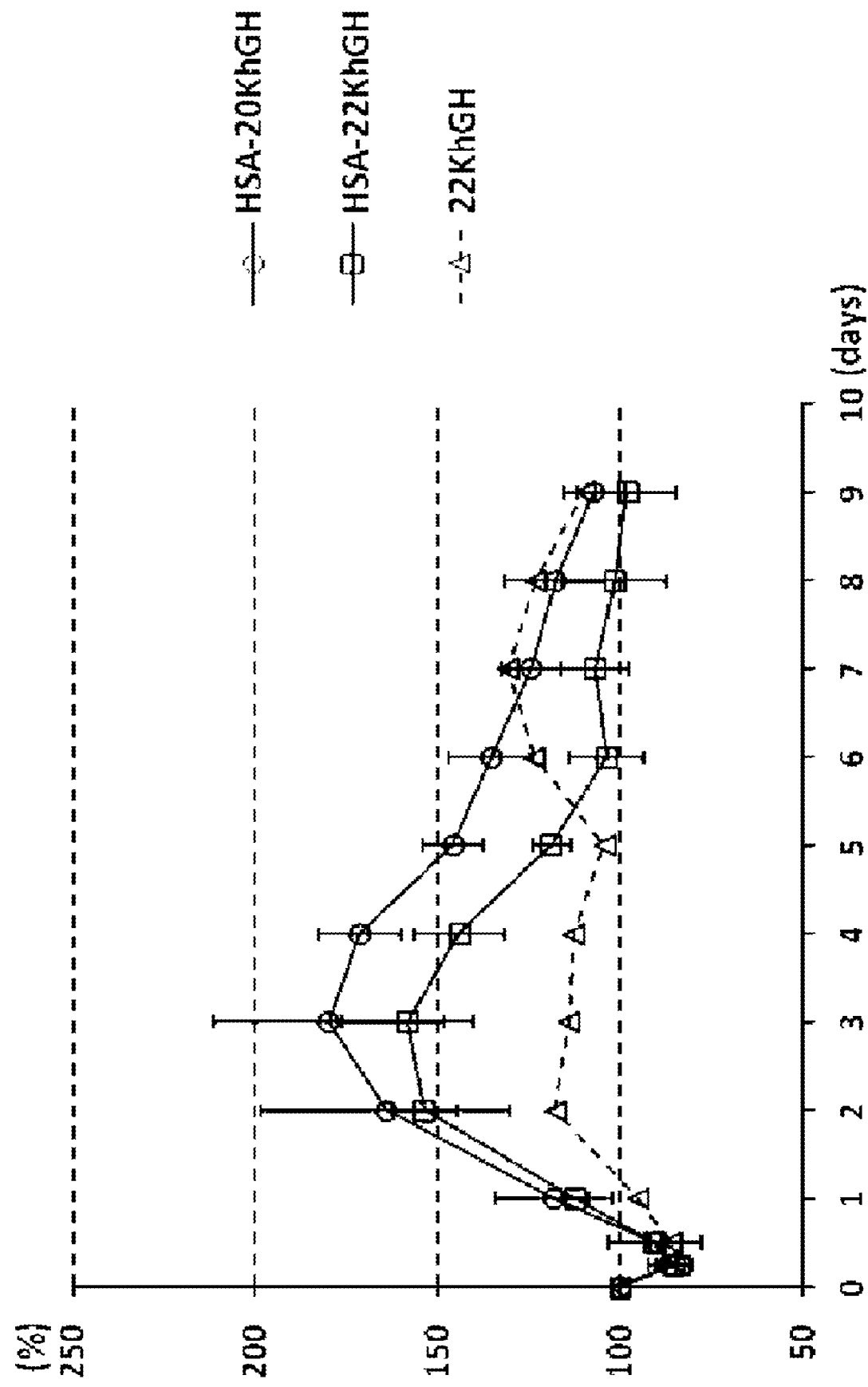
FIG. 13 A figure showing the result of analysis of pharmacological effect of HSA-hGH fusion protein using cyno-molgus monkeys. The vertical axis denotes the concentration (%) of IGF-1 in plasma of cynomolgus monkeys after administration of HSA-hGH fusion protein relative to its concentration before the administration, that concentration is taken as 100%, and the horizontal axis denotes elapsed time (day) after the administration of HSA-hGH fusion protein. The vertical bars in the graph show standard deviation.

FIG. 13 illustrates the results of pharmacological analysis of HSA-hGH fusion proteins, a figure produced by plotting concentration of IGF-1 in plasma on the vertical axis and time after administration of 22K hGH and HSA-hGH fusion proteins (HSA-20K hGH and HSA-22K hGH) on the horizontal axis. IGF-1 is a polypeptide whose secretion is induced by growth hormone and having activities such as promotion of bone growth. Some of hGH's activities are known to be exhibited via IGF-1.

As shown in FIG. 13, in both of the animals that were administered HSA-20K hGH, a product in which 20K hGH was linked to C-terminus of human serum albumin, or HSA-22K hGH, the concentration of IGF-1 in the plasma shows the maximum value on third day after administration. However, the value of HSA-20K hGH administered animals is at least 10% higher than that of HSA-22K hGH administered animals. Further, in the HSA-22K hGH-administered animals, IGF-1 concentration in the plasma returns to almost the same level before the administration on the sixth day after administration, whereas in HSA-20K hGH-administered animals, IGF-1 concentration in the plasma is maintained higher than the level before administration even on the ninth day after administration. In FIG. 13, the concentration of IGF-1 in the plasma of 22K hGH-administered animals increased from the 2nd day and maintained higher than the level before the administration until the 9th day, the final measurement day. The reason of this is considered that as only 22K hGH was administered every day for 7 days, the effect of 22K hGH appeared accumulated.

[Example 21] Results and Discussion (Summary)

From the above results, although HSA-[linker]-20K hGH has a lower growth-promoting activity, its affinity for hGHBP is also lower than 22K hGH used as a therapeutic agent for such as adult growth hormone secretion deficiency, it is considered that the ratio of the activity masked by binding to hGHBP in blood when administered to humans decreases. Therefore, HSA-[linker]-20K hGH is considered to be capable of exerting a growth-promoting activity at a level that allows its use as a therapeutic agent for adult growth hormone secretion deficiency and a like by administration to humans. Further, as HSA-[linker]-20K hGH is more stable in blood than wild-type 22K hGH due to the presence of the HSA part, HSA-[linker]-20K hGH can maintain the growth-promoting activity for longer period than 22K hGH when administered to humans. In the case of a long-lasting human growth hormone that can continuously exhibit a high growth-promoting activity when administered to humans, its prolactin-like activity is also maintained high in the body, whereby breast cancer may be induced. In the case of HSA-[linker]-20K hGH, however, when administered to humans, it can continuously exhibit high growth-promoting activity in the body for long period, whereas the risk of induction of breast cancer can be almost obviated because of its low prolactin-like activity.

Similarly to HSA-[linker]-20K hGH, although HSA-20K hGH has a lower growth-promoting activity, its affinity for hGHBP is also lower than 22K hGH used as a therapeutic agent for adult growth hormone secretion deficiency and a like, it is considered that the ratio of the activity masked by binding to hGHBP in blood when administered to humans decreases. Therefore, HSA-20K hGH is considered to be capable of exerting a growth-promoting activity in the body at a level that allows its use as a therapeutic agent for adult growth hormone secretion deficiency and a like by administration to humans. Further, as HSA-20K hGH hGH is more stable in blood than wild-type 22K hGH due to the presence of the HSA part, HSA-20K hGH can maintain the growth-promoting activity for long period, whereas when 22K hGH is administered to humans its activity rapidly disappears. In the case of a long-lasting human growth hormone that can continuously exhibit a high growth-promoting activity when administered to humans, its prolactin-like activity is also maintained high in the body, whereby breast cancer may be induced. In the case of HSA-20K hGH, however, when administered to humans, it can continuously exhibit high growth-promoting activity in the body for long period, whereas the risk of induction of breast cancer can be almost obviated because of its low prolactin-like activity.

INDUSTRIAL APPLICABILITY

According to the present invention, a novel medicine is to be provided which is a pharmaceutical composition capable of using as a long-lasting therapeutic agent for growth-hormone deficiency short stature and the like, having lower prolactin-like activity and higher stability in blood than the wild-type 22K hGH.

EXPLANATION OF SIGNS

1 Human serum albumin part
2 Linker part
3 20K hGH part
4 LacZ promoter
5 mPGK promoter
6 Partial sequence of internal ribosome entry site of wild-type mouse encephalomyocarditis virus including the nucleotide sequence set forth as SEQ ID NO:6
6a Partial sequence of internal ribosome entry site mutant-type mouse encephalomyocarditis virus including the nucleotide sequence set forth as SEQ ID NO:7
7 Polyadenylation region of mPGK (mPGKpA)
8 Nucleotide sequence containing EP-1p and its first intron
9 SV40 late polyadenylation region
10 Region containing SV40 early promoter
11 Synthetic polyadenylation region
12 Region containing cytomegalovirus promoter
13 Glutamine synthetase gene
14 Region coding human serum albumin
15 Region coding 22K hGH
15a Region coding 20K hGH
16 Region coding a linker

SEQUENCE LISTING FREE TEXT

SEQ ID NO:4: Primary amino acid sequence of a linker part
SEQ ID NO:5: Amino acid sequence of an exemplified linker part
SEQ ID NO:7: Partial nucleic acid sequence of IRES derived from mutant-type murine encephalomyocarditis virus, synthetic
SEQ ID NO:8: Primer Hyg-Sfi5', synthetic
SEQ ID NO:9: Primer Hyg-BstX3', synthetic
SEQ ID NO:10: IRES-Hygr-mPGKpA, synthetic
SEQ ID NO:11: Amino acid sequence corresponding to hygromycin resistance gene
SEQ ID NO:12: Primer IRES5', synthetic
SEQ ID NO:13: Primer IRES3', synthetic
SEQ ID NO:14: Primer mPGKP5', synthetic
SEQ ID NO:15: Primer mPGKP3', synthetic
SEQ ID NO:16: mPGKp, synthetic
SEQ ID NO:17: Primer GS5', synthetic
SEQ ID NO:18: Primer GS3', synthetic
SEQ ID NO:19: Primer puro5', synthetic
SEQ ID NO:20: Primer puro3', synthetic
SEQ ID NO:21: Nucleic acid sequence containing puromycin resistance gene, synthetic
SEQ ID NO:22: Amino acid sequence corresponding to puromycin resistance gene
SEQ ID NO:23: Primer SV40polyA5', synthetic
SEQ ID NO:24: Primer SV40polyA3', synthetic
SEQ ID NO:25: Primer mIRES-GS5', synthetic
SEQ ID NO:26: Primer mIRES-GS3', synthetic
SEQ ID NO:27: Amino acid sequence of HSA-22K hGH
SEQ ID NO:28: Nucleic acid sequence containing HSA-22K hGH gene, synthetic
SEQ ID NO:29: Amino acid sequence of HSA-20K hGH
SEQ ID NO:30: primer YA055, synthetic
SEQ ID NO:31: Primer YA056, synthetic
SEQ ID NO:32: Primer YA036, synthetic
SEQ ID NO:33: Sequence containing HSA-20K hGH gene, synthetic
SEQ ID NO:34: Primer YA065, synthetic
SEQ ID NO:35: Primer YA066, synthetic
SEQ ID NO:36: Amino acid sequence of HSA-[linker]-20K hGH
SEQ ID NO:37: Nucleic acid sequence containing HSA-[linker]-20K hGH gene, synthetic
SEQ ID NO:38: Nucleic acid sequence coding synthetic hGHR ECD gene, synthetic
SEQ ID NO:39: Primer YA034, synthetic
SEQ ID NO:40: Primer YA035, synthetic
SEQ ID NO:41: Primer K708, synthetic
SEQ ID NO:42: Primer K709, synthetic
SEQ ID NO:43: Nucleic acid sequence coding synthetic hGHR gene, synthetic
SEQ ID NO:44: Primer YA001, synthetic
SEQ ID NO:45: Primer YA002, synthetic
SEQ ID NO:46: human serum albumin Redhill(HSA-Redhill)

SEQUENCE LISTING FREE TEXT

516488US_ST25

The invention claimed is:

1. A fusion protein having growth-promoting activity, and comprising a human serum albumin and a 20K human growth hormone,
wherein the human serum albumin comprises the amino acid sequence set forth as SEQ ID NO:2, of which the tyrosine residue occurring at position 319 from the N-terminus is substituted by any amino acid residue except proline residue, and the alanine residue occurring at position 320 from the N-terminus is substituted by threonine or serine.

2. The fusion protein according to claim 1, wherein the 20K human growth hormone comprises the amino acid sequence set forth as SEQ ID NO:1.

3. The fusion protein according to claim 1, wherein the human serum albumin and the 20K human growth hormone are linked via a linker part.

4. The fusion protein according to claim 3, wherein the linker part consists of a non-peptide linker or a peptide linker.

5. The fusion protein according to claim 4, wherein the linker part consists of the non-peptide linker, and the non-peptide linker consists of polyethylene glycol or a derivative thereof.

6. The fusion protein according to claim 1, wherein the human serum albumin is positioned on the N-terminal side of the growth hormone.

7. The fusion protein according to claim 1, wherein the growth hormone is positioned on the N-terminal side of the human serum albumin.

8. The fusion protein according to claim 1, wherein the human serum albumin and the 20K human growth hormone are linked via a linker part, the C-terminus of the human serum albumin and the N-terminus of the linker part are linked by a peptide bond, and the C-terminus of the linker part and the N-terminus of the 20K human growth hormone are linked by a peptide bond.

9. The fusion protein according to claim 8, wherein the linker part comprises a peptide linker consisting of 1 to 50 amino acids.

10. The fusion protein according to claim 9, wherein the linker part consists of a peptide linker comprising the amino acid sequence set forth as SEQ ID NO:4.

11. The fusion protein according to claim 9, wherein the linker part consists of a peptide linker comprising an amino acid sequence set forth as SEQ ID NO:5.

12. The fusion protein according to claim 1, wherein the human serum albumin and the 20K human growth hormone are linked via a linker part, the C-terminus of the human growth hormone and the N-terminus of the linker part are linked by a peptide bond, and the C-terminus of the linker part and the N-terminus of the 20K human serum albumin are linked by a peptide bond.

\* \* \* \* \*